(12) United States Patent
Lu et al.

(10) Patent No.: US 6,565,848 B1
(45) Date of Patent: May 20, 2003

(54) CADHERIN-LIKE ASYMMETRY PROTEIN-1, AND METHODS FOR ITS USE

(75) Inventors: Peter S. Lu, Mountain View, CA (US); Mark M. Davis, Atherton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/546,934

(22) Filed: Apr. 11, 2000

Related U.S. Application Data

(63) Continuation-in-part of application No. 09/411,328, filed on Oct. 1, 1999, now abandoned.
(60) Provisional application No. 60/102,964, filed on Oct. 2, 1998.

(51) Int. Cl.$^7$ .............................................. A61K 39/395
(52) U.S. Cl. ................................ 424/139.1; 424/154.1; 424/153.1; 435/377
(58) Field of Search .......................... 424/139.1, 153.1, 424/154.1, 173.1; 435/377

(56) References Cited

PUBLICATIONS

Janeway et al. Immunobiology 3rd Edition Garland Publishing Inc, 1997, especially p. 7:2.*
Janeway et al Immunobiology 4th Edition, Garland Press NY 1999, p. 40.*
Drubin et al. (Feb. 1996), "Origins of Cell Polarity," *Cell*, vol. 84:335–344.
Geiger et al. (Oct. 1982), "Spatial Relationships of Microtubule–Organizing Centers and the Contact Area of Cytotoxic T Lymphocytes and Target Cells," *J. of Cell Biol.*, vol. 95:137–143.
Gregorio et al. (1982), "Dynamic Properties of Ankyrin in T Lymphocytes: Colocalization with Spectrin and Protein Kinase Cβ," *J. Cell Biol.*, vol. 125:345–358.
Hofman and Stoffel (1993), "Konferenz der Gesellschaft für Biologische Chemie," *Biol. Chem Hoppe–Seyler*, vol. 374:166.
Knudsen et al. (Dec. 1994), "Four Proline–rich Sequences of the Guanine–nucleotide Exchange Factor C3G Bind with Unique Specificity to the First Src Homology 3 Domain of Crk," *J. of Biol. Chem.*, vol. 269(52):32781–32787.

Kupfer et al. (May 1994), "Small Splenic B Cells that Bind to Antigen–specific T Helper (Th) Cells and Face the Site of Cytokine Production in the Th Cells Selectively Proliferate: Immunofluorecence Microscopic Studies of Th–B Antigen––presenting Cell Interactions," *J. Exp. Med.*, vol. 179:1507–1515.

Kupfer et al. (Mar. 1986), "On the Mechanism of Unidirectional Killing in Mixtures of Two Cytotoxic T Lymphocytes," *J. Exp. Med.*, vol. 163:489–498.

Lee et al. (1988), "Activation Induces a Rapid Reorganization od Spectrin Lymphocytes," *Cell*, vol. 55:807–816.

Lee et al. (1988), "Activation Induces a Rapid Reorganization od Spectrin Lymphocytes," *Cell*, vol. 55:807–816.

Lupas et al. (May 1991), "Predicting Coiled Coils from Protein Sequences," *Science*, vol. 252:1162–1164.

Marra et al. (Feb. 19, 1997) Database EST, No. AA200637, "mu12g07.r1 Soares 2NbMT Mus Musculus cDNA Clone Image: 639228 5', mRNA Sequence.".

NCI–CGAP http//www.ncbi.n1m.nih.gov/ncicgap; Accession No.: AA281512, "National Cancer Institute, Cancer Genome Anatomy Project Tumor Gene Index.".

Negulescu et al. (May 1996), "Polarity of T Cell Shape, Motility, and Sensitivity to Antigen," *Immunity*, vol. 4:421–430.

Pianese et al. (May 29, 1998) Database PIR–62, No. I60486, "A Novel Thyroid transcript Negatively Regulated by TSH.".

* cited by examiner

*Primary Examiner*—Patrick J. Nolan
*Assistant Examiner*—Amy DeCloux
(74) *Attorney, Agent, or Firm*—James S. Keddie; Pamela J. Sherwood; Bozicevic, Field & Francis LLP

(57) ABSTRACT

The present invention relates to molecules involved in cell-cell interactions in the immune system. In particular, the invention relates to a cell surface protein which contains certain classical cadherin characteristics, but it exhibits an apical distribution pattern on the surface of lymphocytes. The membrane location of this molecule correlates with the contact interface between T and B cells, and antibodies against an extracellular domain of this protein disrupt T cell/B cell interactions.

14 Claims, 12 Drawing Sheets

```
   1  MSLLPMILNQ  LFKILVQNEE  DEITATVTRV  LADIVAKCHE  EQLDHSVQSY  IKFVFKTKSY
  61  KERTIHEELP  KNLSDLLKSN  DSTIVKHVLE  HSWFFFAIIL  KSMAQHLIDT  NKIQLPRAQR
 121  FPESYQSELD  NLVMGLCDHV  IWKCKEAPEE  TKRANHSVAR  FLKRCFTFMD  RGFVFKMVNN
 181  YISMFSSGEF  KTLCQYKFDF  LQEVCQHEHF  IPCLPIRSA   NIPDPLTPSE  SIRELHASDM
 241  PEYSVTNEFC  RKHFLIGILL  REVGFACRRD  QDIRHLALAV  LKNLMAKHSF  DDRYREPRKQ
 301  AQIASLYMPL  YGMLLDNMPR  IYLKDLYPFT  VNTSNQGSRD  DLSTNGGFQT  QTVMKHATSV
 361  DTSFSKDVLN  SIAAFSSIAI  STVNHADSRA  SLASLDSNPS  TTEKSSEKTD  NCEKIPRPLS
 421  LIGSTLRFDK  LDQAETRSLL  MCFLHIMKTI  SDETLIAYWQ  RAPSPEVSDF  FSILDVCLQN
 481  FRYLGKRNII  RKIAAAFKFV  QSTQNNRTLK  GSNPSCQTSG  LLSQWMHTTS  GHEGHKQHRS
 541  QTLPIIRGKN  ALSNPKLLQM  LDNSMNSNSN  EIDIVHHVDT  EANIATEVCL  TILDLLSLFT
 601  QVHQRQLQQS  DCQNSLMKRV  FDTYMLFFQV  NQSASALKHV  FASLRLFVCK  FPSAFFQGPA
 661  DLCGSFCYEI  LKCCNHRSRL  TQMEASALLY  FFMSKNFEFN  KQKSIVRSHL  QLIKAVSQLI
 721  ADAGIGGSRF  QHSLAITNNF  ANGDKQMKNS  NFPAEVKDLT  KRIRTVLMAT  AQMKEHEKDP
 781  EMLVDLQYSL  ANSYASTPEL  RRTWLESMAK  IHARNGDLSE  AAMCYIHIAA  LIAEYLKRKG
 841  YWKMEKICTP  PLLPEDTQPC  DSNLLLTTPG  GGSMFSMGWP  AFLSITPNIK  EEGAMKEDSG
 901  MQDTPYNENI  LVEQLYMCVE  FLWKSERYEL  IADVNKPIIA  VFEKQRDFKK  LSDLYYDIHR
 961  SYLKVAEVVN  SEKRLFGRYY  RVAFYGQGFF  EEEEGKEYIY  KEPKLTGLSE  ISQRLLKLYA
1021  DKFGADNVKI  IQDSNKVNPK  DLDPKYAYIQ  VTYVTPFFEE  KEIEDRKTDF  EMHHNINRFV
1081  FETPFTLSGK  KHGGVAEQCK  RRTVLTTSHL  FPYVKKRIQV  ISQSSTELNP  IEVAIDEMSR
1141  KVSELNQLCT  TEEVDMIRLQ  LKLQGSVSVK  VNAGPMAYAR  AFLEETNAKK  YADNQVKLLK
1201  EIFRQFADAC  GQALDVNERL  IKEDQLEYQE  ELRSHYKDML  SELSAJMNEQ  ITGRDDPAKC
1261  GVERPYTTRV  TSKGTAAVPV  VSISSSAEV (SEQ ID NO:1)
```

| | | | | | | | | |
|---|---|---|---|---|---|---|---|---|
| SEQ ID NO:7 | N-Cadherin | LLIDPEDD | (11) | GGG | (68) | DPTAPPY | (41) | FKKLAD |
| SEQ ID NO:8 | P-Cadherin | PLLLPEDD | (11) | GGG | (62) | DPTAPPY | (41) | FKKLAD |
| SEQ ID NO:9 | E-Cadherin | EPLLPPDD | (12) | GGG | (61) | DPTAPPY | (41) | FKKLAD |
| SEQ ID NO:10 | CLASP-1 | PPLLPEDT | (12) | GGG | (30) | D.T..PY | (41) | FKKLSD |

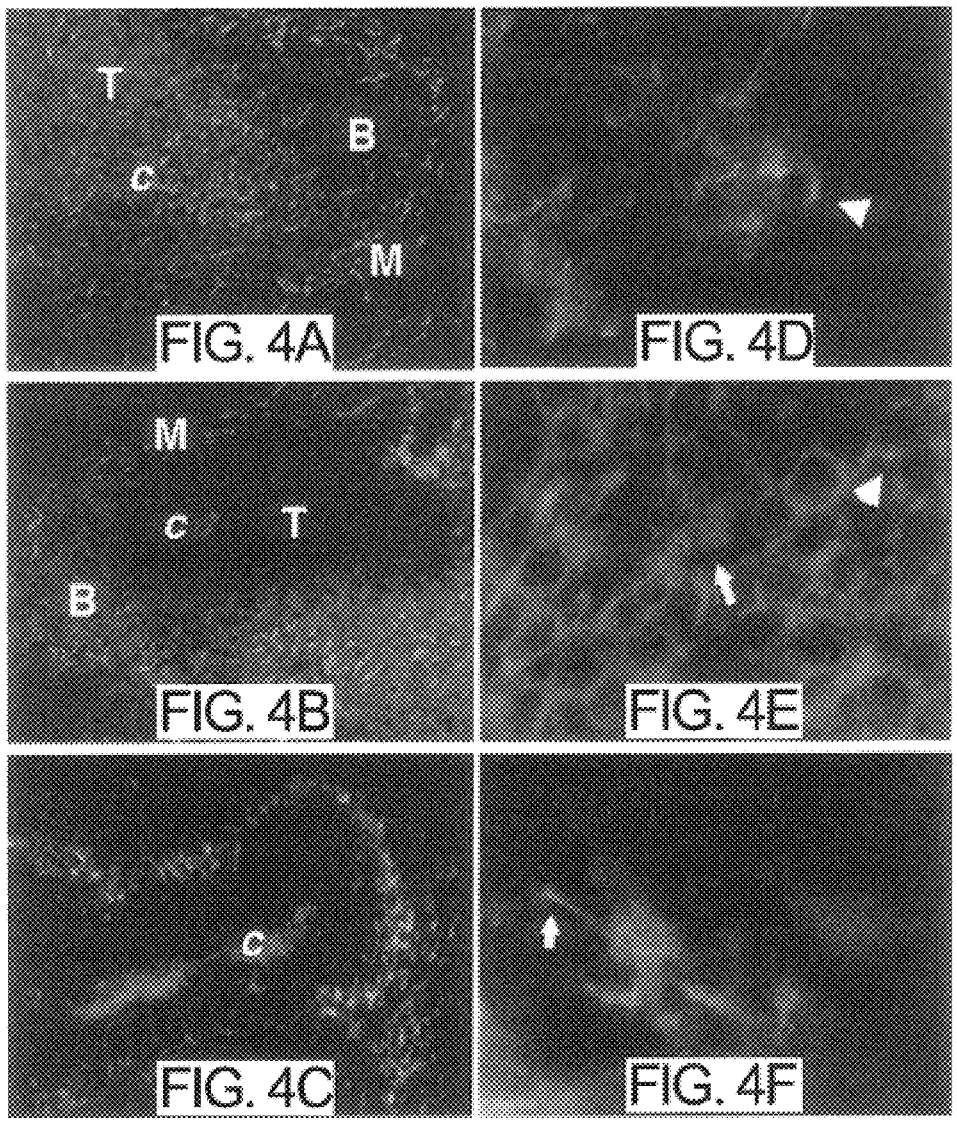

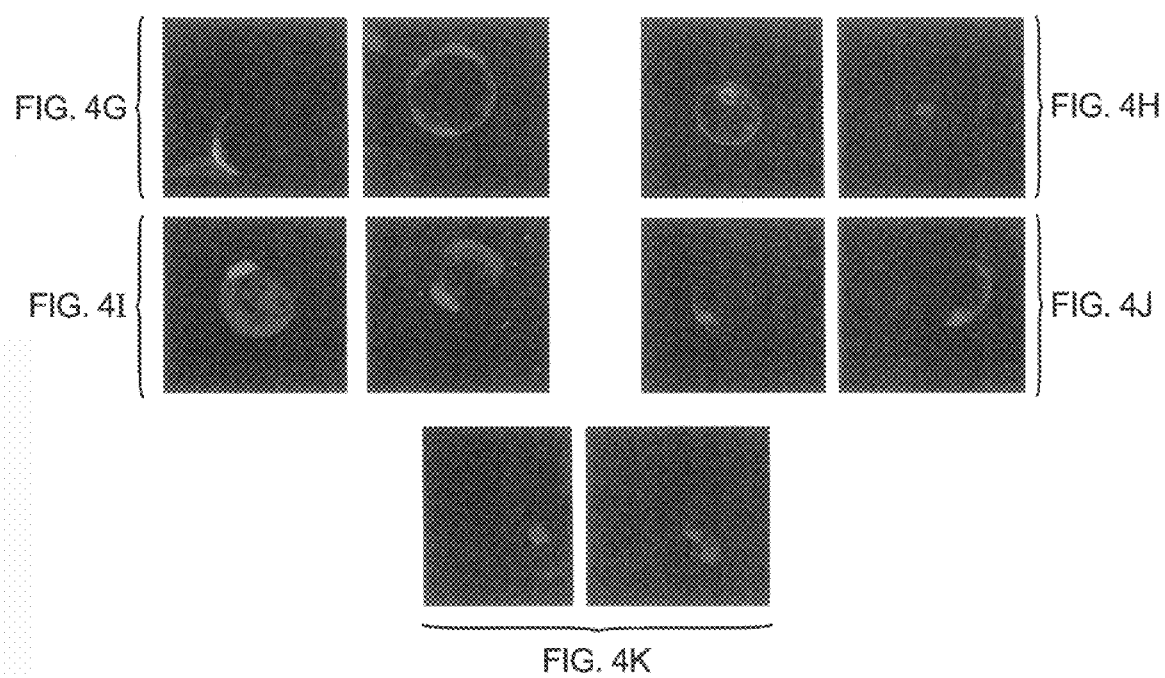

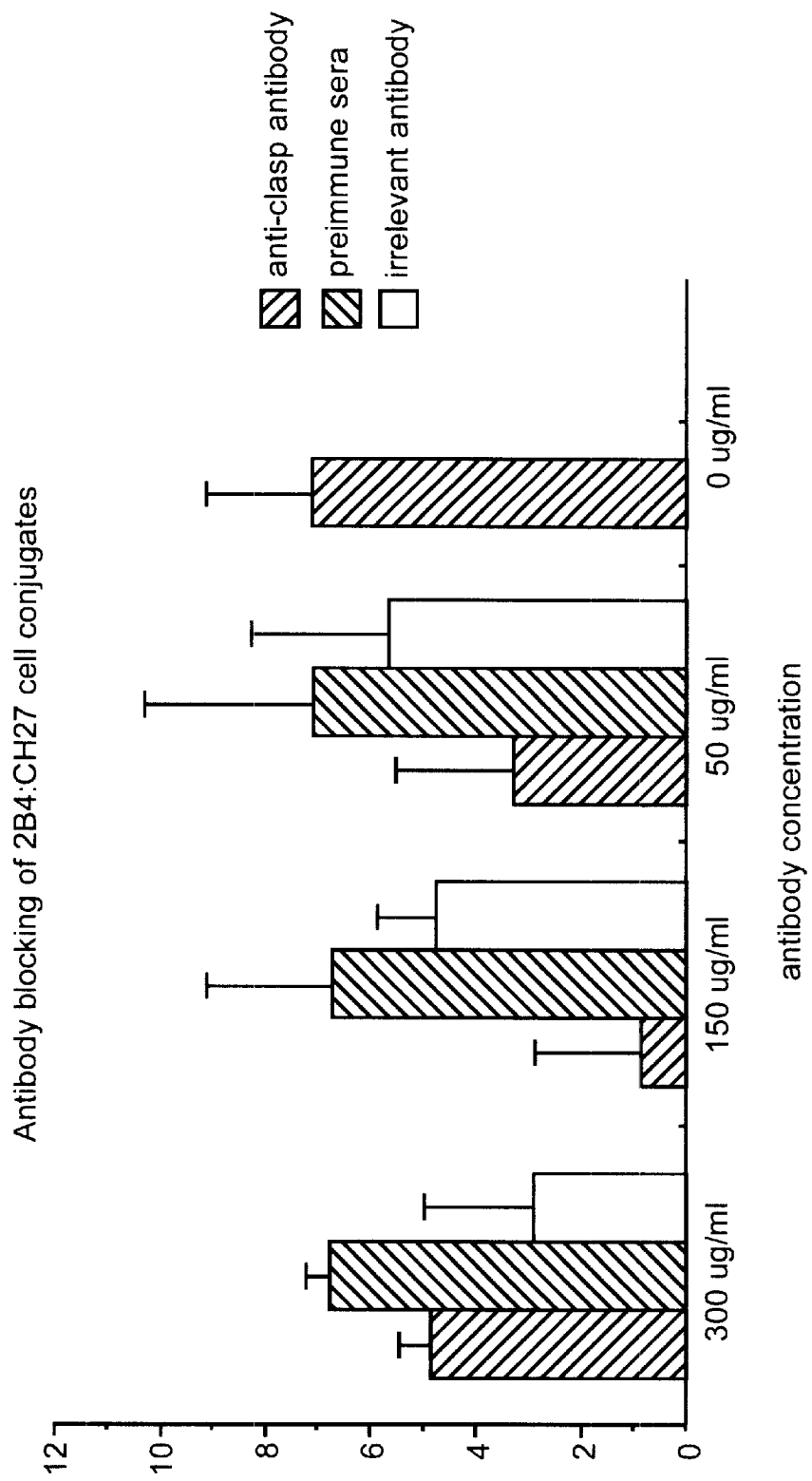

CADHERIN-LIKE ASYMMETRY PROTEIN-1, AND METHODS FOR ITS USE

CROSS-REFERENCE TO RELATED APPLICATION

This application claims priority to U.S. provisional patent application No. 60/102,964, filed Oct. 2, 1998; and is a continuation-in-part of U.S. patent application Ser. No. 09/411,328, filed Oct. 1, 1999 now abandoned.

The present invention relates to molecules involved in cell-cell interactions in the immune system. In particular, the invention relates to a cell surface protein that contains certain classical cadherin characteristics, but it exhibits an apical distribution pattern on the surface of lymphocytes. The membrane location of this molecule correlates with the contact interface between T and B cells, and antibodies against an extracellular domain of this protein disrupt T cell/B cell interactions.

BACKGROUND OF THE INVENTION

The generation of an immune response against an antigen is carried out by a number of distinct immune cell types which work in concert in the context of the particular antigen. An antigen introduced into the immune system first encounters an antigen presenting cell. An antigen presenting cell processes the antigen and presents antigenic fragments to helper T cells (TH), which, in turn, stimulate two types of immune responses; i.e., cellular and humoral immune responses. TH respond to antigen stimulation by producing lymphokines which "help" or activate other effector cell types in the immune system. TH activate B cells to secrete antibodies which function as the major effector molecule in humoral immune responses. Antibodies neutralize foreign antigens and cooperate with other effector cells in mediating antibody-dependent cellular cytotoxicity. Additionally, TH regulate cellular immune responses by stimulating another T cell subset to develop into antigen-specific cytotoxic effector cells, which directly kill antigen-expressing target cells.

TH are distinguished from cytotoxic T lymphocytes (CTL) and B cells by their expression of a cell surface glycoprotein marker termed CD4. In the mouse, type 1 helper T cells (TH1) produce interleukin-2 (IL-2) and γ-interferon (γ-IFN) upon activation by an antigen presenting cell, while type 2 helper T cells (TH2) produce IL4 and IL-5. Based on the profile of lymphokine production, TH1 appear to be involved in promoting the activation and proliferation of other T cell subsets such as CTL, whereas TH2 specifically regulate B cell proliferation and differentiation, antibody synthesis, and antibody class switching.

CTL express the CD8 surface marker. Unlike most TH, these cells display cytolytic activity by direct contact with target cells, although they are also capable of producing certain lymphokines. In vivo, these cells are particularly important in situations where an antibody response alone is inadequate. There is a preponderance of experimental evidence that cellular immune responses play a principal role in the defense against viral infections and cancer.

In the immune system, immune cells communicate with each other by direct contact via surface proteins and by secretory cytokines which bind surface receptors. In most cases, cell surface molecules are distributed evenly throughout the cell membrane. However, certain cell surface proteins have been shown to cluster after lymphocyte activation. For example, an antigenic fragment presented by an antigen presenting cell brings together the T cell receptor (TCR) and other co-receptors into a complex.

Cellular polarity reflects specialization of the cell surface membrane into domains that allow cells to assess and respond quickly to their environment (Drubin and Nelson, 1996, Cell 84: 335–44). In the immune system, migrating T lymphocytes exhibit functional polarity (Negulescu et al., 1996, Immunity 4: 421–30). Cells that encounter antigen at their leading edge readily activate, whereas those that encounter antigen at the uropod do so much more poorly.

Since TCR density does not seem to be greater at the cell's leading edge prior to antigen activation, other molecule(s) may be responsible for this intrinsic polarity. Several cytoplasmic molecules display polar distribution in lymphocytes before antigen activation. For instance, spectrin, ankyrin, and the microtubule-organizing center ("MTOC") demarcate a structural pole in T cells that has been suggested to be important in the directional delivery of signaling molecules after cell-cell coupling (Geiger et al., 1982, J. Cell Biol. 95: 13743; Gregorio et al., 1994, J. Cell Biol. 125: 345–58; Kupfer et al., 1986, J. Exp. Med. 163: 489–98; Kupfer et a., 1994, J. Exp. Med. 179:1507–15; Lee et al., 1988, Cell 55: 807–16). However, prior to the present invention, a cell surface molecule had not been identified to have a polar distribution on lymphocytes before antigen activation.

SUMMARY OF THE INVENTION

A novel mammalian cell surface molecule is provided, designated cadherin-like asymmetry protein-1 (Clasp-1). In particular, polynucleotides comprising coding sequences for Clasp-1, polynucleotides that selectively hybridize to Clasp-1 coding sequences, expression vectors containing such polynucleotides, genetically-engineered host cells containing such polynucleotides, Clasp-1 polypeptides, Clasp-1 fusion proteins, therapeutic compositions, Clasp-1 domain mutants, antibodies specific for Clasp-1, methods for detecting the expression of Clasp-1, and methods of inhibiting an immune response by interfering with Clasp-1 function. A wide variety of uses are encompassed by the invention, including but not limited to, treatment of autoimmune diseases and hypersensitivities, prevention of transplantation rejection responses, and augmentation of immune responsiveness in immunodeficiency states.

The invention is based, in part, on Applicants' discovery of Clasp-1 as a type I transmembrane protein containing certain cadherin domains and other protein domains known to be involved in signal transduction. Clasp-1 is expressed in lymphoid tissues and the brain, but is undetectable in most major adult organs. In particular, Clasp-1 is expressed in both T and B cells, as well as macrophages. The cell surface distribution pattern of Clasp-1 in lymphocytes is apical, and it is localized at the pole associated with the leading edge of the cell. More importantly, Clasp-1 is concentrated at the interface between T cell/B cell clusters, and antibodies directed to its extracellular domain inhibit T cell/B cell interactions.

BRIEF DESCRIPTION OF THE DRAWINGS

FIG. 1a: Clasp-1 amino acid sequence (SEQ ID NO:1). The 3.9 kb open reading frame (ORF) is flanked by multiple stop codons in all three reading frames and a polyadenylation signal (AATAAA) located 620 bp downstream of the translation termination codon. The sequences corresponding to the original degenerate PCR primers are marked by arrows. The propeptide extends from amino acid residues 1–120 ending in the putative cadherin processing signal RAQR (Pigott and Power, 1993, *The Adhesion Molecule Facts Book*, Academic Press Limited) (triangle). The extracellular domain contains four potential N-glycosylation sites (hexagons) and a cluster of cysteines (double underlines) before the 20 amino acid residue transmembrane domain (shade and double-underline) typical of classical cadherins (Hofman and Stoffel, 1993, Biol. Chem. Hoppe-Seyler 374: 166). The cytoplasmic domain contains a CRK-SH3 binding domain (Knudsen et al., 1994, J. Biol. Chem. 269: 32781–87) (shade and underline, residues 850–856), four cadherin sequence motifs (underlines), tyrosine phosphorylation sites (circles), and coiled/coils domains (boxes) (Lupas et al., 1991, Science 252: 1162–64). The combination of SH2/SH3 binding sites may permit interaction and regulation through adaptor proteins, and the coiled coil domains may permit direct association with the cytoskeleton.

FIG. 2: Cadherin sequence motifs. The cadherin sequence motifs are composed of four stretches of conserved cadherin amino acid sequences (A–D) which re separated by nearly identical numbers of amino acids (in parentheses). Motif A is also the CRK-SH3 binding domain and is similar to the E-cadherin sequence.

FIGS. 4a–4f: Clasp-1 localizes to the MOMA-1 marginal zone and appears to be focally distributed in T and B lymphocytes. Mice were perfusion-fixed. Their spleens were removed, cryoprotected, cryosectioned (7 micron) and probed with rabbit antiserum to Clasp-1-cyto followed by rhodamine-conjugated goat anti-rabbit (red). A second FITC stain (green) was applied to CD3 (FIGS. 4a, 4d), B220 (FIGS. 4b, 4e), or MOMA-1 (FIGS. 4c, 4f). FIGS. 4a–4c are low power views (16× objective) and FIGS. 4d–4f are high power views (63× objective). Low power views showed that anti-Clasp-1 antiserum stained cells in the peri-arteriolar lymphocyte sheath (PALS). The T cell zone, B cell zone, marginal zone, and central arterioles are labeled by T, B, M, and c respectively. In the T cell zone, staining was mostly punctate except for a few scattered cells with dendritic morphology. In the B cell zone, the dominant staining was dendritic and heavily concentrated in the marginal zone (FIG. 4e, arrow). Co-staining with macrophage markers showed localization to the MOMA-1 metallo-macrophage zone. High power views showed that Clasp-1 in T (FIG. 4d) and B (FIG. 4e) cells was organized as a "cap" associated with the plasma membrane (FIG. 4d, arrow head), or as a "ball" in the cytoplasm (FIG. 4e, arrow head). Furthermore, in T cells, the asymmetrically located Clasp-1 was concentrated at the periphery of T cell clusters as they intruded into the B cell zone (FIG. 4d, arrow head). In the MOMA-1 region, anti-Clasp-1 antiserum stained macrophage-like cells that were distinct from MOMA-1, but appeared to contact MOMA-1 macrophages (FIGS. 4e and 4f, arrow).

FIG. 4g: Clasp-1 forms an apical cap on the surface of B220 positive spleen B cells. Spleen cell suspensions were cytospun onto poly-L-lysine coated glass slides, fixed in periodate-lysine-paraformaldehyde(McLean and Nakane, 1974, J. Histochem. Cytochem. 22: 1077–83), stained with goat anti-Clasp-EC12A (plus biotin conjugated mouse monoclonal anti-goat, followed by PE-conjugated strepavidin) and anti-B220-FITC. While most B cells were Clasp-1 negative, when Clasp-1 was present, it was organized into a membrane surface apical domain.

FIG. 4h: Clasp-1 forms an apical cap or ring in CD3-positive splenic T cells. Spleen cell suspensions were cytospun onto poly-L-lysine coated glass slides, fixed in periodate-lysine-paraformaldehyde, permeabilized in CSK (Greenberg and Edelman, 1983 Cell 33: 767–79), blocked, and stained with rabbit anti-Clasp-cyto (plus rhodamine conjugated anti-rabbit Fab'2) and anti-CD3-FITC. Clasp-1 was organized into a cap or a ring.

FIG. 4i: Clasp-1 forms an apical cap on the surface of D10 T cells. D10 T cells were prepared as described under FIG. 3g above, and stained with goat anti-Clasp-EC12A (plus biotin conjugated mouse monoclonal anti-goat, followed by PE-conjugated strepavidin) and anti-CD3-FITC. Clasp-1 formed a membrane apical domain.

FIGS. 4j and 4k: Clasp-1 is located on the same side of the cell as the MTOC. D10 and 2B4 T cells were prepared as described under FIG. 4h above, and stained with rabbit anti-Clasp-cyto (plus rhodamine conjugated anti-rabbit Fab'2), monoclonal rat anti-α-tubulin (YOL 1/34, plus FITC-conjugated mouse anti-rat Fab'2), and counterstained with DAPI. The MTOC (green) was always located between the Clasp-1 surface and the nucleus.

FIG. 5a: Productive T-B cell couples were followed by T cell blast transformation (note the loss of condensed chromatin and nuclear border in the phase contrast picture of the T cells). All pairs show accumulation of Clasp-1 at the cell-cell interface.

FIG. 6a: Goat anti-Clasp-EC12 blocks T-B cell coupling. 2B4 T cell hybridoma with specificity for moth cytochrome c (MCC) in the context of I-E$^k$ was mixed with CH27 B cell loaded with MCC peptide. Gamma-bind (Pharmacia, NJ) purified goat anti-Clasp-EC12 or preimmune serum was added at 0, 50,150 and 300 μg/ml. At 150 μg/ml, goat anti-Clasp-EC12 inhibited cell conjugate formation maximally, while pre-immune serum had minimal effect even up to 450 μg/ml. More than 100 cell couples were counted per sample.

BRIEF DESCRIPTION OF THE SEQUENCE LISTING

Figure 1B:
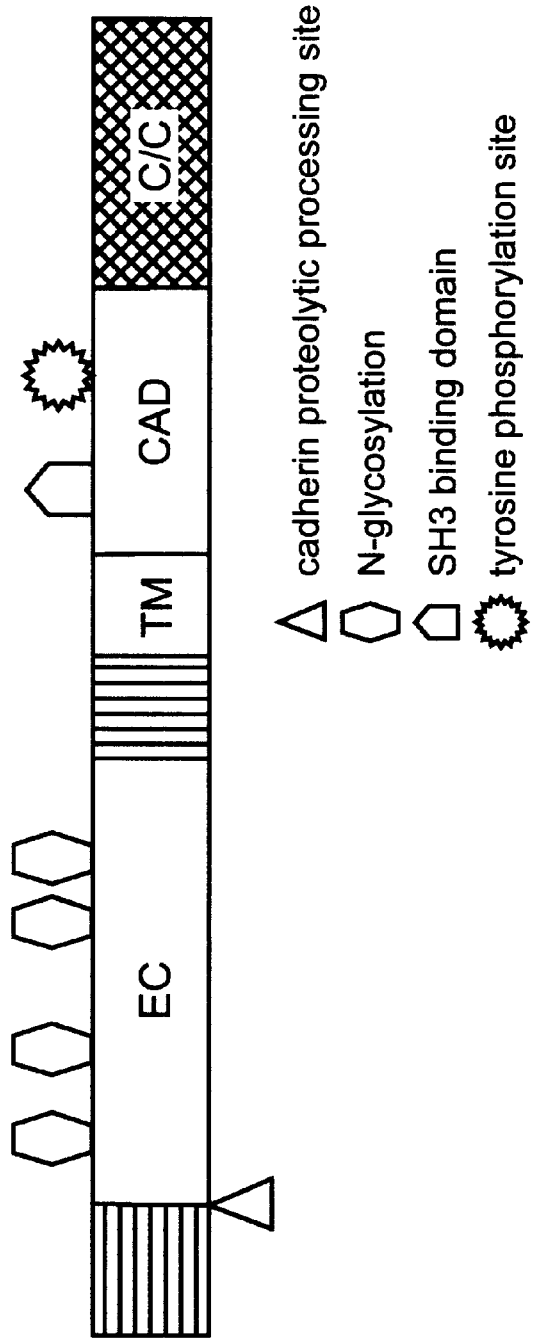
FIG. 1b: Schematic domain structure of Clasp-1. Clasp-1 contains a signal peptide (S) terminating in the cadherin proteolytic processing signal at amino acid residue #120. The extracellular domain (EC) has four glycosylation sites (hexagons) and a cluster of cysteines ("C's") typical of cadherins. The transmembrane domain (TM) is followed by a cadherin-like domain (CAD) which contains the CRK-SH3 binding domain (pentagon) and tyrosine phosphorylation sites (star), and a coiled/coil domain ("C/C").

The amino acid sequence of mouse CLASP-1 is provided as SEQ ID NO:1. The nucleotide sequence of the mouse CLASP-1 cDNA is provided in SEQ ID NO:2, which also shows the position of the start and stop of translation, and the encoded polypeptide. The nucleotide sequence of human CLASP-1 is provided as SEQ ID NO:3, with the encoded polypeptide, which is also shown in SEQ ID NO:4.

DETAILED DESCRIPTION OF THE INVENTION

Nucleic acid molecules that comprise mammalian Clasp-1 coding sequences and polypeptide encoded by the sequences are provided. In a specific embodiment by way of example, mouse and human Clasp-1 cDNA molecules were isolated, and their nucleotide and deduced amino acid sequences characterized. While Clasp-1 shares sequence homology with cadherin-encoding genes from different species, both the nucleotide coding sequences and the deduced amino acid sequences of Clasp-1 are unique.

The present invention relates to novel proteins that function in cells of the immune system, e.g. T cells and B cells, as well as non-immune cells. The CLASP-1 proteins function in a variety of cellular processes, including interactions between immune system cells. Of particular interest is the role of CLASP-1 in the activation of T cells, and in antigen presentation. CLASP-1 is believed to be involved in the organization, establishment and maintenance of the "immunological synapse" (Dustin et al. (1998) *Cell* 94:667; Dustin et al. (1996) *J. Immunol.* 157:2014).

Without being bound by a particular mechanism or limited in any way, the CLASP-1 protein is believed to be a component of the lymphocyte organelle called the "immune gateway" that creates a docking site or portal for cell-cell contact during antigen presentation. It is believed that the cytoplasmic domains organize a patch at the leading edge of T cells. When T cells engage with an antigen presenting cell, the CLASP-1 molecules engage to dock the two cells and organize the immune synapse. Data indicates that the CLASP-1 further has a role in signal transduction within T cells, although this may additional role may be not be a necessary component for its role when expressed by an antigen presenting cell.

CLASP-1 has been found to be associated with the cytoskeleton of T cells, which association is upregulated in response to activation of the T cells, e.g. antigen stimulation, pharmacologic stimulation, etc. An aspect of this cytoskeletal association is the binding of CLASP-1 to ankyrin through its C-terminus. CLASP-1 contains a number of predicted protein interaction domains in the cytoplasmic tail. Using the amino acid numbering from the mouse protein sequence (SEQ ID NO:1), these include an SH3 domain (residues 847–859); a first SH2 domain (residues 923–935); a second SH2 domain (residues 951–962); a PTB motif and third SH2 domain (residues 1035–1053); and a PTB motif (residues 1255–1269). The PTB domain (phosphotyrosine-binding)is found in cytoplasmic docking proteins (see Kavanaugh et al. (1995) Science 268(5214):1177–9). PTB domains are found primarily as components of docking proteins that recruit additional signaling proteins to the vicinity of an activated receptor.

In accordance with the invention, any nucleotide sequence that encodes an amino acid sequence of a Clasp-1 gene product can be used to generate recombinant molecules that direct the expression of Clasp-1 polypeptides.

The invention also provides isolated or purified nucleic acids consisting of at least 8 nucleotides (i.e., a hybridizable portion) of a Clasp-1 sequence or its complement; in other embodiments, the nucleic acids consist of at least 25 (continuous) nucleotides, 50 nucleotides, 100 nucleotides, 150 nucleotides, or 200 nucleotides of a Clasp-1 sequence, or a full-length Clasp-1 coding sequence. In another embodiment, the nucleic acids are smaller than 35, 200 or 500 nucleotides in length. Nucleic acids can be single or double stranded. The invention also relates to nucleic acids that selectively hybridize to or complementary to the foregoing sequences. In specific aspects, nucleic acids are provided that comprise a sequence complementary to at least 10, 25, 50, 100, or 200 nucleotides or the entire coding region of a Clasp-1 coding sequence. Such nucleotides may encode one or more of the functional domains of CLASP-1. Other nucleic acids of the invention may correspond to intron sequence of CLASP-1, which find use, for example, as probes for genomic copies, in the construction of targeting vectors, and the like.

Other CLASP-1 polynucleotides of interest encode deletion mutants, which mutants may provide a dominant negative phenotype when transfected into appropriate cells. For example, an internal cytoplasmic deletion of amino acid residues SEQ ID NO:1, 846–997, including the cadherin homology domain; or a C-terminal cytoplasmic deletion of residues SEQ ID NO:1 1011–1289; have a dominant negative phenotype in transfected T cells. Such mutations find use in mapping studies, e.g. for protein/protein interactions with CLASP-1; drug screening assays; determination of signaling pathways; and the like. T cells transfected with these dominant negative mutants had a decreased ability to be activated in response to antigenic stimulation.

The deletion mutation constructs did not have a dominant negative effect on antigen presentation, although they did not raise the antigen presenting efficiency to the extent that was found with the full length CLASP-1 coding sequence. Expression of the full-length CLASP-1 causes an increase in the ability of appropriate cells to present antigen.

In a specific embodiment, a nucleic acid is provided that hybridizes to a Clasp-1 nucleic acid (e.g., having SEQ ID NO:2, or SEQ ID NO:3) or its complement, or to a nucleic acid encoding a Clasp-1 derivative. Depending on the desired result, hybridization may be performed under condition of low, moderate or high stringency. Where it is desirable to hybridize to novel sequences, the hybridization may utilize the region of the provided sequences. For example, a nucleic acid may be determined to hybridize under stringent conditions to a probe selected from nucleotides 1 to approximately 3990 of SEQ ID NO:3.

By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

Examples of procedures using such conditions of moderate stringency are as follows: Filters containing DNA are pretreated for 6 h at 55° C. in a solution containing 6×SSC,. 5× Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

In order to clone the full length cDNA sequence from any species encoding the entire Clasp-1 cDNA, or to clone variant forms of the molecule, labeled DNA probes made from nucleic acid fragments corresponding to any partial cDNA disclosed herein may be used to screen a cDNA library derived from lymphoid cells or brain cells. More specifically, oligonucleotides corresponding to either the 5' or 3' terminus of the cDNA sequence may be used to obtain longer nucleotide sequences. Briefly, the library may be plated out to yield a maximum of 30,000 pfu for each 150 mm plate. Approximately 40 plates may be screened. The plates are incubated at 37° C. until the plaques reach a diameter of 0.25 mm or are just beginning to make contact with one another (3–8 hours). Nylon filters are placed onto the soft top agarose and after 60 seconds, the filters are peeled off and floated on a DNA denaturing solution consisting of 0.4N sodium hydroxide. The filters are then immersed in neutralizing solution consisting of 1 M Tris-HCl, pH 7.5, before being allowed to air dry. The filters are prehybridized in hybridization buffer such as casein buffer containing 10% dextran sulfate, 0.5M NaCl, 50 mM Tris-HCl, pH 7.5, 0.1% sodium pyrophosphate, 1% casein, 1% SDS, and denatured salmon sperm DNA at 0.5 mg/ml for 6 hours at 60° C. The radiolabelled probe is then denatured by heating to 95° C. for 2 minutes and then added to the prehybridization solution containing the filters. The filters are hybridized at 60° C. for 16 hours. The filters are then washed in 1× wash mix (10× wash mix contains 3M NaCl, 0.6M Tris base, and 0.02M EDTA) twice for 5 minutes each at room temperature, then in 1× wash mix containing 1% SDS at 60° C. for 30 minutes, and finally in 0.3× wash mix containing 0.1% SDS at 60° C. for 30 minutes. The filters are then air dried and exposed to x-ray film for autoradiography. After developing, the film is aligned with the filters to select a positive plaque. If a single, isolated positive plaque cannot be obtained, the agar plug containing the plaques will be removed and placed in lambda dilution buffer containing 0.1M NaCl, 0.01M magnesium sulfate, 0.035M Tris HCl, pH 7.5, 0.01% gelatin. The phage may then be replated and rescreened to obtain single, well isolated positive plaques. Positive plaques may be isolated and the CDNA clones sequenced using primers based on the known cDNA sequence. This step may be repeated until a full length cDNA is obtained.

It may be necessary to screen multiple cDNA libraries from different tissues to obtain a full length cDNA. In the event that it is difficult to identify cDNA clones encoding the complete 5' terminal coding region, an often encountered situation in cDNA cloning, the RACE (Rapid Amplification of cDNA Ends) technique may be used. RACE is a proven PCR-based strategy for amplifying the 5' end of incomplete cDNAs. 5'-RACE-Ready RNA synthesized from human tissues containing a unique anchor sequence is commercially available (Clontech). To obtain the 5' end of the cDNA, PCR is carried out on 5'-RACE-Ready cDNA using the provided anchor primer and the 3' primer. A secondary PCR reaction is then carried out using the anchored primer and a nested 3' primer according to the manufacturer's instructions. Once obtained, the full length cDNA sequence may be translated into amino acid sequence and examined for certain landmarks such as a continuous open reading frame flanked by translation initiation and termination sites, a cadherin-like domain, an SH3 binding domain, and finally overall structural similarity to the Clasp-1 gene disclosed herein.

Polypeptides Encoded by the Clasp-1 Coding Sequence

In accordance with the invention, Clasp-1 polynucleotides encode Clasp-1 polypeptides, mutant polypeptides, peptide fragments of Clasp-1 including the functional domains previously described, Clasp-1 fusion proteins or functional equivalents thereof including fusions to marker sequences such as FLAG, green fluorescent proteins, etc. as known in the art, deletion mutants which may be dominant negative mutations; etc.

Due to the inherent degeneracy of the genetic code, other DNA sequences which encode substantially the same or, a functionally equivalent amino acid sequence, may be used in the practice of the invention for the expression of the Clasp-1 protein. Such DNA sequences include those which are capable of hybridizing to the mouse Clasp-1 sequence or its complementary sequence under low, moderate or high stringent conditions as described above.

Altered DNA sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues within a Clasp-1 sequence, which result in a silent change thus producing a functionally equivalent Clasp-1 protein. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a Clasp-1 coding sequence for a variety of ends, including but not limited to, alterations which modify processing and expression of the gene product. For example, mutations may be introduced using techniques which are well known in the art, e.g., site-directed mutagenesis, deletions, to insert new restriction sites, to alter glycosylation patterns, phosphorylation, etc. Based on the domain organization of the Clasp-1 protein, a large number of Clasp-1 mutant polypeptides can be constructed by rearranging the nucleotide sequences that encode the Clasp-1 extracellular, transmembrane and cytoplasmic domains. Such mutations may have a dominant negative phenotype in certain cells.

In another embodiment of the invention, a Clasp-1 or a modified Clasp-1 sequence may be ligated to a heterologous sequence to encode a fusion protein. For example, for screening of peptide libraries for molecules that bind Clasp-1, it may be useful to produce a chimeric Clasp-1 protein expressing a heterologous epitope that is recognized by a commercially available antibody, e.g. FLAG; or may encode a detectable label, e.g. green fluorescent protein. A fusion protein may also be engineered to contain a cleavage site located between a Clasp-1 sequence and the heterologous protein sequence, so that the Clasp-1 may be cleaved away from the heterologous moiety.

Alternatively, the expression characteristics of an endogenous Clasp-1 gene within a cell population may be modified by inserting a heterologous DNA regulatory element into the genome of the cell line such that the inserted regulatory element is operatively linked with the endogenous Clasp-1 gene. For example, an endogenous Clasp-1 gene which is normally "transcriptionally silent", i.e., an Clasp-1 gene which is normally not expressed, or is expressed only at very low levels in a cell population, may be activated by inserting a regulatory element which is capable of promoting the expression of a normally expressed gene product in the cells. Alternatively, a transcriptionally silent, endogenous Clasp-1 gene may be activated by insertion of a promiscuous regulatory element that works across cell types.

A heterologous regulatory element may be inserted into a cell line population, such that it is operatively linked with an endogenous Clasp-1 gene, using techniques, such as targeted homologous recombination, which are well known to those of skill in the art, (see e.g., in Chappel, U.S. Pat. No. 5,272,071; PCT publication No. WO 91/06667, published May 16, 1991).

In an alternate embodiment of the invention, the coding sequence of Clasp-1 could be synthesized in whole or in part, using chemical methods well known in the art. (See, e.g., Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817.) Alternatively, the protein itself could be produced using chemical methods to synthesize a Clasp-1 amino acid sequence in whole or in part. For example, peptides can be synthesized by solid phase techniques, cleaved from the resin, and purified by preparative high performance liquid chromatography. (See Creighton, 1983, *Proteins Structures And Molecular Pnnciples*, W. H. Freeman and Co., N.Y. pp. 50–60). The composition of the synthetic polypeptides may be confirmed by amino acid analysis or sequencing (e.g., the Edman degradation procedure; see Creighton, 1983, *Proteins, Structures and Molecular Principles*, W. H. Freeman and Co., N.Y., pp. 34–49).

Expression Systems

In order to express a biologically active Clasp-1, the nucleotide sequence coding for Clasp-1, or a functional equivalent, is inserted into an appropriate expression vector, i.e., a vector which contains the necessary elements for the transcription and translation of the inserted coding sequence. Clasp-1 gene products as well as host cells or cell lines transfected or transformed with recombinant Clasp-1 expression vectors can be used for a variety of purposes. These include, but are not limited to, generating antibodies (i.e., monoclonal or polyclonal) that competitively inhibit activity of Clasp-1 proteins and neutralize its activity; antibodies that activate Clasp-1 function and antibodies that detect its presence on the cell surface or in solution. Anti-Clasp-1 antibodies may be used in detecting and quantifying expression of Clasp-1 levels in cells and tissues such as lymphocytes and macrophages, as well as isolating Clasp-1-positive cells from a cell mixture.

Methods which are well known to those skilled in the art can be used to construct expression vectors containing the Clasp-1 coding sequence and appropriate transcriptional/translationalcontrol signals. These methods include in vitro recombinant DNA techniques, synthetic techniques and in vivo recombination/genetic recombination. (See, e.g., the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.)

A variety of host-expression vector systems may be utilized to express the Clasp-1 coding sequence. These include, but are not limited to, microorganisms such as bacteria transformed with recombinant bacteriophage DNA, plasmid DNA, or cosmid DNA expression vectors containing the Clasp-1 coding sequence; yeast transformed with recombinant yeast expression vectors containing the Clasp-1 coding sequence; insect cell systems infected with recombinant virus expression vectors (e.g., baculovirus) containing the Clasp-1 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Clasp-1 coding sequence; or animal cell systems. The expression elements of these systems vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage γ, plac, ptrp, ptac (ptrp-lac hybrid promoter; cytomegalovirus promoter) and the like may be used; when cloning in insect cell systems, promoters such as the baculovirus polyhedron promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the Clasp-1 DNA, SV40-, BPV- and EBV-based vectors may be used with an appropriate selectable marker.

In bacterial systems a number of expression vectors may be advantageously selected depending upon the use intended for the expressed Clasp-1 product. For example, when large quantities of Clasp-1 protein are to be produced for the generation of antibodies or to screen peptide libraries, vectors which direct the expression of high levels of fusion protein products that are readily purified may be desirable. Such vectors include, but are not limited to, the E. coli expression vector pUR278 (Ruther et al., 1983, EMBO J. 2:1791), in which the Clasp-1 coding sequence may be ligated into the vector in frame with the lacZ coding region so that a hybrid protein is produced; pIN vectors (Inouye & Inouye, 1985, Nucleic acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase.(GST). In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned polypeptide of interest can be released from the GST moiety.

In yeast, a number of vectors containing constitutive or inducible promoters may be used. (Current Protocols in Molecular Biology, Vol. 2, 1988, Ed. Ausubel et al., Greene Publish. Assoc. & Wiley Interscience, Ch. 13; Grant et al., 1987, Expression and Secretion Vectors for Yeast, in Methods in Enzymology, Eds. Wu & Grossman, 1987, Acad. Press, N.Y., Vol.153, pp. 516–544; Glover, 1986, DNA Cloning, Vol. 11, IRL Press, Wash., D.C., Ch. 3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II.)

In cases where plant expression vectors are used, the expression of the Clasp-1-coding sequence may be driven by any of a number of promoters. For example, viral promoters such as the 35S RNA and 19S RNA promoters of CaMV (Brisson et al., 1984, Nature 310:511–514), or the coat protein promoter of TMV (Takamatsu et al., 1987, EMBO J. 6:307–311) may be used; alternatively, plant promoters such as the small subunit of RUBISCO (Coruzzi et al., 1984, EMBO J. 3:1671–1680; Broglie et al., 1984, Science 224:838–843); or heat shock promoters, e.g., soybean hsp17.5-E or hsp17.3-B (Gurley et al., 1986, Mol. Cell. Biol. 6:559–565) may be used. These constructs can be introduced into plant cells using Ti plasmids, Ri plasmids, plant virus vectors, direct DNA transformation, microinjection, electroporation, etc. (Weissbach & Weissbach, 1988, Methods for Plant Molecular Biology, Academic Press, NY, Section VIII, pp. 421463; and Grierson & Corey, 1988, Plant Molecular Biology, 2d Ed., Blackie, London, Ch. 7–9.)

An alternative expression system which could be used to express Clasp-1 is an insect system. In one such system, Autographa californica nuclear polyhedrosis virus (AcNPV) is used as a vector to express foreign genes. The virus grows in Spodoptera frugiperda cells. The Clasp-1 coding sequence may be cloned into non-essential regions (e.g., the polyhedron gene) of the virus and placed under control of an AcNPV promoter (e.g., the polyhedron promoter). Successful insertion of the Clasp-1 coding sequence will result in inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed. (e.g., see Smith et al., 1983, J. Viol. 46:584; Smith, U.S. Pat. No. 4,215,051).

In mammalian host cells, a number of viral based expression systems may be utilized. In cases where an adenovirus is used as an expression vector, the Clasp-1 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing Clasp-1 in infected hosts. (e.g., See Logan & Shenk, 1984, Proc. Natl. Acad. Sci. USA 81:3655–3659). Alternatively, the vaccinia 7.5K promoter may be used. (See, e.g., Mackett et al., 1982, Proc. Natl. Acad. Sci. USA 79:7415–7419; Mackett et al., 1984, J. Virol. 49:857–864; Panicali et al., 1982, Proc. Natl. Acad. Sci. USA 79:4927–4931). Regulatable expression vectors such as the tetracycline repressible vectors may also be used to express a coding sequence in a controlled fashion.

Specific initiation signals may also be required for efficient translation of inserted Clasp-1 coding sequences. These signals include the ATG initiation codon and adjacent sequences. In cases where an entire Clasp-1 gene, including its own initiation codon and adjacent sequences, is inserted into the appropriate expression vector, no additional translational control signals may be needed. However, in cases where only a portion of the Clasp-1 coding sequence is inserted, exogenous translational control signals, including the ATG initiation codon, must be provided. Furthermore, the initiation codon must be in phase with the reading frame of the Clasp-1 coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in a specific fashion desired. Such modifications (e.g., glycosylation) and processing (e.g., cleavage) of protein products may be important for the function of the protein. The presence of several consensus N-glycosylation sites in the Clasp-1 extracellulardomain support the possibility that proper modification may be important for Clasp-1 function. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, WI38, etc.

For long-term, high-yield production of recombinant proteins, stable expression is preferred. For example, cell lines which stably express Clasp-1 may be engineered. Rather than using expression vectors which contain viral origins of replication, host cells can be transformed with the Clasp-1 DNA controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched medium, and then switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the Clasp-1 protein on the cell surface. Such engineered cell lines are particularly useful in screening for molecules or drugs that affect Clasp-1 function.

A number of selection systems may be used, including but not limited to, the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase(Lowy, et al., 1980, Cell 22:817) genes which can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981), Proc. Natl. Acad. Sci. USA 78:2072); neo, which confers resistance to the aminoglycoside G418 (Colberre-Garapin, et al., 1981, J. Mol. Biol. 150:1); and hygro, which confers resistance to hygromycin (Santerre, et al., 1984, Gene 30:147). Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.) and glutamine synthetase (Bebbington et al., 1992, Biotech 10: 169).

Identification of Cells That Express Clasp-1

The host cells which contain the coding sequence and which express a biologically active Clasp-1 gene product or fragments thereof may be identified by at least four general approaches; (a) DNA-DNA or DNA-RNA hybridization; (b) the presence or absence of "marker" gene functions; (c) assessing the level of transcription as measured by the expression of Clasp-1 mRNA transcripts in the host cell; and (d) detection of the gene product as measured by immunoassay or by its biological activity. Prior to the identification of gene expression, the host cells may be first mutagenized in an effort to increase the level of expression of Clasp-1, especially in cell lines that produce low amounts of Clasp-1.

In the first approach, the presence of the Clasp-1 coding sequence inserted in the expression vector can be detected by DNA-DNA or DNA-RNA hybridization using probes comprising nucleotide sequences that are homologous to the Clasp-1 coding sequence, respectively, or portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the Clasp-1 coding sequence is inserted within a marker gene sequence of the vector, recombinants containing the Clasp-1 coding sequence can be identified by the absence of the marker gene function. Alternatively, a marker gene can be placed in tandem with the Clasp-1 sequence under the control of the same or different promoter used to control the expression of the Clasp-1 coding sequence. Expression of the marker in response to induction or selection indicates expression of the Clasp-1 coding sequence.

In the third approach, transcriptional activity for the Clasp-1 coding region can be assessed by hybridization assays. For example, RNA can be isolated and analyzed by Northern blot using a probe homologous to the Clasp-1 coding sequence or particular. portions thereof. Alternatively, total nucleic acids of the host cell may be extracted and assayed for hybridization to such probes. Additionally, reverse transcription-polymerase chain reactions may be used to detect low levels of gene expression.

In the fourth approach, the expression of the Clasp-1 protein product can be assessed immunologically, for example by Western blots, immunoassays such as radioimmuno-precipitation, enzyme-linked immunoassays and the like. This can be achieved by using an anti-Clasp-1 antibody. Alternatively, Clasp-1 protein may be expressed as a fusion protein with green-fluorescent protein to facilitate its detection in cells (U.S. Pat. Nos. 5,491,084; 5,804,387; 5,777,079).

Uses of Clasp-1 Engineered Host Cells

In one embodiment of the invention, the Clasp-1 protein and/or cell lines that express Clasp-1 may be used to screen for antibodies, peptides, small molecules, natural and synthetic compounds or other cell bound or soluble molecules that bind to the Clasp-1 protein resulting in stimulation or inhibition of Clasp-1 function. For example, anti-Clasp-1 antibodies may be used to inhibit or stimulate Clasp-1 function and to detect its presence. Alternatively, screening of peptide libraries with recombinantly expressed soluble Clasp-1 protein or cell lines expressing Clasp-1 protein may be useful for identification of therapeutic molecules that function by inhibiting or stimulating the biological activity of Clasp-1. The uses of the Clasp-1 protein and engineered cell lines, described in the subsections below, may be employed equally well for homologous Clasp-1 genes in various species.

In a specific embodiment of the invention, cell lines have been engineered to express the extracellular domain of Clasp-1 fused to another molecule such as GST. In addition, Clasp-1 or its extracellular domain may be fused to an immunoglobulin constant region (Hollenbaugh and Aruffo, 1992, Current Protocols in Immunology, Unit 10.19; Aruffo et al., 1990,. Cell 61:1303) to produce a soluble molecule with increased half life. The soluble protein or fusion protein may be used in binding assays, affinity chromatography, immunoprecipitation, Western blot, and the like. Synthetic compounds, natural products, and other sources of potentially biologically active materials can be screened in assays that are well known in the art.

Random peptide libraries consisting of all possible combinations of amino acids attached to a solid phase support may be used to identify peptides that are able to bind to a specific domain of Clasp-1 (Lam, K. S. et al., 1991, Nature 354: 82–84). The screening of peptide libraries may have therapeutic value in the discovery of pharmaceutical agents that stimulate or inhibit the biological activity of Clasp-1.

Identification of molecules that are able to bind to the Clasp-1 protein may be accomplished by screening a peptide library with recombinant soluble Clasp-1 protein. Methods for expression and purification of Clasp-1 may be used to express recombinant full length Clasp-1 or fragments of Clasp-1 depending on the functional domains of interest. Such domains include Clasp-1 extracellular domain, transmembrane domain, cytoplasmic domain, SH2 domain, SH3 domain and coiled/coil domain. In a specific embodiment, a portion of the Clasp-1 extracellular domain corresponding to amino acid residues #131–327 is shown to contain a binding site that interacts with itself or other proteins.

To identify and isolate the peptide/solid phase support that interacts and forms a complex with Clasp-1, it is necessary to label or "tag" the Clasp-1 molecule. The Clasp-1 protein may be conjugated to enzymes such as alkaline phosphatase or horseradish peroxidase or to other reagents such as fluorescent labels which may include fluorescein isothiocyanate (FITC), phycoerythrin (PE) or rhodamine. Conjugation of any given label to Clasp-1 may be performed using techniques that are well known in the art. Alternatively, Clasp-1 expression vectors may be engineered to express a chimeric Clasp-1 protein containing an epitope for which a commercially available antibody exist. The epitope-specific antibody may be tagged with a detectable label using methods well known in the art including an enzyme, a fluorescent dye or colored or magnetic beads.

The "tagged" Clasp-1 conjugate is incubated with the random peptide library for minutes to one hour at 22° C. to allow complex formation between Clasp-1 and peptide species within the library. The library is then washed to remove any unbound protein. If Clasp-1 has been conjugated to alkaline phosphatase or horseradish peroxidase the whole library is poured into a petri dish containing substrates for either alkaline phosphatase or peroxidase, for example, 5-bromo4-chloro-3-indoylphosphate (BCIP) or 3,3',4,4"-diaminobenzidine (DAB), respectively. After incubating for several minutes, the peptide/solid phase-Clasp-1 complex changes color, and can be easily identified and isolated physically under a dissecting microscope with a micromanipulator. If a fluorescenttagged Clasp-1 molecule has been used, complexes may be isolated by fluorescence activated sorting. If a chimeric Clasp-1 protein expressing a heterologous epitope has been used, detection of the peptide/Clasp-1 complex may be accomplished by using a labeled epitope-specific antibody. Once isolated, the identity of the peptide attached to the solid phase support may be determined by peptide sequencing.

In addition to using soluble Clasp-1 molecules, in another embodiment, it is possible to detect peptides that bind to cell-associated Clasp-1 using intact cells. The use of intact cells is preferred for use with cell surface molecules. Methods for generating cell lines expressing Clasp-1 are described above. The cells used in this technique may be either live or fixed cells. The cells may be incubated with the random peptide library and bind to certain peptides in the library to form a "rosette" between the target cells and the relevant solid phase support/peptide. The rosette can thereafter be isolated by differential centrifugation or removed physically under a dissecting microscope. Techniques for screening combinatorial libraries are known in the art (Gallop et al., 1994, J. Med. Chem., 37:1233; Gordon, 1994, J. Med. Chem., 37:1385).

As an alternative to whole cell assays for membrane bound receptors or receptors that require the lipid domain of the cell membrane to be functional, Clasp-1 molecules can be reconstituted into liposomes where label or "tag" can be attached.

Anti-Clasp-1 Antibodies

Various procedures known in the art may be used for the production of antibodies to epitopes of the natural and recombinantly produced Clasp-1 protein. Such antibodies include, but are not limited to, polyclonal, monoclonal, chimeric, single chain, humanized, a complementarity determining region, Fab fragments, F(ab')$_2$ and fragments produced by an Fab expression library as well as anti-idiotypic antibodies. Antibodies that compete for Clasp-1 binding are especially preferred for diagnostics and therapeutics.

To mount an antibody response, a peptide must contain both a T and B cell epitope. A T cell epitope binds an MHC class II molecule and be recognized by an existing T cell receptor (TCR). Additional amino acid sequence is needed for the B cell epitope. Generally a peptide of about 15–20 amino acids satisfies both of these requirements. Alternatively one may conjugate a peptide with another protein which is known to be immunogenic, for example bovine serum albumin (BSA), keyhole limpet hemocyanin (KLH) or ovalbumin (OVA). For antibody recognition, N-terminal (and in the case of soluble proteins, C-terminal) regions of the protein are often more easily accessible to antibody binding. In addition to the hydrophilic residues needed for MHC Class II binding, hydrophilic sequences are more likely to be accessible to antibody recognition.

Monoclonal antibodies that bind Clasp-1 may be radioactively labeled allowing one to follow their location and distribution in the body after injection. Radioisotope tagged antibodies may be used as a non-invasive diagnostic tool for imaging de novo lymphoid tumors and metastases that express Clasp-1.

Immunotoxins may also be designed which target cytotoxic agents to specific sites in the body. For example, high affinity Clasp-1 specific monoclonal antibodies may be covalently complexed to bacterial or plant toxins, such as diphtheria toxin or ricin. A general method of preparation of antibody/hybrid molecules may involve use of thiol-crosslinking reagents such as SPDP, which attack the primary amino groups on the antibody and by disulfide exchange, attach the toxin to the antibody. The hybrid antibodies may be used to specifically eliminate Clasp-1 expressing lymphocytes.

For the production of antibodies, various host animals may be immunized by injection with the recombinant or naturally purified Clasp-1 protein, fusion protein or peptides, including but not limited to goats, rabbits, mice, rats, hamsters, etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and *Corynebacterium parvum*.

Monoclonal antibodies to Clasp-1 may be prepared by using any technique which provides for the production of antibody molecules by continuous cell lines in culture. These include, but are not limited to, the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci. USA, 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al.,1984, Proc. Natl. Acad. Sci. USA, 81:6851–6855; Neubergeretal., 1984, Nature, 312:604–608; Takeda et al., 1985, Nature, 314:452454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce Clasp-1-specific single chain antibodies.

Hybridomas may be screened using enzyme-linked immunosorbent assays (ELISA) in order to detect cultures secreting antibodies specific for refolded recombinant Clasp-1. Cultures may also be screened by ELISA to identify those cultures secreting antibodies specific for mammalian-produced Clasp-1. Confirmation of antibody specificity may be obtained by western blot using the same antigens. Subsequent ELISA testing may use recombinant Clasp-1 fragments to identify the specific portion of the Clasp-1 molecule with which a monoclonal antibody binds. Additional testing may be used to identify monoclonal antibodies with desired functional characteristics such as staining of histological sections, immunoprecipitation of Clasp-1, inhibition of Clasp-1 binding or stimulation of Clasp-1 to transmit an intracellular signal. Determination of the monoclonal antibody isotype may be accomplished by ELISA, thus providing additional information concerning purification or function.

Antibody fragments which contain specific binding sites of Clasp-1 may be generated by known techniques. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity to Clasp-1. Anti-Clasp-1 antibodies may be used to identify, isolate, inhibit or eliminate Clasp-1-expressing cells.

Uses of Clasp-1 Polynucleotide

A Clasp-1 polynucleotide or fragments thereof may be used for diagnostic and/or therapeutic purposes. In particular, since Clasp-1 is expressed in lymphocytes, a Clasp-1 polynucleotide may be used to detect the expression of Clasp-1 as a lymphocyte marker. For diagnostic purposes, a Clasp-1 polynucleotide may be used to detect Clasp-1 gene expression or aberrant Clasp-1 gene expression in disease states. Included in the scope of the invention are oligonucleotide sequences, such as antisense RNA and DNA molecules and ribozymes, that function to inhibit expression of Clasp-1. Clasp-1 polynucleotide may be used to construct transgenic and knockout animals for screening of Clasp-1 agonists and antagonists.

Transgenic and Knockout Animal

The Clasp-1 gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate Clasp-1 transgenic animals. The term "transgenic," as used herein, refers to animals expressing Clasp-1 gene sequences from a different species (e.g., mice expressing human Clasp-1 gene sequences), as well as animals that have been genetically engineered to overexpress endogenous (i.e., same species) Clasp-1 sequences or animals that have been genetically engineered to no longer express endogenous Clasp-1 gene sequences (i.e., "knock-out" animals), and their progeny.

Any technique known in the art may be used to introduce a Clasp-1 transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82:6148–6152); gene targeting in embryonic stem cells (Thompson, et al., 1989, Cell 56:313–321); electroporation of embryos (Lo, 1983, Mol. Cell. Biol. 3:1803–1814); and sperm-mediated gene transfer (Lavitrano et al., 1989, Cell 57:717–723) (For a review of such techniques, see Gordon, 1989, Transgenic Animals, Intl. Rev. Cytol. 115, 171–229)

Any technique known in the art may be used to produce transgenic animal clones containing a Clasp-1 transgene, for example, nuclear transfer into enucleated oocytes of nuclei from cultured embryonic, fetal or adult cells induced to quiescence (Campbell, et al., 1996, Nature 380:64–66; Wilmut, et al., Nature 385:810–813).

The present invention provides for transgenic animals that carry a Clasp-1 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89:6232–6236). The regulatory sequences required for such a cell-type specific activation will depend upon the particular cell type of interest, and will be apparent to those of skill in the art. When it is desired that the Clasp-1 transgene be integrated into the chromosomal site of the endogenous Clasp-1 gene, gene targeting is preferred. Briefly, when such a technique is to be utilized, vectors containing some nucleotide sequences homologous to the endogenous Clasp-1 gene, which sequences may include intron sequences of Clasp-1, are designed for the purpose of integrating, via homologous recombination with chromosomal sequences, into and disrupting the function of the nucleotide sequence of the endogenous Clasp-1 gene. The transgene may also be selectively introduced into a particular cell type, thus inactivating the endogenous Clasp-1 gene in only that cell type, by following, for example, the teaching of Gu, et al. (1994, Science 265: 103–106). The regulatory sequences required for such a cell-type specific inactivation will depend upon the particular cell type of interest, and will be apparent to those of skill in the art.

Once transgenic animals have been generated, the expression of the recombinant Clasp-1 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR (reverse transcriptase PCR). Samples of Clasp-1 geneexpressing tissue, may also be evaluated immunocytochemically using antibodies specific for the Clasp-1 transgene product.

Diagnostic Uses of Clasp-1 Polynucleotide

A Clasp-1 polynucleotide may have a number of uses in the diagnosis of diseases or disorders resulting from aberrant expression of Clasp-1 such as immunodeficient states. For example, the Clasp-1 DNA sequence may be used in hybridization assays of biopsies or autopsies to detect abnormalities of Clasp-1 expression; e.g., Southern or Northern analysis, including in situ hybridization assays and PCR. In that connection, PCR primers of 15–30 nucleotides may be used. A preferred length of a PCR primer is about 18–22 nucleotides. However, the length of primers may be adjusted by one skilled in the art. With respect to a Clasp-1 probe, a polynucleotide of 300–500 nucleotides is preferred. Various hybridization techniques are well known in the art, and are in fact the basis of many commercially available diagnostic kits.

Therapeutic Uses of Clasp-1 Polynucleotide

A Clasp-1 polynucleotide may be useful in the treatment of various abnormal conditions. By introducing gene sequences into cells, gene therapy can be used to treat conditions in which the cells do not express normal Clasp-1 or express abnormal/inactive Clasp-1. In some instances, the polynucleotide encoding a Clasp-1 is intended to replace or act in the place of a functionally deficient endogenous gene. Alternatively, abnormal conditions characterized by pverexpression can be treated using the gene therapy techniques described below.

In a specific embodiment, nucleic acids comprising a sequence encoding a Clasp-1 protein or functional derivative thereof, are administered to promote Clasp-1 function, by way of gene therapy. Gene therapy refers to therapy performed by the administration of a nucleic acid to a subject. In this embodiment of the invention, the nucleic acid produces its encoded protein that mediates a therapeutic effect by promoting Clasp-1 function.

Any of the methods for gene therapy available in the art can be used according to the present invention. Exemplary methods are described below.

For general reviews of the methods of gene therapy, see Goldspiel et al., 1993, Clinical Pharmacy 12:488–505; Wu and Wu, 1991, Biotherapy 3:87–95; Tolstoshev, 1993, Ann. Rev. Pharmacol. Toxicol. 32:573–596; Mulligan, 1993, Science 260:926–932; and Morgan and Anderson, 1993, Ann. Rev. Biochem. 62:191–217; May, 1993, TIBTECH 11(5):155–215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In a preferred aspect, the therapeutic composition comprises a Clasp-1 nucleic acid that is part of an expression vector that encodes a Clasp-1 protein or fragment or chimeric protein thereof in a suitable host. In particular, such a nucleic acid has a promoter operably linked to the Clasp-1 coding region, said promoter being inducible or constitutive, and, optionally, tissue-specific. In another particular embodiment, a nucleic acid molecule is used in which the Clasp-1 coding sequences and any other desired sequences are flanked by regions that promote homologous recombination at a desired site in the genome, thus providing for intrachromosomal expression of the Clasp-1 nucleic acid (Koller and Smithies, 1989, Proc. Natl. Acad. Sci. USA 86:8932–8935; Zijlstra et al., 1989, Nature 342:435438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, 1987, J. Biol. Chem. 262:44294432) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16,1992; WO 92/22635 dated Dec. 23, 1992; WO92/20316 dated Nov. 26, 1992; WO93/14188 dated Jul. 22, 1993; WO 93/20221 dated Oct. 14, 1993). Alternatively, the nucleic acid can be introduced intracellularly and incorporated within host cell DNA for expression, by homologous recombination (Koller and Smithies, 1989, Proc. Natl. Acad. Sci. USA 86:8932–8935; Zijlstra et al., 1989, Nature 342:435438).

In a specific embodiment, a viral vector that contains the Clasp-1 nucleic acid is used. For example, a retroviral vector can be used (see Miller et al., 1993, Meth. Enzymol. 217:581–599). These retroviral vectors have been modified to delete retroviral sequences that are not necessary for packaging of the viral genome and integration into host cell DNA. The Clasp-1 nucleic acid to be used in gene therapy is cloned into the vector, which facilitates delivery of the gene into a patient. More detail about retroviral vectors can be found in Boesen et al., 1994, Biotherapy 6:291–302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644–651; Kiem et al., 1994, Blood 83:1467–1473; Salmons and Gunzberg, 1993, Human Gene Therapy 4:129–141; and Grossman and Wilson, 1993, Curr. Opin. in Genetics and Devel. 3:110–114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson (1993, Current Opinion in Genetics and Development 3:499–503) present a review of adenovirus-based gene therapy. Bout et al., (1994, Human Gene Therapy 5:3–10) demonstrated the use of adenovirus vectors to transfer genes to the respiratory epithelia of rhesus monkeys. Other instances of the use of adenoviruses in gene therapy can be found in Rosenfeld et al., 1991, Science 252:431–434; Rosenfeld et al., 1992, Cell 68:143–155; and Mastrangeli et al., 1993, J. Clin. Invest. 91:225–234. Adeno-associated virus (AAV) has also been proposed for use in gene therapy (Walsh et al., 1993, Proc. Soc. Exp. Biol. Med. 204:289–300.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, 1993, Meth. Enzymol. 217:599–618; Cohen et al., 1993, Meth. Enzymol. 217:618–644; Cline, 1985, Pharmac. Ther. 29:69–92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc. In a preferred embodiment, the cell used for gene therapy is autologous to the patient.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Oligonucleotide sequences, that include anti-sense RNA and DNA molecules and ribozymes that function to inhibit the translation of a Clasp-1 mRNA are within the scope of the invention. Such molecules are useful in cases where downregulation of Clasp-1 expression is desired. Anti-sense RNA and DNA molecules act to directly block the translation of mRNA by binding to targeted mRNA and preventing protein translation. In regard to antisense DNA, oligodeoxyribonucleotides derived from the translation initiation site, e.g., between −10 and +10 regions of a Clasp-1 nucleotide sequence, are preferred.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Within the scope of the invention are engineered hammerhead motif ribozyme molecules that specifically and efficiently catalyze endonucleolytic cleavage of Clasp-1 RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such as secondary structure that may render the oligonucleotide sequence unsuitable. The suitability of candidate targets may also be evaluated by testing their accessibility to hybridization with complementary oligonucleotides, using ribonuclease protection assays.

Endogenous target gene expression can also be reduced by inactivating or "knocking out" the target gene or its promoter using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, With or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi,. 1987 and Thompson, 1989, supra). However, this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one'strand of a duplex. Nucleotide sequences may be pyrimidine-based, which will result in TAT and CGC triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

The anti-sense RNA and DNA molecules, ribozymes and triple helix molecules of the invention may be prepared by any method known in the art for the synthesis of RNA molecules. These include techniques for chemically 'synthesizing oligodeoxyri-bonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which contain suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various modifications to the DNA molecules may be introduced as a means of increasing intracellular stability and half-life. Possible modifications include, but are not limited to, the addition of flanking sequences of ribo- or deoxy- nucleotides to the 5'and/or 3' ends of the molecule or the use of phosphorothioate or 2'O-methyl rather than phosphodiesterase linkages within the oligodeoxyribonucleotide backbone.

Methods for introducing polynucleotides into such cells or tissue include methods for in vitro introduction of polynucleotides such as the insertion of naked polynucleotide, i.e., by injection into tissue, the introduction of a Clasp-1 polynucleotide in a cell ex vivo, the use of a vector such as a virus, (retrovirus, adenovirus, adeno-associated virus, etc.), phage or plasmid, etc. or techniques such as electroporation or calcium phosphate precipitation.

Uses of Clasp-1 Protein

The subject gene may be employed for producing all or portions of Clasp-1 polypeptides. Fragments of interest include glycosylation sites, which may affect the stability and/or activity of the polypeptide, the protein interaction sites, etc. Such domains will usually include at least about 20 amino acids of the provided sequence, more usually at least about 50 amino acids, and may include 100 amino acids or more, up to the complete domain. Binding contacts may be comprised of non-contiguous sequences, which are brought into proximity by the tertiary structure of the protein. The sequence of such fragments may be modified through manipulation of the coding sequence, as described above. Truncations may be performed at the carboxy or amino terminus of the fragment, e.g. to determine the minimum sequence required for biological activity.

A polypeptide of particular interest comprises the mature portion of the Clasp-1 protein, i.e. the fragment that remain after cleavage of the signal peptide, or the propeptide sequence. Determination of this cleavage site may be determined experimentally, by producing the polypeptide in an expression system capable such cleavage, and then determining the terminus of the mature protein. Alternatively, the cleavage site may be determined by deduction, after comparison with known cleavage sites. For example, the cleavage site of the mouse Clasp-1 polypeptide is between residue 120 and 121. In the human homolog, a putative cleavage site (arg pro gin arg) is between residues 104 and 105.

Assays for the biological activity of the protein or fragments thereof may be determined as described in the art. Numerous in vitro assays for determining lymphocyte activation are known in the art, or as provided in the Examples. Inhibition of cellular adhesion and cell-cell contacts, is determined through in vivo or in vitro models (for reviews, see Fukuda (1995) *Bioorg Med Chem* 3(3):207–215; Zanetta et al. (1994) *Histol Histopathol* 9(2):385412).

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The Clasp-1 protein is expressed in lymphocytes, and is specifically localized at the interface of T cell-B cell interactions. Therefore, a soluble Clasp-1, a Clasp-1 fragment containing an extracellular domain or an anti-Clasp-1 antibody may be used to inhibit T cell-B cell interactions, thereby inhibiting an immune response. It is believed that the involvement of Clasp-1 in T cell-B cell contact occurs prior to B cell activation by the T$_H$, thus inhibition of Clasp-1 binding can interfere with an early stage of the immune response. Autoimmune disorders that may be treated by disrupting Clasp-1 function, include, but are not limited to, multiple sclerosis, juvenile diabetes, rheumatoid arthritis, pemphigus, pemphigoid, epidermolysis bullosa acquista, lupus, Rh incompatibility, etc.

Additionally, since Clasp-1 contains domains capable of transducing an intracellular signal, cell surface Clasp-1 may be triggered by an anti-Clasp-1 antibody or soluble Clasp-1 or a fragment thereof in order to enhance the activation state of a lymphocyte.

Formulation and Route of Administration

A Clasp-1 polypeptide, a fragment thereof or an anti-Clasp-1 antibody may be administered to a subject per se or in the form of a pharmaceutical or therapeutic composition. Pharmaceutical compositions comprising the proteins of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the protein or active peptides into preparations which can be used pharmaceutically. Proper formulation is dependent upon the route of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, oral or pulmonary administration.

For injection, the proteins of the invention may be formulated in aqueous solutions, preferably in physiologically compatible buffers such as Hanks's solution; Ringer's solution, or physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, a composition can be readily formulated by combining the proteins with pharmaceutically acceptable carriers well known in the art. Such carriers enable the proteins to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The proteins may also be formulated in rectal or vaginal compositions such as suppositories or retention enemas, e.g, containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the proteins or peptides of the invention. Certain organic solvents such as dimethylsulfoxide also may be employed, although usually at the cost of greater toxicity. Additionally, the proteins may be delivered using a sustained-release system, such as semipermeable matrices of solid polymers containing the therapeutic agent. Various sustained-release materials have been established and are well known by those skilled in the art. Sustained-release capsules may, depending on their chemical nature, release the proteins for a few weeks up to over 100 days. Depending on the chemical nature and the biological stability of the therapeutic reagent, additional strategies for protein stabilization may be employed.

As the proteins and peptides of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

Effective Dosages

Clasp-1 polypeptides, Clasp-1 fragments and anti-Clasp-1 antibodies will generally be used in an amount effective to achieve the intended purpose. For use to inhibit an immune response, the proteins of the invention, or pharmaceutical compositions thereof, are administered or applied in a therapeutically effective amount. By therapeutically effective amount is meant an amount effective ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that inhibits 50% of Clasp-1 binding interactions). Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the proteins which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation. The amount of Clasp-1 administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with Clasp-1 or fragments thereof include, but are not limited to, steroid and non-steroid immunosuppressive agents.

Toxicity

Preferably, a therapeutically effective dose of the proteins described herein will provide therapeutic benefit without causing substantial toxicity. Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch. 1, p.1).

Screening Assays

In vitro studies may use purified Clasp-1 macromolecules to screen large compound libraries for inhibitory drugs; or the purified target molecule may be used for a rational drug design program, which requires first determining the structure of the target or, the structure of the macromolecular target in association with its customary substrate or ligand. This information is then used to design inhibitory compounds which must be synthesized and tested further. Test results are used to refine the molecular models and drug design process in an iterative fashion until a lead compound emerges.

Drug screening may be performed using an in vitro model, a genetically altered cell, or purified protein, including the use of mutant proteins, such as those provided herein. One can identify ligands or substrates that bind to, modulate or mimic the action of the target genetic sequence or its product. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions.

The term "agent" as used herein describes any molecule, e.g. protein or pharmaceutical, with the capability of altering or mimicking the physiological function of RAB. Generally a plurality of assay mixtures are run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries. of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired biological activity may be administered in a an acceptable carrier to a host for treatment of fungal infection, or prevention of infection, etc. The inhibitory agents may be administered in a variety of ways. Depending upon the manner of introduction, the compounds may be formulated in a variety of ways. The concentration of therapeutically active compound in the formulation may vary from about 0.01–100 wt. %.

The invention having been described, the following examples are offered by way of illustration and not limitation.

EXPERIMENTAL

Example 1 cDNA Cloning of CLASP-1

Degenerate oligonucleotide primers were designed on the basis of a highly conserved cytoplasmic domain of classical cadherins corresponding to sequences TAPPYD and FKKLAD. The 5' sense primer had the sequence of GGMTTCCACNGCNCCNCCNTA(CT)GA(SEQ ID NO:5) and the 3' anti-sense primer had the sequence of GCTCTAGATCNGCNA(AG)(CT)TT(CT)TT(AG)M(SEQ ID NO:6).

Total RNA was prepared from mouse thymocytes according to the method of Chomczynski and Sacchi (1987, Anal. Biochem. 162: 156–59), and the RNA was primed with oligo dT and reverse transcribed with MMTV reverse transcriptase (BRL, NY) according to the method of Suzuki et al., (1988, Cell Regul. 2: 807–16). The CDNA was then used for hot start (Ampli-wax, Perkin Elmer, CA) Polymerase Chain Reaction (PCR) in Promega PCR buffer (Promega, WI) containing Mg (1.5–3.0 mM), 1 µg primer each, 2.5 units of AmpliTaq (Perkin Elmer, CA). The Perkin Elmer Thermocycler (Perkin Elmer, CA) was set to 94° C. for a 30 second denaturation, 37° C. for a 2 minute annealing, and ramped over 2 minutes to 65° C., which was maintained for a 3 minute extension reaction, for 35 cycles. The PCR products were resolved in 3% NuSieve agarose (FMC, ME): 1% agarose (BRL, NY). The band of predicted size was excised, purified using Sephaglas (Pharmacia, NJ), and reamplified for 20 rounds using the same program.

The final product was gel purified, digested with EcoR1 and Xba1 (New England Biolabs, MA), and cloned into pBluescript KS (Stratagene, La Jolla, Calif.) at the corresponding sites, and its nucleotide sequence determined. Half of the PCR clones sequenced were identical. A representative clone was used to screen a mouse neonatal thymus library to obtain a complete cDNA sequence designated Clasp-1.

Results

Degenerate oligonucleotides corresponding to consensus sequences of cadherins and other adhesion molecule families were made for use in PCR of cDNA prepared from mouse thymocytes. In addition to several classical cadherin molecules, a sequence that accounted for half of the clones and displayed several features of classical cadherins was isolated (FIGS. 1a–1b). The full length cDNA clone (SEQ ID NO:2) contains an open reading frame that encodes a 1,289 amino acid type I transmembrane protein which shares a number of cadherin features, including the cadherin proteolytic processing signal (Pigott and Power, 1993, *The Adhesion Molecule Facts Book*, Academic Press Limited), glycosylation sites, a cluster of cysteines proximal to the transmembrane domain (Hofman and Stoffel, 1993, Biol. Chem. Hoppe-Seyler 374: 166), and a cytoplasmic domain that exhibits several cadherin sequence motifs (FIG. 2). The processed polypeptide begins at amino acid residue #121 after the amino acid sequence RAQR (FIG. 1a). This gene was named Clasp-1 for cadherin-like asymmetry protein.

Classical cadherins are transmembrane glycoproteins that mediate homotypic calcium-dependent adhesion through their extracellular domains and connect with the cytoskeleton via catenins through their cytoplasmic domains (Kemler, 1993, Trends Genet. 9: 317–21; Geiger and Ayalon, 1992, Annu. Rev. Cell Biol. 8: 307–32; Takeichi, 1991, Science 251: 1451–55). Unique features of Clasp-1 which are not shared with cadherins include an SH3 binding domain (Knudsen et al., 1994, J. Biol. Chem. 269: 32781–87), several potential tyrosine phosphorylation sites, and coiled/coil domains (Lupas et al., 1991, Science 252: 1162–64) (FIGS. 1a and 1b). Based on its structural characteristics, Clasp-1 may provide a direct interaction between signal transduction pathways and the cytoskeleton. FASTA searches of Clasp-1 (Pearson and Lipman, 1988, Proc. Natl. Acad. Sci. USA 85: 2444–48; Ladunga et al., 1996, J. Mol. Biol. 259: 840–54) revealed similarities with two cDNAs of unknown function, the rat RNTRG (GenBank X68101) and a putative *C. elegans* gene, CELF46fH5.4 (GenBank U41543). RNTRG is about 75% identical to Clasp-1. Therefore, Clasp-1 is a cell surface cadherin-like protein that contains domains known to be involved in signal transduction pathways.

the cDNA. These nucleotide sequences that did not match the exon sequence for CLASP-1 were considered to be intron sequences. The two nucleotides spanning the intron/ exon boundary are indicated in the table below.

| splice junction (with reference to the nucleotides of the cDNA sequence found on either side of the junction, SEQ ID NO: 3) | Sequence Reference | Junction sequence (the exon sequence is in capitals, the intron in lower case) |
|---|---|---|
| SEQ ID NO: 3 pos 148/149 | SEQ ID NO: 16 | ATCTNTTGTGCATACTaaagaaaaaataaatacaaatattgttt |
| SEQ ID NO: 3 pos 340/341 | SEQ ID NO: 17 | TAGTATCAGATTATAGAAGgtatgtttttttatactctcgaaattaacat |
| SEQ ID NO: 3 pos 642/643 | SEQ ID NO: 18 | AAAGTGCCAAGCCCCTGAAGgtgagccaagtcagcaaagggacc |
| SEQ ID NO: 3 pos 1161/1162 | SEQ ID NO: 19 | ATTTCATCCGCTCTTGTAAGgtaacatgacatgcaagcagtttcagt |
| SEQ ID NO: 3 pos. 1464/1465 | SEQ ID NO: 20 | CAGTAAAGCATGTCCTAAAGgtaagaatttaaagatggtcctttaactgt |
| SEQ ID NO: 3 pos. 1683/1684 | SEQ ID NO: 21 | GCGTTGCCAGATTTCTCAAGgtacagttatatgagatcgcagttctattc |
| SEQ ID NO: 3 pos. 1962/1963 | SEQ JD NO: 22 | ganaggangatcacttacTGGCTCTCTGTATCGATCATCAAATGA |
| SEQ ID NO: 3 pos. 2085/2086 | SEQ ID NO: 23 | ACTTCTCGGAGCAGAATTCCnttagaaggtttgcgcaaatcat |
| SEQ ID NO: 3 pos. 2202/2203 | SEQ ID NO: 24 | CTGNCAATACATCTAATCAGgtacgtttgcacaatatgtcacatttctatgtt |
| SEQ ID NO: 3 pos. 2311/2312 | SEQ ID NO: 25 | AAGATGTTTTAAATTCNTAGcaggtacttgagatcttctgagaacactta |
| SEQ ID NO: 3 pos. 2618/2619 | SEQ ID NO: 26 | GACTTCTTCAGCATCTTGGAgtaagttttagagttgatgacttaacactttttc |
| SEQ ID NO: 3 pos. 2893/2894 | SEQ ID NO: 27 | TTAGACAATACCATGACCAGtaagtaaactgaaataataggaacaagatg |
| SEQ ID NO: 3 pos. 3144/3145 | SEQ ID NO: 28 | TTGAGACTGTTTGTATGCAAGgtaaggatctccaggtttcaatgaagtttag |
| SEQ ID NO: 3 pos. 3327/3328 | SEQ ID NO: 29 | GTCCCACTTACAAgtaagtgctgccaattttaattaatgctgttgttaaaacca |
| SEQ ID NO: 3 pos. 3622/3623 | SEQ ID NO: 30 | TTCACCTCTGCTGGGAAARRcgctgttctntggaaangagagagcctgggt |
| SEQ ID NO: 3 pos. 3657/3658 | SEQ ID NO: 31 | GAAACGGAGATTTATCTGAGgtgattagcaaggcttggtcatttaccat |
| SEQ ID NO: 3 pos. 3879/3880 | SEQ ID NO: 32 | cttcngaagaaggagcgatgAAAGAGGATTCTGGAATGCAAGATA |
| SEQ ID NO: 3 pos. 3918/3919 | SEQ ID NO: 33 | AGATACACCATACAATGAGgttagaccaaaattatctcatgtacagtaacc |
| SEQ ID NO: 3 pos. 4511/4512 | SEQ ID NO: 34 | AAGCGGCGGACGATNCTGNCAAgtnggtgcaggtagccgggccacac |

Example 2

Human CLASP-1 Sequence and Analysis

The sequences encoding human CLASP-1 were identified by hybridization with the mouse sequence. The human CLASP-1 sequence is provided as SEQ ID NO:3.

Southern hybridization analysis of human CLASP-1. Genomic DNA prepared by from HeLa cells (ATCC #CCL-17) or a BAC DNA clone was digested with EcoRI or HinDIII (genomic DNA), or EcoRI or PstI (BAC DNA) and eletrophoresed and transferred to nylon membrane by standard methods (Sambrook, Fritsch and Maniatis, 1989). For a probe, a CLASP-1-specific DNA fragment (HC. 1) was generated by PCR from a human CLASP-1 cDNA clone (SEQ ID NO:, using primers HC1S5' and HC1-EC12-IgE (spanning nucleotides 1119–2154 of the cDNA). The fragment was labeled by incorporation of radioactive $^{32}$p dCTP. Probe HC1.1 is 1036 bp long and it recognizes five bands (approximately sized at 1.6 kb, 2.8 kb, 7 kb, 9 kb, and 14 kb) in HindII digested genomic DNA. HC1.1 recognizes 6 same bands (approximately sized at 1.2 kb, 1.9 kb, 2.2 kb, 7 kb, 9 kb, and 12 kb) in EcoRI digested genomic DNA and BAC 5 DNA.

Intron-Exon Analysis. These boundaries were defined by sequencing Bacterial Artificial Chromosomes containing genomic DNA corresponding to human CLASP-1 (BACs). BACs were sequenced using primers derived from exon sequences corresponding to the CLASP-1 cDNA. Each exon/intron boundary is referenced by sequence, and exact nucleotide location of introns. Not all of the sequence from sequencing reactions on BACs produced sequence matching Example 3

Expression Pattern of CLASP-1 And Cellular Localization of its Encoded Product

Th1 cells (5CC7), pro-GMB cells (HAFTLJ), pre-B cells (NFS40, HSIC5, BAC14), mature B cells (BALL 17), and plasmacytomas (S194, J598L) were maintained as cultured cell lines. RNA were extracted from these cells for Northern blot analysis.

Northern blot analysis: Ten micrograms ($\mu$g) total RNA from each cell sample were loaded onto a 1% agarose formaldehyde gel, transferred onto BioBlot nitrocellulose paper (Costar, MA) and crossli,ked with Stratalink (Stratagene, La Jolla, Calif.). Prehybridization and hybridization were performed in 50% formamide, 25 mM sodium phosphate (pH 6.5), 1× Denhardt's solution, 200 $\mu$g/ml herring sperm DNA, and 5×SSC, at 65° C. Probes corresponding to the coding sequence of Clasp-1 were prepared using Ready-To-Go Labeling Kit (Pharmacia, NJ) according to the manufacturer's instructions, and desalted using pasteur pipet G-50 Sephadex column in TEN (10 mM Tris-HCl, pH 8, 1 mM EDTA, and 100 mM NaCl). The final wash of the blots was in 0.1×SCC at 60° C. Autoradiography was performed on Kodak XOMAT film at −80° C. with an enhancing screen.

Cytospin and immuno fluorescence: Cells were cytospun (Cytospin 1, Shandon]) onto poly-L-lysine (Sigma #P2636, MA) slides, fixed in periodate-lysine-paraformaldehyde (McLean and Nakane, 1974, J. Histochem. Cytochem. 22: 1077–83). Primary antibodies were added at 20–30 $\mu$g/ml in 10% normal donkey serum, TBS-C (50 mM Tris-HCl, pH 7.4, 150 mM NaCl, 1 mM CaCl$_2$), and 0.4% saponin, and incubated overnight at 4° C. After washing, secondary antibodies (Jackson immunoresearch, PA) were added and incubated at 37° C. for 30 minutes. For extracellular staining, a three-step sandwich assay was used. The first step was Gamma-bind purified goat antisera in 10% normal mouse serum, 10% normal rat serum, TBS-C for overnight at 4° C. in a humidifying chamber; the second step was biotin-conjugated monoclonal anti-goat antibody (Sigma, MO) at 1/50 dilution for 2 hours at room temperature; and the last step 5 was strepavidin-PE (Molecular Probes, OR) at 1/50 for 1 hour at room temperature. A FITC-conjugated anti-B200 or anti-CD3 antibody was also added at the last step.

Immunohistochemistry: Four-week-old mice were anesthetized and perfusion fixed with 4% paraformaldehyde in 0.1 M cacodylate (pH 7.4). Spleen cryosections (5–7 μm) were permeabilized with CSK (50 mM NaCl, 300 mM sucrose, 10 mM Pipes at pH 6.8, 3 mM $MgCl_2$, 0.5% Triton X-100, and 1 mM PMSF) for 10 minutes, and blocked with PBS+20% normal goat serum, 0.2% BSA, 50 mM $NH_4Cl$, 25 mM glycine, and 25 mM lysine for 2 hours at room temperature (Greenberg and Edelman, 1983, Cell 33: 767–79). Sections were incubated in 100 μl of the primary antibody in TBS-C+25% normal goat serum overnight at 4° C. and washed three times in TBS-C. One hundred μl of a secondary antibody (Jackson Immunoresearch, PA) was added for two hours at room temperature. Stained sections were examined under Nikon Biophot or Zeiss Axiophot fluorescent microscope and photographs were taken using Kodak Elite ASA 100.

Figure 3A:
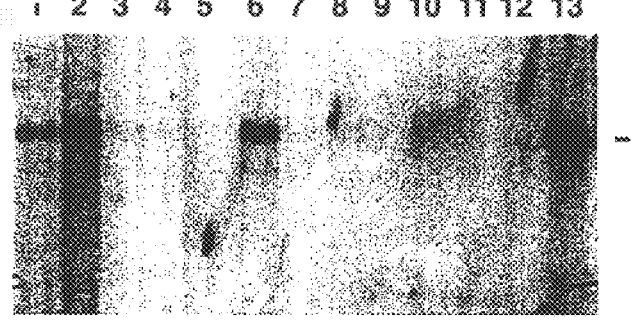
FIG. 3a: Clasp-1 is predominantly expressed in lymphoid tissues and in the brain. Ten μg of total RNA were loaded and probed with the Clasp-1 cDNA sequence to reveal a 13 kb band, suggesting that the 5' untranslated region was very long, or that it was a polycistronic message. The initiation methionine is predicted from the Kozak consensus sequence. Lane: 1) thymus, 2) spleen, 3) small intestine, 4) skin, 5) muscle, 6) lymph node, 7) lung, 8) liver, 9) kidney, 10) heart, 11) colon,. 12) bone marrow, 13) brain. Clasp-1 is found in the thymus, spleen, lymph node and the brain.
Figure 3B:
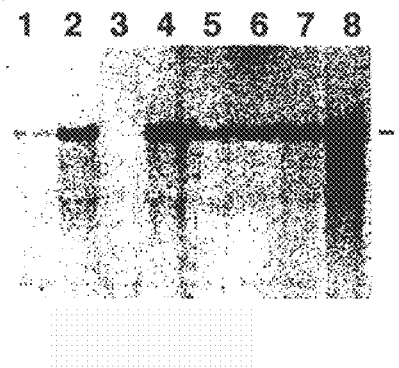
FIG. 3b: Clasp-1 is expressed in both T and B lymphocytes. Ten μg of total RNA were loaded in each lane. Lane: 1) S194 (IgA plasmacytoma), 2) NFS 40 (pre-Bcell), 3) J558L (IgA plasmacytoma), 4) HSIC 5 (pre-B cell), 5) HAFTLJ (pro-granulocytemacrophagecell), 6) Bal 17 (mature B cell), 7) BAC 14 (pre-B cell), 8) 5CC7 (CD4 T cell). Clasp-1 is expressed in most cell lines tested; it is absent in J558 and in low levels in S194, both plasmacytomas.

When lymphoid tissues (thymus, spleen, lymph nodes and bone marrow) were tested for mouse Clasp-1 expression by RNA blot analysis, a 13 kb Clasp-1 transcript was detected. The same transcript was also observed in the brain, but was missing from the liver, lung, muscle, kidney, and skin (FIG. 3a). Further analysis in lymphoid cell lines indicated that the Clasp-1 transcript was present in lymphocytes of both T and B cell lineage (FIG. 3b). However, the transcript was either absent or minimally expressed in several plasmacytoma lines (S194 and J558L), suggesting that the gene may be turned off in terminally differentiated B cells.

Immunostaining of spleen cryosections with an anti-Clasp-1 antiserum revealed that protein expression was most prominent in the marginal zone of the spleen (FIG. 4c, M), and in the T (FIG. 4a, T) and B (FIG. 4b, B) cell zones of the periarterial lymphatic sheaths (PALS). Anti-Clasp-1 antibody also stained macrophages in the MOMA-1 subregion of the marginal zone, an important site for T cell-dependent humoral response (Claassen et al., 1986, Eur. J. Immunol. 16: 492–97), but did not stain the MOMA-1 macrophages themselves (van Vliet et al., 1985, J. Histochem. Cytochem. 33: 40–44; Kraal et al., 1988, Immunol. Lett. 17: 139–44) (FIGS. 4c, 4f). In the PALS, most of the T cells expressed Clasp-1, whereas most of the B cells did not (FIGS. 4d, 4e). It is noteworthy that the staining pattern in T lymphocytes was apical, and where cells were arranged in clusters their apices were pointed into the B cell zone (FIG. 4d, arrow head).

Isolated lymphocytes from spleens also displayed the same apical distribution as lymphocytes in vivo (FIGS. 4g, 4h). T cells (D10) grown in the absence of antigen also exhibited the same surface polar distribution (FIG. 4i), as well as B cells (CH27, FIG. 4j), indicating that the apical grouping was not the result of antigen-induced crosslinking, but was an inherent property of Clasp-1 itself. To orient the structure to a subcellular landmark (i.e., the microtubule-organizing center), T cells (D10 and 2B4) were stained for both α-tubulin (green) and Clasp-1 (red). The apical Clasp-1 structure was always observed on the same side of the nucleus (blue) as the microtubule-organizing center (FIG. 4k). For most cell types examined, the centrisome was always on the same side of the nucleus as the leading edge, indicating that Clasp-1 pole was associated with the leading edge.

Figure 5:
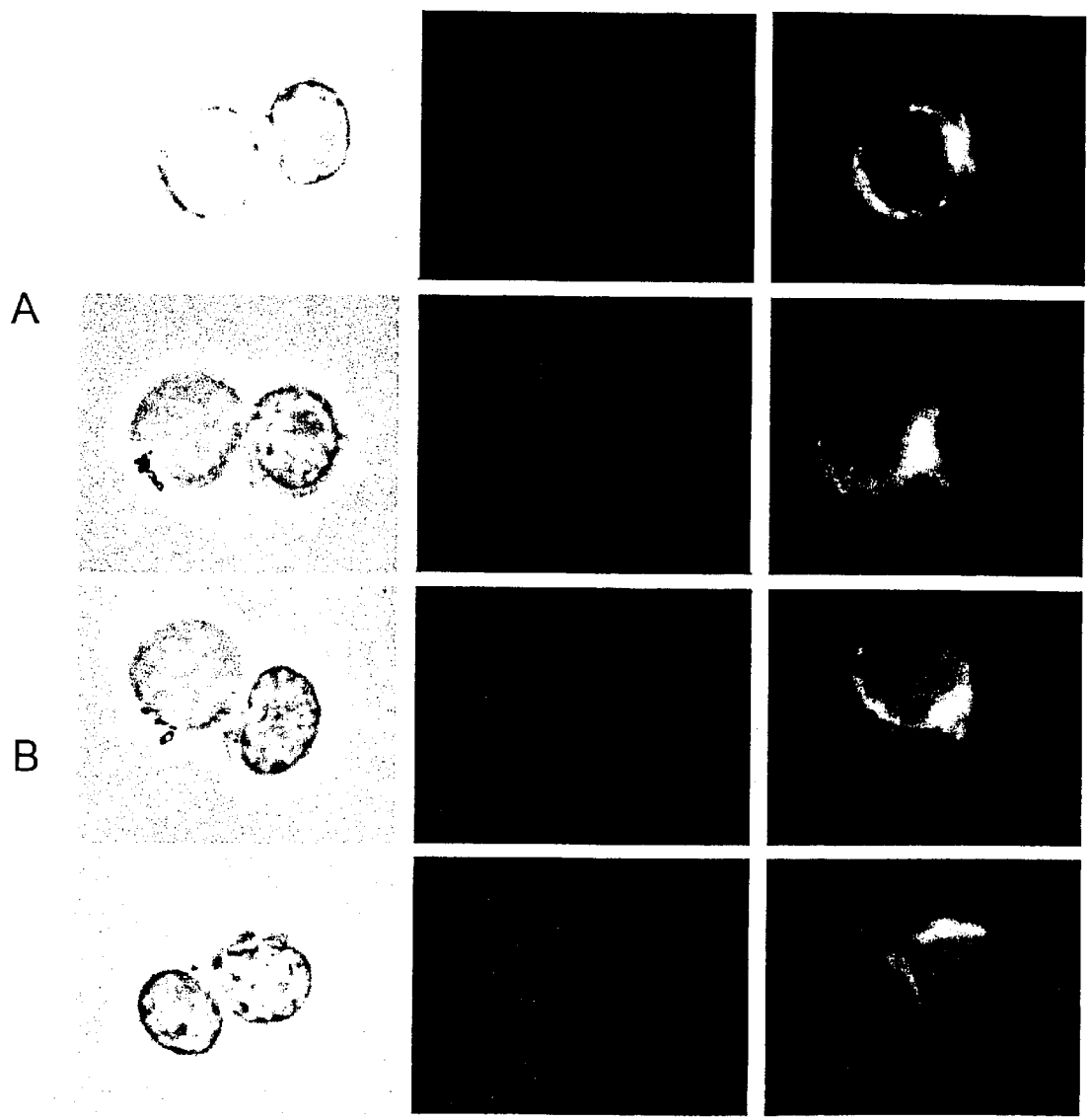
FIG. 5a: Clasp-1 in productive and non-productive T-B cell interactions. 3A9 and 5b HEL TCR transgenic splenocytes were cultured in the presence of HEL peptide for 10 hours. Cells were cytospun, fixed, permeabilized and stained for Clasp-1 (red) and CD3 (green). The corresponding phase-contrast (PC) picture is adjacent to each set.
FIG. 5b: In non-productive T-B interaction (T cell was not undergoing blast transformation), Clasp-1 was not facing the cell-cell interface.

To examine the role of Clasp-1 in cell conjugate formation during antigen-presentation by B cells, splenic lymphocytes from 3A9 mice, transgenic for TCR to hen egg lysozyme (HEL 46–61 peptide:I-$A^k$) (Ho et al., J. Exp. Med. 179: 1539–49), were cultured in the presence of the HEL peptide and allowed to form conjugate T-B cell pairs (Sagerstrom et al., 1993, Proc. Natl. Acad. Sci. USA 90: 8987–91). Cultured cellswere removed at 4, 10 and 36 hours. T-B cell pairs were observed by 4 hours, and by 10 hours more than 95% of the tight T-B cell pairs demonstrated early blast transformation (loss of nuclear membrane definition and heterochromatin). In productive interacting cell pairs, Clasp-1 was always found at the cell-cell interface (FIG. 5a), while in non-productive cell pairs, Clasp-1 was oriented randomly relative to the cell-cell interface (FIG. 5b). Cultures with non-activating peptide did not show any evidence of T cell activation or specific orientation.

Expression of CLASP-1 in human cell lines and human tissues as determined by Northern hybridization. A CLASP-1-specific DNA fragment (HC1.3) was generated by PCR from the human CLASP-1 cDNA clone, using primers C1S18 and 115CR (spanning nucleotides 4116–5067 of the cDNA). The fragment was labeled by incorporation of radioactive $^{32}p$ dCTP. The labeled DNA fragment was used as a probe on a human Multiple Tissue Northern (Clontech MTN Blot, #7780–1). A single band was clearly detected migrating at approximately 7.5 kb in brain, heart thymus spleen and peripheral blood lymphocytes (PBL). Slight expression was detected in colon, kidney, liver, small intestine, placenta, and lung.

A Northern blot with RNA from multiple hematopoietic cell lines was hybridized with the same hCLASP-1 probe. A similarly migrating 7.5 kb band is detected in Jurkat (T-cell derived), MV4-11 (myelomonocyte-derived), THP (monocyte-derived), and 9D10 (B-cell derived. Weak expression was also detected in the mouse cell lines CH27 (B cell lymphoma) and 3A9 (T-cell hybridoma).

Example 4

Inhibition of T Cell-B Cell Couplina by Anti-CLASP-1 Antibody

Fusion Protein and Antibodies: A coding sequence for amino acid residues 121–327 of Clasp-1 (SEQ ID NOS:1 and 2) was cloned into pGEX4T-1 (Pharmacia, NJ) at the BamH1/Not 1 site and it was referred to as GST-Clasp-EC12A. GST-Clasp-cyto was a construct that contained DNA encoding amino acid residues 969–1289 of Clasp-1 cloned into pGEX4T-3 (Pharmacia, NJ) at the NotI/EcoRI sites. Fusion proteins were expressed and purified according to instructions from Pharmacia using glutathione-Sepharose columns (Pharmacia, NJ) and used as immunogens for the generation of rabbit and goat antisera. Antibodies MOMA-1 (Kraal and Janse, 1986, Immunology 58: 665–669) and ER-TR-9 (van Vliet et al., 1985, J. Histochem. Cytochem. 33: 4044) were used as described. Anti-CD4-FITC, CD8-FITC, CD3-FITC, CD45R (B220)-FITC antibodies were purchased from Caltag, CA. YOL 1/34 was purchased from Sera-Tec, (NC).

Western Blot analysis: Cells were lysed in 50 mM Hepes (pH 7.4), 150 mM NaCl, 10% glycerol, 1% Triton X-100, Aprotinin (1 U /ml), leupeptin (2 μg/ml), pepstatin (1 μg/ml), antipain (2 μg/ml), PMSF (1 mM), and 100 μl/ml Sepharose 6 L to preclear the lysate. Cell lysate was electrophoresed on 10% SDS-PAGE, blotted onto a PVDF membrane (Millipore, MA) (Harlow and Lane, 1988, *Antibodies: A*

*Laboratory Manual*, Cold Spring Harbor Laboratory), and blocked overnight in 5% non-fat milk and 2% BSA in TBS-C. Protein-A or Gamma-bind (Pharmacia, NJ) purified anti-Clasp antibodies were added at 10 μg/ml in 0.5% non-fat milk, 0.2% BSA, 50 mM $PO_4$ (pH 7.4), 0.3 M NaCl, 0.1% Tween-20 and incubated for 2 hours at room temperature. After washing, goat anti-rabbit HRP-conjugated antibodies (Biomeda) were added at 1/5,000 dilution for 1 hour at room temperature, and visualized with ECL (Amersham, Ill).

Cell conjugation and inhibition assay. 2B4 or D10 T cells and CH27 B cells (loaded overnight with 10 μM moth cytochrome c peptide 88–103 or with conalbumin) were resuspended at $3.4 \times 10^5$ cells/ml in RPMI+10% FCS. 120 μl of each cell type were mixed in a 8 well coverslip slide chamber (Nunc, NY) and Gammabind (Pharmacia, NY) purified goat anti-Clasp-EC12A or anti-Clasp-cyto antibodies were added to a final concentration of 0, 50, and 150 μg/ml (pre-immune serum up to 450 μg/ml). Cells were allowed to couple for 5–7 hours at 37° C., then counted in a hemacytometer. For each sample, 100–150 couples were counted and normalized against the total number of cells (typical frequencies were between 7–10%). Percent inhibition was calculated against the frequency of couples in the positive control after subtraction of the frequency of non-specific couples in samples where CH27 B cells were not loaded with moth cytochrome c peptide.

Results

Figure 3C:
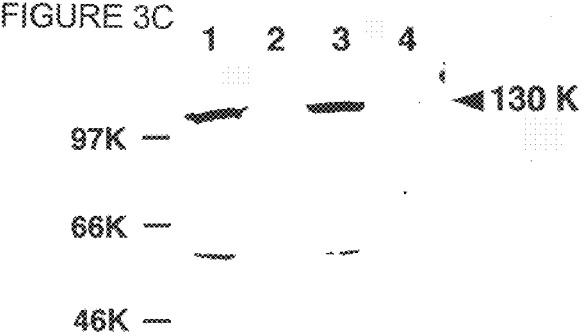
FIG. 3c: Clasp-1 protein is about 130 kd molecular weight in both T and B cells. Western blots of 2B4 cytoplasm/membrane (lane 1) or nuclei (lane 2) and CH27 cytoplasm/membrane (lane 3) or nuclei (lane 4) were probed with a goat antiserum to the cytoplasmic domain of Clasp-1. A 130K Clasp-1 band was seen in both T and B cells in the cytosol/membrane fraction. The same 130 kd band was detected with antisera to the putative extracellular domain of Clasp-1. A minor band of 55 kd may represent a degradation product of Clasp-1 or a cross-reactive protein.

Antibodies were generated against Clasp-1 fusion proteins. When Western blot analysis was performed using extracts from CH 27 (a mature B cell line) and 2B4 (a T cell hybridoma), antibodies raised against GST-fusion proteins containing either the extracellular domain (Clasp-EC12A) or the cytoplasmic domain (Clasp-cyto) identified a band of about 130 kD molecular weight, which was consistent with the deduced molecular weight of 134 kD (FIG. 3c) of Clasp-1.

Figure 6B:
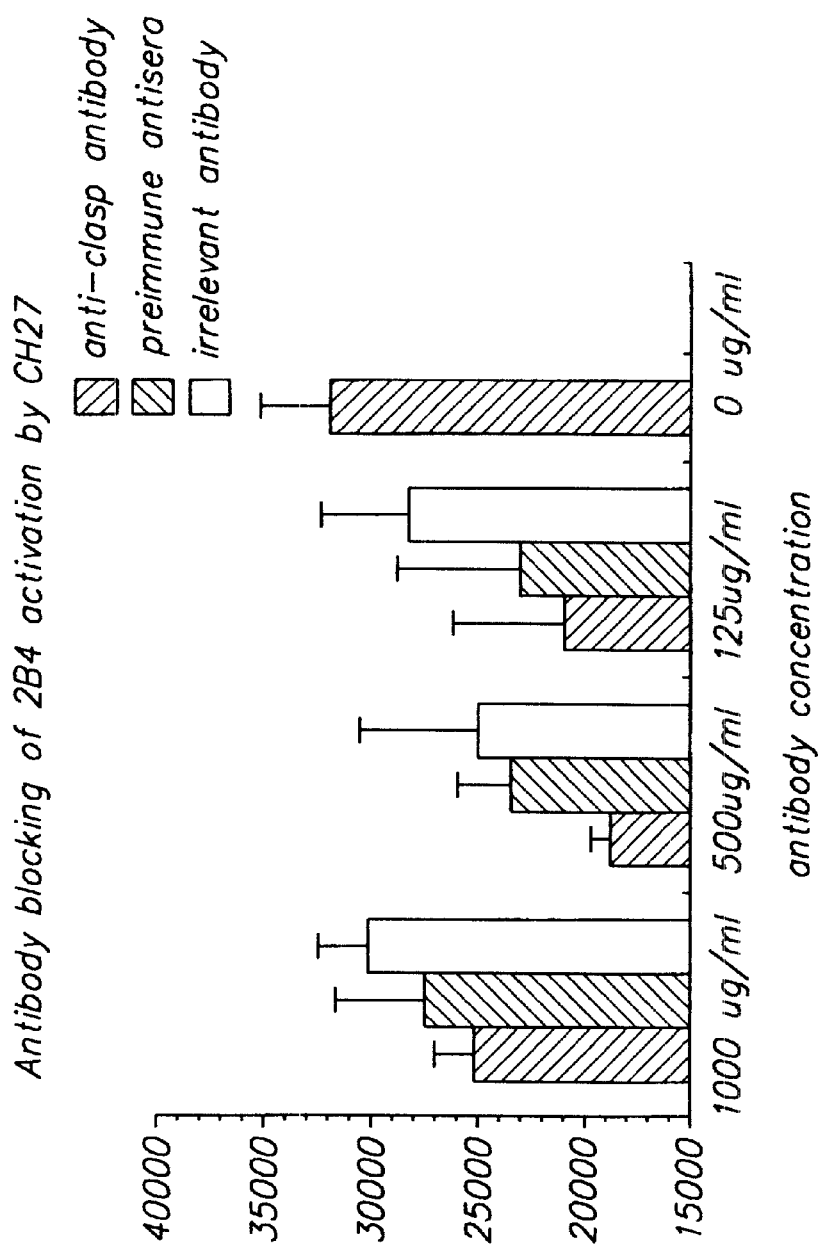
FIG. 6b: Goat anti-Clasp-EC12 blocks T cell activation. 2B4 T cell hybridoma with specificity for moth cytochrome c (MCC) in the context of I-E$^k$ was mixed with CH27 B cell loaded with MCC peptide. Gamma-bind (Pharmacia, NJ) purified goat anti-Clasp-EC12 or pre-immune serum was added at 0, 125, 500 and 1,000 μg/ml. IL-2 levels were measured after 48 hours of co-incubation and found to diminish in a dose dependent fashion. Pre-immune serum did not inhibit T cell activation as measured by IL-2 stimulation. Samples were performed in triplicate.

In order to explore the role of Clasp-1 in the establishment of physical linkage between T and B cells, the ability of the antibodies directed against the extracellular domain of Clasp-1 to prevent T-B cell coupling was assessed (Stowers et al., 1995, Proc. Natl. Acad. Sci. USA 92:5027–5031). T cell hybridoma, 2B4, specific for moth cytochrome c:1-$E^k$ as mixed with a B cell, CH27, loaded with moth cytochrome c peptide, in the presence of anti-Clasp-EC12A IgG antiserum. As shown in FIG. 6a, T-B cell pairing was blocked in a dose-dependent fashion by the anti-Clasp-EC12A antiserum, whereas the pre-immune serum had minimal effect on cell coupling even at high antibody concentrations. Similar findings were obtained in another antigen-specific system (D10 T cell line, specific for conalbumin:1-$A^k$). Furthermore, results of IL-2 assays of T cell activation also mirrored the coupling results (FIG. 6b). Thus, the Clasp-1 apical surface domain participates in marking the functional polarity in T cells prior to antigen encounter and in mediating cell-cell interactions between T and B cells following T cell engagement.

Example 5

Kinetics of CLASP-1 Redistribution

The distribution of CLASP-1 on the surface of a T cell changes with stimulation. When the T cell clones 2B4 was stimulated with PMA and ionomycin, after 30 minutes there was a sharp redistribution of the CLASP-1 uropedal distribution. The CLASP-1 cap structure was found to be co-incident with staining for CD3 on the T cell surface.

Figure 7:
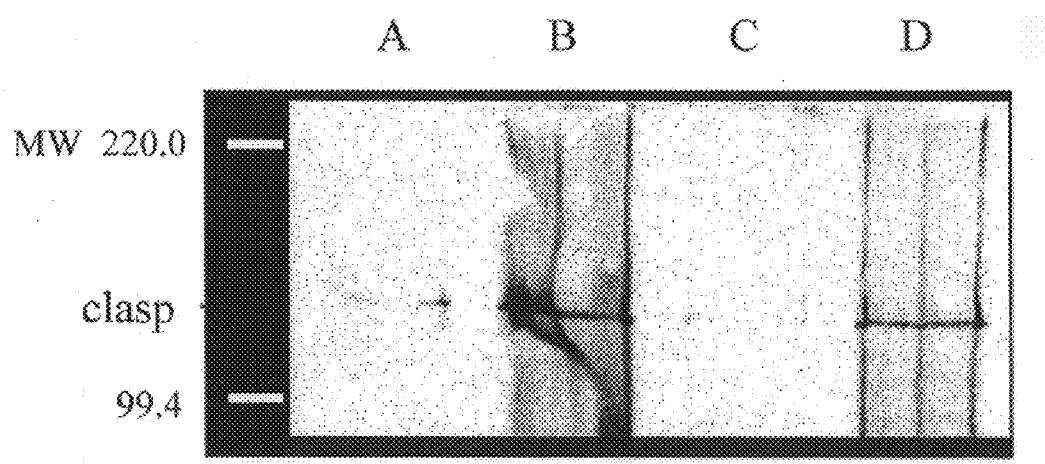
FIG. 7 shows the cytoskeletal associations of CLASP-1. Whole cell lysates of 2B4 cell lysates were run on 10% PAGE-SDS gel. The activated cells were treated with PMA and ionomycine 75 minutes prior to lysis. The insoluble fraction contained cytoskeletal associated proteins. Lane A is resting 2B4 cells; lane B activated 2B4 cells; lane C activated cells in the presence of nocodazole; and lane D activated cells in the presence of cytochalasinD.

The CLASP-1 protein in the T cell becomes associated with the cytoskeleton after stimulation. After 60 minutes, when the T cells were stimulated with PMA and ionomycin, there was a significant increase in the amount of CLASP-1 in the cytoskeletal, insoluble fraction. This change in cytoskeletal association was almost completely disrupted by the presence of nocodazole; and was also disrupted to a lesser extent by the presence of cytochalasin D (shown in FIG. 7). Nocodazole did not affect the c-capping of CLASP-1 by anti-CD3 antibody. These data demonstrates the involvement of microtubules in the resdistribution of CLASP-1.

The chemokine RANTES activates T cells through the cAMP pathway to reorganize cellular morphology via cytoskeletal changes, as well as surface receptors using a microfilament dependent process. RANTES treatment causes CD44 and CLASP-1 to redistribute in the T cell.

The cell line D10 was transfected with a CLASP-1 protein fused to green fluorescent protein. It was found that chemical activation of D10 cells caused a loss of the "hand mirror" morphology, and CLASP-1 expression to become more diffuse.

When T cell clone 2B4 was activated with PMA and ionomycin, it was found that the CLASP-1 co-localized with ankyrin. It was also found that the CLASP-1 co-localized with ankyrin in CH27 (B cells). Mapping experiments show that ankyrin binds to the C-terminal portion of CLASP-1.

In an immunoprocipitation experiment, a precipiate brough down with anti-ankyrin from either 2B4 T cells or CH27 B cells was able to co-precipitate CLASP-1. A similar experiment using anti-tubulin to immunoprecipitate failed to co-precipitate CLASP-1.

These data demonstrate that the protein CLASP-1 is associated with the cytoskeleton, and in T cells this association is increased by activation of the cells.

Example 6

CLASP-1 Protein Deletion Mutants

Materials and Methods

Oligos. The following oligos were synthesized (Gibco BRL, ROckville, Md. to build the Clasp-1 deletion constructs: (MP) SEQ ID NO:11 GGMGCTTCAGCACT-TCTA; (AB) SEQ ID NO:12 GGGGTACCTTCCATTTTC-CAGTA; (CD/COIL) SEQ ID NO:13 GGGGTACCCCTAAGCTGACAGGG; (COIL) SEQ ID NO:14 CCACTAGTCAGCTTAGGCTCTTT; and 3' SPE, SEQ ID NO:15 CCACTAGTMCCTCCGCACTGGA.

Plasmid construction. Expression vectors containing deletions of Clasp-1 cDNA were constructed in $pBJI^{neo}$ (Lin et al. (1990). This vector has been modified by addition into the multiple cloning site a linker containing an SpeI site followed by a FLAG tag, including a stop codon. Full-length Clasp-1 cDNA was cloned into $pBJI^{neo-FLAG}$ as an XhoI-SpeI fragment. Deletion of the cadherin homology regon of the cytoplasmic domain was accomplished by two separate PCR amplifications of full-length cDNA using the MP and AB oligos, and the CD/COIL and 3'SPE oligos. These PCR reactions resulted in fragment lengths of 497 and 879, respectively. The CD/COIL-3" SPE product was TA cloned into pGEM-T (Promega, Madison, Wis.); clones with the correct orientation were used for insertion of the MP-AB PCR product as a HindIII+KpnI fragment. The combined fragments were then subcloned into the full length pBJI$^{neo-FLAG}$ Clasp-1 vector via HindIII and SpeI. The resulting construct; pBJI$^{neo-FLAG}$ Clasp-1ΔIC deletes protein residues 846–997. Deletion of the sequence C-terminal to the cadherin homology domain of Clasp-1 was accomplished by PCR amplification of full-length cDNA using the MP+COIL oligos. This amplifies a 977 base pair fragment which was cloned into the full-length construct digested with HindIII and SpeI. This construct; pBJI$^{neo-FLAG}$ Clasp-1ΔCT deletes residues 1011–1289. The nucleotide sequences of the resulting cDNAs were then verified for each vector.

cDNA transfection. The 2B4 hybridoma (Hedrick et al. (1982) and the CH27 B cell lymphoma cell line were used to express the Clasp-1 deletion plasmids to assess the effects from both sides of the T cell:antigen presenting cell interaction. 5×10$^6$ 2B4 hybridomas were transfected at 240 V, 960 μF with expression constructs linearized with NheI. Stable transformants were isolated by selection with 0.4 mg/ml G418 sulfate (Geneticin®; Gibco BRL). 5×10$^6$ CH27 lymphoma cells were transfected at 240 V, 500 μF, and then stable isolates were isolated by selection with 0.8 mg/ml G418 sulfate. All cells were grown in RPMI 1640 (pH 7.3) supplemented with 10% fetal bovine serum. To rule out positional effects, three or more separate stable transfectant lines were made for each construct (except 2B4 transfected with pBJI$^{neo-FLAG}$ Clasp-1ΔIC, in this case single cell clones were derived from a single parent transfectant). Expression was confirmed by Western blot analysis and immunofluorescence microscopy using the anti-FLAG monoclonal antibody, M2 (Eastman Kodak, Rochester N.Y.).

Cell Activation Assays. 2B4 T cell hybridomas expressing the full-length and deletion constructs were stimulated in two ways. First, 10$^5$ cells/well were incubated at 37° for 18 hours in a 96-well plate coated with various concentrations of anti-CD3 (145-2C11, Pharmingen, San Diego Calif.). Alternatively, 10$^5$ cells/well were mixed with 10$^4$ untransfected CH27 cells and various concentrations of moth cytochrome C (MCC) 82–103 peptide followed by incubation at 37° for 18 hours in a 96 well plate. CH27 lymphomas expressing the constructs were tested by using 5×10$^4$ transfected CH27 to present MCC 82–103 peptide to 10$^5$ untransfected 2B4 cells (incubated at 37° for 18 hours in a 96 well plate). IL2 production was tested by assaying the supernatants with an IL2 sandwich ELISA (Pharmingen, San Diego Calif.) and the non-isotopic DELFIA system (EG&G Wallac, Wellesley Mass.).

Results

CLASP-1 contains a number of predicted protein interaction domains in the cytoplasmic tail. Using the amino acid numbering from the mouse protein sequence (SEQ ID NO:1), these include an SH3 domain (residues 847–859); a first SH2 domain (residues 923–935); a second SH2 domain (residues 951–962); a PTB motif and third SH2 domain (residues 1035–1053); and a PTB motif (residues 1255–1269). The PTB domain (phosphotyrosine-binding) is found in cytoplasmic docking proteins (see Kavanaugh et al. (1995) *Science* 268(5214):1177–9). These PTB domains are found primarily as components of docking proteins that recruit additional signaling proteins to the vicinity of an activated receptor.

Two deletion mutants were made in the coding sequence of mCLASP-1. The internal cytoplasmic deletion deleted amino acid residues 846–997, including the cadherin homology domain. The C-terminal cytoplasmic deletion deleted residues 1011–1289, including the PTB, an SH2 domain, and coiled coil domains. These constructs additionally added a FLAG sequence to provide a molecular tag for the proteins. The effects of these constructs were studied on transfection into the T cell clone 2B4.

Figure 8:
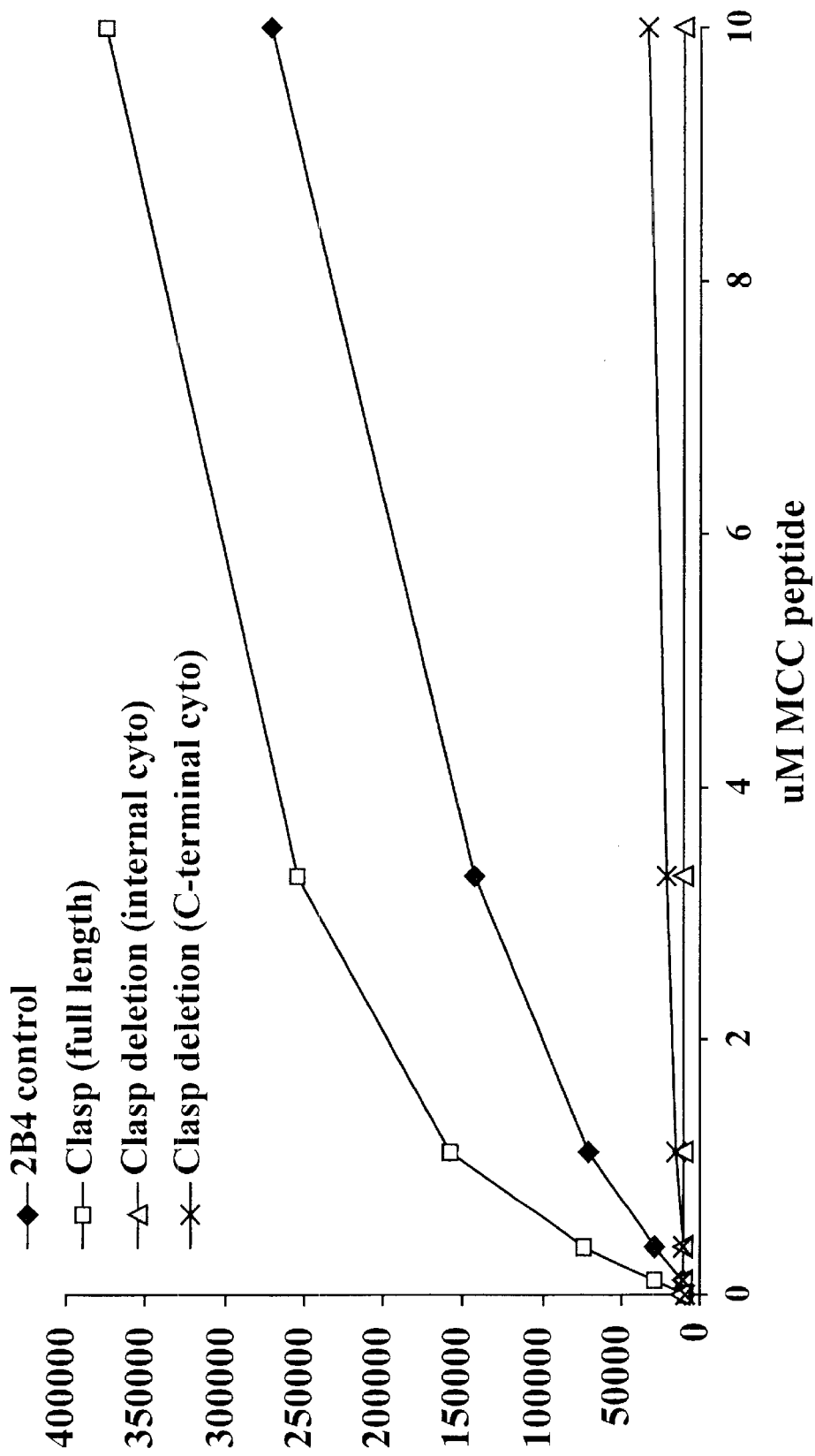
FIG. 8 is a graph depicting the production of IL2 by stimulated 2B4 T cells after presentation of MCC antigen by CH27 cells.

The cells that were transfected with the internal cytoplasmic deletion had a disrupted CLASP-1 morphology. Both the internal and C-terminal deletion mutants. lacked the ability to respond to the MCC antigen presented to the transfected T cell, as measured by production of IL-2, indicating that the deletion mutants had a dominant negative phenotype (shown in FIG. 8).

In contrast, the C-terminal deletion mutant could be activated by high levels of plate-bound anti-CD3, although the internal deletion could not be activated under these conditions.

Transfectants with both constructs were able to respond normally to PMA and ionomycin, indicating that the CLASP-1 function in the activation pathway is upstream of protein kinase C activation and Ca$^{++}$ release.

The transfected T cells were then tested on plates containing both CD3 and anti-CLASP-1 antibody, in order to determine whether the mutants were blocking activation by failing to properly redistribute. In normal cells, anti-CLASP-1 does not affect anti-CD3 stimulation. In the transfectants, the addition of CLASP-1 antibody did not rescue IL-2 production from CLASP-1 deletion mutant transfectants. The deletion mutants retained the ability to co-cap with CD3.

These data indicate that the effect of the deletions are to block signal transduction within the cap structure, not to prevent signal transduction by mislocalization.

Figure 9:
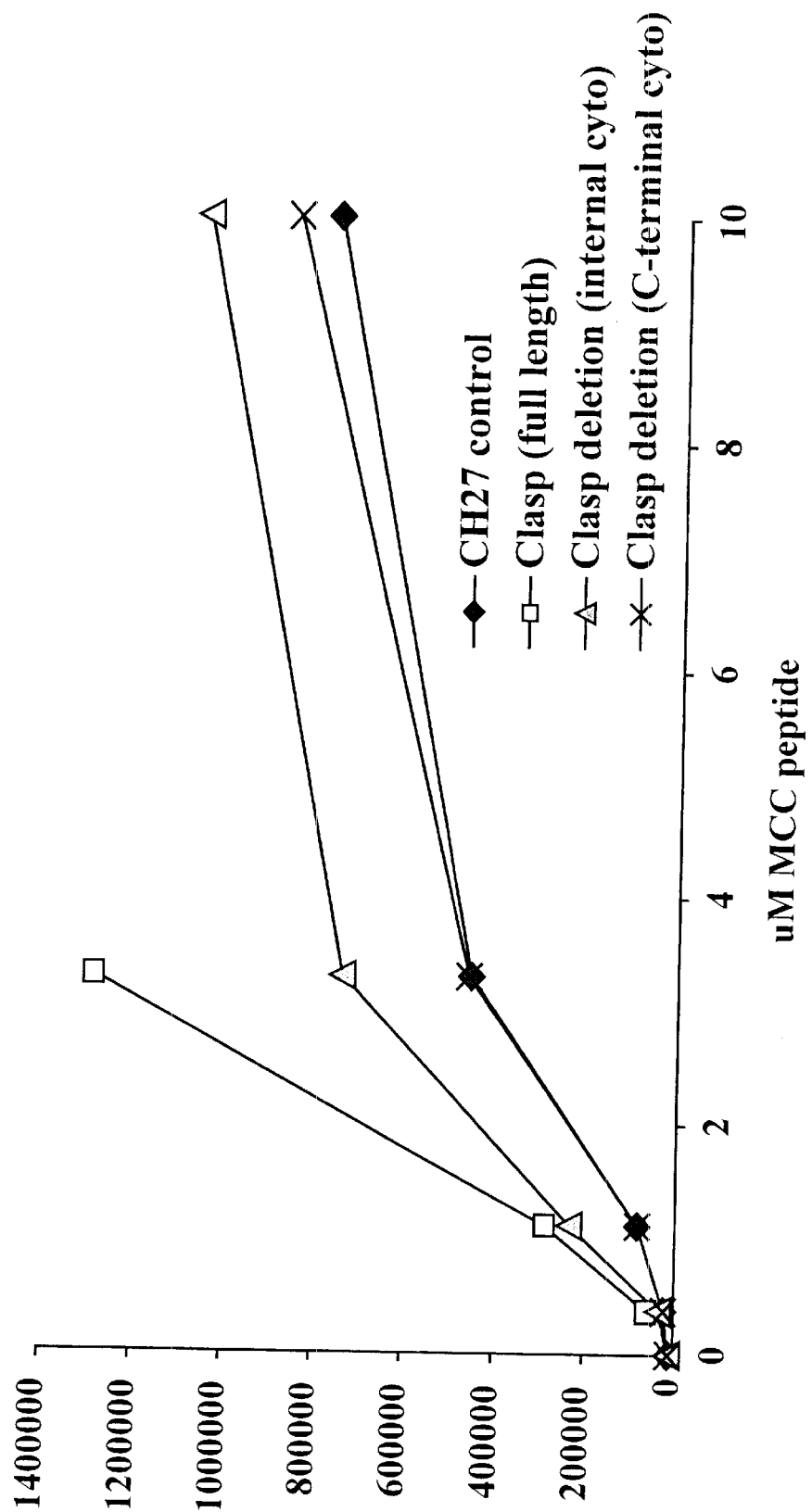
FIG. 9 is a graph depicting the production of IL2 by T cells stimulated with CH27 B cells, where the CH27 cells were transfected with deletion mutants of CLASP-1.

The effects of the CLASP-1 deletion mutants when transfected into the B cell clone CH27 were then determined. CH27 cells also had a disrupted morphology when expressing either of the deletion mutants. The ability of the B cells to act as antigen presenting cells was tested. It was found that the deletion mutation constructs did not have a dominant negative effect on antigen presentation, although they did not raise the antigen presenting efficiency to the extent that the full length contructs were able to (shown in FIG. 9).

Expression of the full-length CLASP-1 causes an increase in the ability of CH27 cells to stimulate T cells. The internal cytoplasmic deletion caused about half of this increase to be lost, while the C-terminal cytoplasmic deletion was only slightly higher than the non-transfected cells.

Example 7

Antibody Analysis of CLASP-1

The monoclonal antibody EC12A (anti-CLASP-1) was used to determine the effects of blocking CLASP-1 interactions. In a cell culture of 2B4 T cells and CH27 antigen presenting cells, addition of EC12A blocked conjugation between the two cell types. This block could be overcome at high concentrations of antibody, which may be attributed to cross-linking by the antibody.

The addition of EC12A antibody to 2B4 cells presented with an antigen recognized by the cells, resulted in an inhibition of IL-2 synthesis.

In transfected 3A9 T cells, surface levels of CLASP-1 were increased in the presence of antigen, as shown by cell surface staining with EC12A antibody.

The 5C.C7 lymphocyte cell line was analyzed for expression of CLASP-1 and CTLA-4. It was found that the two proteins were similarly distributed in the cells.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. A method of inhibiting a helper T cell mediated immune response, the method comprising:

contacting said T cell with an effective amount of an antibody that specifically binds a mammalian Clasp-1 polypeptide, wherein said polypeptide comprises the sequence of SEQ ID NO:1 or SEQ ID NO:4;

whereby the helper T cell mediated immune response and synthesis of IL-2 are inhibited.

2. The method of claim 1, wherein said immune response comprises activation of said T cell by an antigen presenting cell.

3. The method of claim 2, wherein said T cell is activated by a B lymphocyte.

4. The method of claim 1, wherein said step of contacting a T cell comprises administering a therapeutically effective amount of said antibody to a subject.

5. The method of claim 1, wherein said mammalian Clasp-1 protein comprises the amino acid sequence set forth in SEQ ID NO:1.

6. The method of claim 1, wherein said mammalian Clasp-1 protein comprises the amino acid sequence set forth in SEQ ID NO:4.

7. The method of claim 1, wherein said step of contacting a T cell comprises addition of said antibody to a cell culture in vitro.

8. The method of claim 1, wherein said T cell mediated immune response comprises IL-2 synthesis.

9. The method of claim 1, wherein said T cell is a helper T cell.

10. The method according to claim 1, wherein said polypeptide is a human Clasp-1 polypeptide.

11. A method of inhibiting activation of a helper T cell by an antigen presenting cell, the method comprising:

contacting said helper T cell with an effective amount of an antibody that specifically binds a mammalian Clasp-1 polypeptide, wherein said polypeptide comprises the sequence of SEQ ID NO:1 or SEQ ID NO:4;

whereby activation of said helper T cell and synthesis of IL-2 are inhibited.

12. The method according to claim 11, wherein said polypeptide is a human Clasp-1 polypeptide.

13. A method of inhibiting a helper T cell mediated immune response, the method comprising:

contacting said helper T cell with an effective amount of an antibody that specifically binds a Clasp-1 polypeptide, wherein said polypeptide is set forth in SEQ ID NO:1 or SEQ ID NO:4;

whereby the helper T cell mediated immune response and synthesis of IL-2 are inhibited.

14. A method of inhibiting activation or a helper T cell by an antigen presenting cell, the method comprising:

contacting said helper T cell with an effective amount of an antibody that specifically binds a Clasp-1 polypeptide, wherein said polypeptide is set forth in SEQ ID NO:1 or SEQ ID NO:4;

whereby activation of said helper T cell and synthesis of IL-2 are inhibited.

* * * * *

UNITED STATES PATENT AND TRADEMARK OFFICE
CERTIFICATE OF CORRECTION

PATENT NO. : 6,565,848 B1
DATED : May 20, 2003
INVENTOR(S) : Peter S. Lu et al.

It is certified that error appears in the above-identified patent and that said Letters Patent is hereby corrected as shown below:

Column 1,
Line 3, insert paragraph:
-- This invention was made with Government support under contact 5 P01 AI36535-04 awarded by the National Institutes of Health. The Government has certain rights in this invention. --

Column 20,
Line 33, "342:435438" should read -- 342:435-438 --

Column 25,
Line 10, "9(2):385412" should read -- 9(2):385-412 --

Signed and Sealed this

Sixth Day of January, 2004

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,565,848 B1 | Page 1 of 1 |
| APPLICATION NO. | : 09/546934 | |
| DATED | : May 20, 2003 | |
| INVENTOR(S) | : Lu et al. | |

It is certified that error appears in the above-identified patent and that said Letters Patent is hereby corrected as shown below:

In the Specification, Column 1, line 19, above the heading "BACKGROUND OF THE INVENTION", please insert:

-- FEDERALLY-SPONSORED RESEARCH OR DEVELOPMENT

This invention was made with Government support under contract AI036535 awarded by the National Institutes of Health. The Government has certain rights in this invention. --

Signed and Sealed this
Twenty-third Day of August, 2011

David J. Kappos
*Director of the United States Patent and Trademark Office*

SEQUENCE LISTING

<160> NUMBER OF SEQ ID NOS: 34

<210> SEQ ID NO 1
<211> LENGTH: 1289
<212> TYPE: PRT
<213> ORGANISM: Mus musculus

<400> SEQUENCE: 1

```
Met Ser Leu Leu Pro Met Ile Leu Asn Gln Leu Phe Lys Ile Leu Val
1               5                   10                  15

Gln Asn Glu Glu Asp Glu Ile Thr Ala Thr Val Thr Arg Val Leu Ala
                20                  25                  30

Asp Ile Val Ala Lys Cys His Glu Gln Leu Asp His Ser Val Gln
            35                  40                  45

Ser Tyr Ile Lys Phe Val Phe Lys Thr Lys Ser Tyr Lys Glu Arg Thr
    50                  55                  60

Ile His Glu Glu Leu Pro Lys Asn Leu Ser Asp Leu Leu Lys Ser Asn
65                  70                  75                  80

Asp Ser Thr Ile Val Lys His Val Leu Glu His Ser Trp Phe Phe Phe
                85                  90                  95

Ala Ile Ile Leu Lys Ser Met Ala Gln His Leu Ile Asp Thr Asn Lys
                100                 105                 110

Ile Gln Leu Pro Arg Ala Gln Arg Phe Pro Glu Ser Tyr Gln Ser Glu
            115                 120                 125

Leu Asp Asn Leu Val Met Gly Leu Cys Asp His Val Ile Trp Lys Cys
130                 135                 140

Lys Glu Ala Pro Glu Glu Thr Lys Arg Ala Asn His Ser Val Ala Arg
145                 150                 155                 160

Phe Leu Lys Arg Cys Phe Thr Phe Met Asp Arg Gly Phe Val Phe Lys
                165                 170                 175

Met Val Asn Asn Tyr Ile Ser Met Phe Ser Ser Gly Glu Phe Lys Thr
                180                 185                 190

Leu Cys Gln Tyr Lys Phe Asp Phe Leu Gln Glu Val Cys Gln His Glu
            195                 200                 205

His Phe Ile Pro Leu Cys Leu Pro Ile Arg Ser Ala Asn Ile Pro Asp
        210                 215                 220

Pro Leu Thr Pro Ser Glu Ser Ile Arg Glu Leu His Ala Ser Asp Met
225                 230                 235                 240

Pro Glu Tyr Ser Val Thr Asn Glu Phe Cys Arg Lys His Phe Leu Ile
                245                 250                 255

Gly Ile Leu Leu Arg Glu Val Gly Phe Ala Cys Arg Arg Asp Gln Asp
                260                 265                 270

Ile Arg His Leu Ala Leu Ala Val Leu Lys Asn Leu Met Ala Lys His
        275                 280                 285

Ser Phe Asp Asp Arg Tyr Arg Glu Pro Arg Lys Gln Ala Gln Ile Ala
    290                 295                 300

Ser Leu Tyr Met Pro Leu Tyr Gly Met Leu Leu Asp Asn Met Pro Arg
```

-continued

```
305                 310                 315                 320
Ile Tyr Leu Lys Asp Leu Tyr Pro Phe Thr Val Asn Thr Ser Asn Gln
                325                 330                 335
Gly Ser Arg Asp Asp Leu Ser Thr Asn Gly Gly Phe Gln Thr Gln Thr
                340                 345                 350
Val Met Lys His Ala Thr Ser Val Asp Thr Ser Phe Ser Lys Asp Val
                355                 360                 365
Leu Asn Ser Ile Ala Ala Phe Ser Ser Ile Ala Ile Ser Thr Val Asn
                370                 375                 380
His Ala Asp Ser Arg Ala Ser Leu Ala Ser Leu Asp Ser Asn Pro Ser
385                 390                 395                 400
Thr Thr Glu Lys Ser Ser Glu Lys Thr Asp Asn Cys Glu Lys Ile Pro
                405                 410                 415
Arg Pro Leu Ser Leu Ile Gly Ser Thr Leu Arg Phe Asp Lys Leu Asp
                420                 425                 430
Gln Ala Glu Thr Arg Ser Leu Leu Met Cys Phe Leu His Ile Met Lys
                435                 440                 445
Thr Ile Ser Asp Glu Thr Leu Ile Ala Tyr Trp Gln Arg Ala Pro Ser
450                 455                 460
Pro Glu Val Ser Asp Phe Phe Ser Ile Leu Asp Val Cys Leu Gln Asn
465                 470                 475                 480
Phe Arg Tyr Leu Gly Lys Arg Asn Ile Ile Arg Lys Ile Ala Ala Ala
                485                 490                 495
Phe Lys Phe Val Gln Ser Thr Gln Asn Asn Arg Thr Leu Lys Gly Ser
                500                 505                 510
Asn Pro Ser Cys Gln Thr Ser Gly Leu Leu Ser Gln Trp Met His Thr
                515                 520                 525
Thr Ser Gly His Glu Gly His Lys Gln His Arg Ser Gln Thr Leu Pro
                530                 535                 540
Ile Ile Arg Gly Lys Asn Ala Leu Ser Asn Pro Lys Leu Leu Gln Met
545                 550                 555                 560
Leu Asp Asn Ser Met Asn Ser Asn Ser Asn Glu Ile Asp Ile Val His
                565                 570                 575
His Val Asp Thr Glu Ala Asn Ile Ala Thr Glu Val Cys Leu Thr Ile
                580                 585                 590
Leu Asp Leu Leu Ser Leu Phe Thr Gln Val His Gln Arg Gln Leu Gln
                595                 600                 605
Gln Ser Asp Cys Gln Asn Ser Leu Met Lys Arg Val Phe Asp Thr Tyr
                610                 615                 620
Met Leu Phe Phe Gln Val Asn Gln Ser Ala Ser Ala Leu Lys His Val
625                 630                 635                 640
Phe Ala Ser Leu Arg Leu Phe Val Cys Lys Phe Pro Ser Ala Phe Phe
                645                 650                 655
Gln Gly Pro Ala Asp Leu Cys Gly Ser Phe Cys Tyr Glu Ile Leu Lys
                660                 665                 670
Cys Cys Asn His Arg Ser Arg Leu Thr Gln Met Glu Ala Ser Ala Leu
                675                 680                 685
Leu Tyr Phe Phe Met Ser Lys Asn Phe Glu Phe Asn Lys Gln Lys Ser
                690                 695                 700
Ile Val Arg Ser His Leu Gln Leu Ile Lys Ala Val Ser Gln Leu Ile
705                 710                 715                 720
Ala Asp Ala Gly Ile Gly Gly Ser Arg Phe Gln His Ser Leu Ala Ile
                725                 730                 735
```

-continued

```
Thr Asn Asn Phe Ala Asn Gly Asp Lys Gln Met Lys Asn Ser Asn Phe
            740                 745                 750

Pro Ala Glu Val Lys Asp Leu Thr Lys Arg Ile Arg Thr Val Leu Met
            755                 760                 765

Ala Thr Ala Gln Met Lys Glu His Glu Lys Asp Pro Glu Met Leu Val
            770                 775             780

Asp Leu Gln Tyr Ser Leu Ala Asn Ser Tyr Ala Ser Thr Pro Glu Leu
785                 790                 795                 800

Arg Arg Thr Trp Leu Glu Ser Met Ala Lys Ile His Ala Arg Asn Gly
                805                 810                 815

Asp Leu Ser Glu Ala Ala Met Cys Tyr Ile His Ile Ala Ala Leu Ile
            820                 825                 830

Ala Glu Tyr Leu Lys Arg Lys Gly Tyr Trp Lys Met Glu Lys Ile Cys
            835                 840                 845

Thr Pro Pro Leu Leu Pro Glu Asp Thr Gln Pro Cys Asp Ser Asn Leu
            850                 855                 860

Leu Leu Thr Thr Pro Gly Gly Ser Met Phe Ser Met Gly Trp Pro
865                 870                 875                 880

Ala Phe Leu Ser Ile Thr Pro Asn Ile Lys Glu Gly Ala Met Lys
                885                 890                 895

Glu Asp Ser Gly Met Gln Asp Thr Pro Tyr Asn Glu Asn Ile Leu Val
                900                 905                 910

Glu Gln Leu Tyr Met Cys Val Glu Phe Leu Trp Lys Ser Glu Arg Tyr
            915                 920                 925

Glu Leu Ile Ala Asp Val Asn Lys Pro Ile Ile Ala Val Phe Glu Lys
            930                 935                 940

Gln Arg Asp Phe Lys Lys Leu Ser Asp Leu Tyr Tyr Asp Ile His Arg
945                 950                 955                 960

Ser Tyr Leu Lys Val Ala Glu Val Val Asn Ser Glu Lys Arg Leu Phe
                965                 970                 975

Gly Arg Tyr Tyr Arg Val Ala Phe Tyr Gly Gln Gly Phe Phe Glu Glu
            980                 985                 990

Glu Glu Gly Lys Glu Tyr Ile Tyr Lys Glu Pro Lys Leu Thr Gly Leu
            995                 1000                1005

Ser Glu Ile Ser Gln Arg Leu Leu Lys Leu Tyr Ala Asp Lys Phe Gly
    1010                1015                1020

Ala Asp Asn Val Lys Ile Ile Gln Asp Ser Asn Lys Val Asn Pro Lys
1025                1030                1035                1040

Asp Leu Asp Pro Lys Tyr Ala Tyr Ile Gln Val Thr Tyr Val Thr Pro
                1045                1050                1055

Phe Phe Glu Glu Lys Glu Ile Glu Asp Arg Lys Thr Asp Phe Glu Met
                1060                1065                1070

His His Asn Ile Asn Arg Phe Val Phe Glu Thr Pro Phe Thr Leu Ser
            1075                1080                1085

Gly Lys Lys His Gly Gly Val Ala Glu Gln Cys Lys Arg Arg Thr Val
            1090                1095                1100

Leu Thr Thr Ser His Leu Phe Pro Tyr Val Lys Lys Arg Ile Gln Val
1105                1110                1115                1120

Ile Ser Gln Ser Ser Thr Glu Leu Asn Pro Ile Glu Val Ala Ile Asp
            1125                1130                1135

Glu Met Ser Arg Lys Val Ser Glu Leu Asn Gln Leu Cys Thr Thr Glu
            1140                1145                1150
```

```
Glu Val Asp Met Ile Arg Leu Gln Leu Lys Leu Gln Gly Ser Val Ser
            1155                1160                1165
Val Lys Val Asn Ala Gly Pro Met Ala Tyr Ala Arg Ala Phe Leu Glu
        1170                1175                1180
Glu Thr Asn Ala Lys Lys Tyr Ala Asp Asn Gln Val Lys Leu Leu Lys
1185                1190                1195                1200
Glu Ile Phe Arg Gln Phe Ala Asp Ala Cys Gly Gln Ala Leu Asp Val
            1205                1210                1215
Asn Glu Arg Leu Ile Lys Glu Asp Gln Leu Glu Tyr Gln Glu Glu Leu
        1220                1225                1230
Arg Ser His Tyr Lys Asp Met Leu Ser Glu Leu Ser Ala Ile Met Asn
            1235                1240                1245
Glu Gln Ile Thr Gly Arg Asp Asp Pro Ala Lys Cys Gly Val Glu Arg
        1250                1255                1260
Pro Tyr Thr Thr Arg Val Thr Ser Lys Gly Thr Ala Ala Val Pro Val
1265                1270                1275                1280
Val Ser Ile Ser Ser Ser Ala Glu Val
            1285

<210> SEQ ID NO 2
<211> LENGTH: 5214
<212> TYPE: DNA
<213> ORGANISM: mus musculus
<220> FEATURE:
<221> NAME/KEY: CDS
<222> LOCATION: (718)...(4587)

<400> SEQUENCE: 2
ggttttaaaa taaaacagaa acggctacag ttcttagcag gagagagagc gaggagttgt      60
caggaaagct gcaggttact ttgagacagt cgtcccaaat gcattagagg aactgtaaaa     120
atctgccaca gaaggaacga tgatccatag tcagaaaagt tactgcagct taaacaggaa     180
acccttcttg ttcaggactg tcatagccac agtttgcaaa agtgcagct attgattaat      240 gcaatgtagt gtcaattaga tgtacattcc tgaggtcttt tatctgttgt agctttgtct     300
ttttcttttt cttttcatta catcacatgt gacatcaatg ccaaagccaa tgccaaaaag     360
aaagaggctt ggagacatc agtgggctat gcatggcttc ctctgatgaa acatgatcaa      420
atagcttctc aggagtacaa catcccaata gcaacgaccc tgcctcctaa ttatttaagc     480
attcaagatc ctacaagtgc aaagcatggt ggaagtgaca ttaaatgggt cgatggtggc     540
aaaccgcttt tcaaagtgtc cacatttgtt gtatcaacag tgaacactca ggacccacat     600
gtaaatgcat ttttccgtca gtgccaaaaa agagaaaaag acatgtctca gtcacctacc     660
tccagctttg tccgtgcctg taagaactta ctaaatgtgg acaagatcca ctccatc atg    720
                                                                Met
                                                                 1 agt ttg ctg cct atg atc ttg aac cag ctc ttc aaa att cta gtg cag        768
Ser Leu Leu Pro Met Ile Leu Asn Gln Leu Phe Lys Ile Leu Val Gln
        5                   10                  15 aac gag gaa gat gaa att act gcg acc gtc acc agg gtt ctg gct gac        816
Asn Glu Glu Asp Glu Ile Thr Ala Thr Val Thr Arg Val Leu Ala Asp
    20                  25                  30 att gtg gcc aag tgt cat gag gag caa cta gac cat tct gtc cag tca        864
Ile Val Ala Lys Cys His Glu Glu Gln Leu Asp His Ser Val Gln Ser
35                  40                  45 tac att aag ttt gta ttc aag acc aaa tcc tac aaa gag aga aca ata        912
Tyr Ile Lys Phe Val Phe Lys Thr Lys Ser Tyr Lys Glu Arg Thr Ile
 50                  55                  60                  65
```

```
cat gag gaa ctg ccc aaa aat ttg agt gat ctt ttg aag tcc aat gac   960
His Glu Glu Leu Pro Lys Asn Leu Ser Asp Leu Leu Lys Ser Asn Asp
             70                  75                  80 tca acg ata gtc aag cat gtt cta gag cat tct tgg ttc ttc ttt gcc  1008
Ser Thr Ile Val Lys His Val Leu Glu His Ser Trp Phe Phe Phe Ala
                 85                  90                  95 att att cta aaa tca atg gca cag cac ttg att gac aca aac aaa att  1056
Ile Ile Leu Lys Ser Met Ala Gln His Leu Ile Asp Thr Asn Lys Ile
            100                 105                 110 cag ctt ccc aga gct caa aga ttc cct gag tct tac caa agc gaa cta  1104
Gln Leu Pro Arg Ala Gln Arg Phe Pro Glu Ser Tyr Gln Ser Glu Leu
        115                 120                 125 gac aac ttg gtg atg ggc ctg tgt gac cac gtg att tgg aaa tgc aag  1152
Asp Asn Leu Val Met Gly Leu Cys Asp His Val Ile Trp Lys Cys Lys
130                 135                 140                 145 gaa gcc cct gag gaa acc aaa aga gca aac cac agc gtt gcc aga ttc  1200
Glu Ala Pro Glu Glu Thr Lys Arg Ala Asn His Ser Val Ala Arg Phe
                150                 155                 160 ctt aag cgc tgc ttt aca ttt atg gac cgg gga ttc gtg ttt aag atg  1248
Leu Lys Arg Cys Phe Thr Phe Met Asp Arg Gly Phe Val Phe Lys Met
            165                 170                 175 gtg aac aat tac atc agc atg ttc tct tct ggt gag ttt aag act tta  1296
Val Asn Asn Tyr Ile Ser Met Phe Ser Ser Gly Glu Phe Lys Thr Leu
        180                 185                 190 tgc cag tat aag ttt gat ttc ctt cag gaa gtt tgt caa cat gag cac  1344
Cys Gln Tyr Lys Phe Asp Phe Leu Gln Glu Val Cys Gln His Glu His
    195                 200                 205 ttt atc cct ttg tgt ctc ccc ata aga tct gca aac att cca gat ccc  1392
Phe Ile Pro Leu Cys Leu Pro Ile Arg Ser Ala Asn Ile Pro Asp Pro
210                 215                 220                 225 ttg aca cct tca gaa tca atc cga gag tta cat gcc tca gat atg cct  1440
Leu Thr Pro Ser Glu Ser Ile Arg Glu Leu His Ala Ser Asp Met Pro
                230                 235                 240 gag tac tca gtc aca aat gaa ttt tgc cgc aaa cac ttc tta att gga  1488
Glu Tyr Ser Val Thr Asn Glu Phe Cys Arg Lys His Phe Leu Ile Gly
            245                 250                 255 att ctt ctc cga gaa gtt ggc ttt gcc tgc agg agg gac caa gac atc  1536
Ile Leu Leu Arg Glu Val Gly Phe Ala Cys Arg Arg Asp Gln Asp Ile
        260                 265                 270 agg cac tta gct tta gct gtc cta aaa aat cta atg gct aag cat tct  1584
Arg His Leu Ala Leu Ala Val Leu Lys Asn Leu Met Ala Lys His Ser
    275                 280                 285 ttc gat gat cga tac agg gaa cct agg aag cag gca cag ata gcg agt  1632
Phe Asp Asp Arg Tyr Arg Glu Pro Arg Lys Gln Ala Gln Ile Ala Ser
290                 295                 300                 305 ctg tac atg ccg ctc tat ggt atg ctc ctg gac aat atg cca aga atc  1680
Leu Tyr Met Pro Leu Tyr Gly Met Leu Leu Asp Asn Met Pro Arg Ile
                310                 315                 320 tac ctg aag gac ctg tat cct ttc acc gtg aac aca tcc aat cag gga  1728
Tyr Leu Lys Asp Leu Tyr Pro Phe Thr Val Asn Thr Ser Asn Gln Gly
            325                 330                 335 tct aga gat gac ctc agc act aat gga gga ttt cag act cag acc gtc  1776
Ser Arg Asp Asp Leu Ser Thr Asn Gly Gly Phe Gln Thr Gln Thr Val
        340                 345                 350 atg aaa cat gca act tct gtg gat aca tca ttt tcc aaa gat gtt tta  1824
Met Lys His Ala Thr Ser Val Asp Thr Ser Phe Ser Lys Asp Val Leu
    355                 360                 365 aat tcc ata gca gca ttt tca tca ata gct att tct aca gtg aac cat  1872
Asn Ser Ile Ala Ala Phe Ser Ser Ile Ala Ile Ser Thr Val Asn His
```

-continued

```
               370                 375                 380                 385
gca gat tcc aga gcg tcc tta gcg agc ctc gac tcc aac cca agt acc        1920
Ala Asp Ser Arg Ala Ser Leu Ala Ser Leu Asp Ser Asn Pro Ser Thr
                390                 395                 400 aca gag aag agc agt gag aag aca gac aac tgt gaa aag atc cca agg        1968
Thr Glu Lys Ser Ser Glu Lys Thr Asp Asn Cys Glu Lys Ile Pro Arg
            405                 410                 415 ccc ttg tct ttg att ggg tca acg ctt cgg ttt gac aaa tta gat caa        2016
Pro Leu Ser Leu Ile Gly Ser Thr Leu Arg Phe Asp Lys Leu Asp Gln
            420                 425                 430 gca gaa acc agg agt ctt ctt atg tgt ttt ctt cac att atg aag acc        2064
Ala Glu Thr Arg Ser Leu Leu Met Cys Phe Leu His Ile Met Lys Thr
            435                 440                 445 att tca gat gag act ctg att gcc tac tgg cag aga gca ccc agt cca        2112
Ile Ser Asp Glu Thr Leu Ile Ala Tyr Trp Gln Arg Ala Pro Ser Pro
450                 455                 460                 465 gag gtg tca gac ttc ttc agc atc ttg gac gtt tgt ctt cag aat ttt        2160
Glu Val Ser Asp Phe Phe Ser Ile Leu Asp Val Cys Leu Gln Asn Phe
                470                 475                 480 aga tac cta ggg aaa cgc aat ata ata agg aaa atc gct gca gcg ttt        2208
Arg Tyr Leu Gly Lys Arg Asn Ile Ile Arg Lys Ile Ala Ala Ala Phe
            485                 490                 495 aag ttt gtg cag tca acc cag aac aat agg act ctg aag gga tcc aat        2256
Lys Phe Val Gln Ser Thr Gln Asn Asn Arg Thr Leu Lys Gly Ser Asn
            500                 505                 510 cct tcc tgc cag aca tca ggt ctc ttg tca caa tgg atg cac acg act        2304
Pro Ser Cys Gln Thr Ser Gly Leu Leu Ser Gln Trp Met His Thr Thr
515                 520                 525 tct ggc cac gag gga cat aag cag cac agg tct cag act tta cct ata        2352
Ser Gly His Glu Gly His Lys Gln His Arg Ser Gln Thr Leu Pro Ile
530                 535                 540                 545 atc cga ggc aaa aat gca ctt tcc aac ccc aaa ctt tta cag atg ttg        2400
Ile Arg Gly Lys Asn Ala Leu Ser Asn Pro Lys Leu Leu Gln Met Leu
                550                 555                 560 gac aac agc atg aac agc aat tcc aat gaa ata gac att gtc cac cat        2448
Asp Asn Ser Met Asn Ser Asn Ser Asn Glu Ile Asp Ile Val His His
            565                 570                 575 gtt gac aca gag gcc aac ata gcc acc gag gtc tgc ctc act att ctg        2496
Val Asp Thr Glu Ala Asn Ile Ala Thr Glu Val Cys Leu Thr Ile Leu
            580                 585                 590 gac ctg ctg tct ctc ttt acc cag gtc cac cag aga cag ctc caa caa        2544
Asp Leu Leu Ser Leu Phe Thr Gln Val His Gln Arg Gln Leu Gln Gln
            595                 600                 605 tcc gac tgt caa aat tca ctc atg aaa agg gtc ttc gat act tac atg        2592
Ser Asp Cys Gln Asn Ser Leu Met Lys Arg Val Phe Asp Thr Tyr Met
610                 615                 620                 625 ctg ttt ttc caa gtc aac cag tca gcc tca gcc ctg aaa cac gtg ttt        2640
Leu Phe Phe Gln Val Asn Gln Ser Ala Ser Ala Leu Lys His Val Phe
                630                 635                 640 gct tct tta aga ctg ttt gtg tgc aag ttt ccg tca gcg ttt ttc caa        2688
Ala Ser Leu Arg Leu Phe Val Cys Lys Phe Pro Ser Ala Phe Phe Gln
            645                 650                 655 ggg cct gct gac ctc tgt ggc tca ttc tgc tat gaa atc ctc aaa tgc        2736
Gly Pro Ala Asp Leu Cys Gly Ser Phe Cys Tyr Glu Ile Leu Lys Cys
            660                 665                 670 tgt aac cac agg tca agg ttg act cag atg gaa gct tca gca ctt cta        2784
Cys Asn His Arg Ser Arg Leu Thr Gln Met Glu Ala Ser Ala Leu Leu
            675                 680                 685 tac ttc ttc atg agc aag aac ttt gag ttt aac aag cag aag tca att        2832
```

```
                                                          -continued

Tyr Phe Met Ser Lys Asn Phe Glu Phe Asn Lys Gln Lys Ser Ile
690             695                 700                 705 gtc cgg tct cac tta caa ctc atc aaa gca gtg agc cag tta ata gct    2880
Val Arg Ser His Leu Gln Leu Ile Lys Ala Val Ser Gln Leu Ile Ala
            710                 715                 720 gat gcg ggg atc gga ggg tct cgc ttt caa cac tcc ctt gca atc acg    2928
Asp Ala Gly Ile Gly Gly Ser Arg Phe Gln His Ser Leu Ala Ile Thr
                725                 730                 735 aac aac ttt gcc aat gga gat aaa cag atg aaa aac agc aat ttc cca    2976
Asn Asn Phe Ala Asn Gly Asp Lys Gln Met Lys Asn Ser Asn Phe Pro
            740                 745                 750 gca gag gtg aaa gat ctg act aaa cgt ata agg act gtt ttg atg gcc    3024
Ala Glu Val Lys Asp Leu Thr Lys Arg Ile Arg Thr Val Leu Met Ala
755                 760                 765 aca gcc cag atg aag gag cat gag aag gac cca gag atg ctg gtg gac    3072
Thr Ala Gln Met Lys Glu His Glu Lys Asp Pro Glu Met Leu Val Asp
770                 775                 780                 785 ctt caa tac agc cta gca aac tcc tat gca agt acc ccg gag tta cgg    3120
Leu Gln Tyr Ser Leu Ala Asn Ser Tyr Ala Ser Thr Pro Glu Leu Arg
                790                 795                 800 agg acc tgg ctg gaa agc atg gcc aag att cat gca aga aat gga gac    3168
Arg Thr Trp Leu Glu Ser Met Ala Lys Ile His Ala Arg Asn Gly Asp
            805                 810                 815 ctg tct gag gct gcg atg tgt tac atc cat ata gct gca ctt att gca    3216
Leu Ser Glu Ala Ala Met Cys Tyr Ile His Ile Ala Ala Leu Ile Ala
                820                 825                 830 gaa tac ctg aag cgc aag ggt tac tgg aaa atg gaa aag att tgc aca    3264
Glu Tyr Leu Lys Arg Lys Gly Tyr Trp Lys Met Glu Lys Ile Cys Thr
835                 840                 845 cca ccc ctg ctt cca gaa gac acc caa ccc tgt gat agc aac tta tta    3312
Pro Pro Leu Leu Pro Glu Asp Thr Gln Pro Cys Asp Ser Asn Leu Leu
850                 855                 860                 865 cta aca act cca ggc gga gga agc atg ttc tct atg gga tgg cca gcc    3360
Leu Thr Thr Pro Gly Gly Gly Ser Met Phe Ser Met Gly Trp Pro Ala
                870                 875                 880 ttt ctg agc atc acc cca aac att aaa gaa gaa gga gca atg aaa gag    3408
Phe Leu Ser Ile Thr Pro Asn Ile Lys Glu Glu Gly Ala Met Lys Glu
            885                 890                 895 gat tct gga atg caa gac acc ccg tac aat gag aac atc ctg gtg gaa    3456
Asp Ser Gly Met Gln Asp Thr Pro Tyr Asn Glu Asn Ile Leu Val Glu
                900                 905                 910 cag ctg tat atg tgt gtg gag ttc ctt tgg aag tct gaa cga tac gaa    3504
Gln Leu Tyr Met Cys Val Glu Phe Leu Trp Lys Ser Glu Arg Tyr Glu
915                 920                 925 ctc atc gct gat gtc aat aag ccc atc atc gct gtc ttt gaa aag caa    3552
Leu Ile Ala Asp Val Asn Lys Pro Ile Ile Ala Val Phe Glu Lys Gln
930                 935                 940                 945 cga gac ttc aaa aaa tta tca gat ctc tat tat gac atc cac cgg tcc    3600
Arg Asp Phe Lys Lys Leu Ser Asp Leu Tyr Tyr Asp Ile His Arg Ser
                950                 955                 960 tat ctg aaa gtg gca gag gtg gtg aat tcg gag aag cga ttg ttt ggt    3648
Tyr Leu Lys Val Ala Glu Val Val Asn Ser Glu Lys Arg Leu Phe Gly
            965                 970                 975 cgt tac tat aga gtg gcg ttt tat ggg cag gga ttc ttt gag gag gag    3696
Arg Tyr Tyr Arg Val Ala Phe Tyr Gly Gln Gly Phe Phe Glu Glu Glu
                980                 985                 990 gaa ggt aaa gag tat atc tac aaa gag cct aag ctg aca ggg ctc tcg    3744
Glu Gly Lys Glu Tyr Ile Tyr Lys Glu Pro Lys Leu Thr Gly Leu Ser
995                 1000                1005
```

```
                                                  -continued gag atc tcc caa agg ctt ctc aag ctc tat gca gac aaa ttt gga gca    3792
Glu Ile Ser Gln Arg Leu Leu Lys Leu Tyr Ala Asp Lys Phe Gly Ala
1010            1015                1020                1025 gac aat gtg aaa ata att caa gat tcc aac aag gta aac ccc aag gat    3840
Asp Asn Val Lys Ile Ile Gln Asp Ser Asn Lys Val Asn Pro Lys Asp
        1030                1035                1040 ctg gac ccc aaa tat gcc tat att cag gtg acc tat gtc aca cca ttc    3888
Leu Asp Pro Lys Tyr Ala Tyr Ile Gln Val Thr Tyr Val Thr Pro Phe
            1045                1050                1055 ttt gaa gaa aag gaa atc gag gac cga aag aca gac ttt gaa atg cat    3936
Phe Glu Glu Lys Glu Ile Glu Asp Arg Lys Thr Asp Phe Glu Met His
        1060                1065                1070 cac aac atc aat cgc ttt gtc ttt gag aca ccc ttc act ctg tca ggc    3984
His Asn Ile Asn Arg Phe Val Phe Glu Thr Pro Phe Thr Leu Ser Gly
1075            1080                1085 aag aag cac gga gga gtg gct gag cag tgc aag cgg agg aca gtc ctg    4032
Lys Lys His Gly Gly Val Ala Glu Gln Cys Lys Arg Arg Thr Val Leu
1090            1095                1100                1105 acc aca agc cac ttg ttc ccc tac gta aag aag agg atc cag gtc atc    4080
Thr Thr Ser His Leu Phe Pro Tyr Val Lys Lys Arg Ile Gln Val Ile
            1110                1115                1120 agc caa tca agc aca gag ctg aat cct atc gag gtg gca att gat gag    4128
Ser Gln Ser Ser Thr Glu Leu Asn Pro Ile Glu Val Ala Ile Asp Glu
        1125                1130                1135 atg tcc agg aag gtc tct gag ctt aat cag ctg tgc acc aca gag gag    4176
Met Ser Arg Lys Val Ser Glu Leu Asn Gln Leu Cys Thr Thr Glu Glu
        1140                1145                1150 gtg gat atg atc cgc cta cag ctc aaa ctc cag ggc agt gtc agc gtg    4224
Val Asp Met Ile Arg Leu Gln Leu Lys Leu Gln Gly Ser Val Ser Val
        1155                1160                1165 aag gtc aat gct ggg cca atg gct tat gct cga gcc ttt ctt gaa gaa    4272
Lys Val Asn Ala Gly Pro Met Ala Tyr Ala Arg Ala Phe Leu Glu Glu
1170            1175                1180                1185 act aat gca aag aag tat gct gac aac caa gtt aag cta cta aag gaa    4320
Thr Asn Ala Lys Lys Tyr Ala Asp Asn Gln Val Lys Leu Leu Lys Glu
            1190                1195                1200 ata ttc agg caa ttt gca gat gcg tgt ggg cag gct ctt gat gtg aat    4368
Ile Phe Arg Gln Phe Ala Asp Ala Cys Gly Gln Ala Leu Asp Val Asn
        1205                1210                1215 gag cgt ctc atc aag gaa gac cag ctg gag tac cag gaa gaa ctg agg    4416
Glu Arg Leu Ile Lys Glu Asp Gln Leu Glu Tyr Gln Glu Glu Leu Arg
        1220                1225                1230 tcc cat tat aag gac atg ctc agt gaa ctg tct gcc atc atg aat gag    4464
Ser His Tyr Lys Asp Met Leu Ser Glu Leu Ser Ala Ile Met Asn Glu
        1235                1240                1245 cag att acg ggc agg gac gac cca gca aag tgc gga gtg gag cga ccc    4512
Gln Ile Thr Gly Arg Asp Asp Pro Ala Lys Cys Gly Val Glu Arg Pro
1250            1255                1260                1265 tac acc aca cgt gta act agc aag ggg acc gcg gct gta cct gtg gtc    4560
Tyr Thr Thr Arg Val Thr Ser Lys Gly Thr Ala Ala Val Pro Val Val
            1270                1275                1280 tcc atc tca tcc agt gcg gag gtt tga gaggaaccct ggagcatccg           4607
Ser Ile Ser Ser Ser Ala Glu Val *
            1285 atgcacctct cagagaactc tctaaatgtt ttgcagctaa tctcgggaa gaaaaagata   4667 gatttaattt atttgaagtt tttacagtgt taatcttgtt taccttgcta gcttgggaat   4727 tttgccagcc tctgaatttg cacattttct atgattcctt tgtttccttg aagtagtatt   4787 gatcaagcca cgctaaacat tgttctgaa attccaatga acgtgcagct taaaagcaaa    4847
```

-continued

```
ctgagtttgc tcttgggtgt aatttgttca attccaggtc cttgtacacg catttagag     4907 gtcaaagtga atgttttat aacatttaag catatttcca atgtaaatag aagattgtaa     4967
aatatatggt ttttatcaca tttcaaagaa tgttttagt tgatacttat gaaagtacca     5027
aaattatatg ggtaacgttt cagatcttat attaaaatat ttgtgtatgt gtaaaaactg     5087
ttcgataaat actaatctct aaagtttgtg gactaccttt atttgtaata tatgtgctttt    5147 taagagcaat gggatgtgaa attacaaaaa gtattttgct gttgataata tgaatatgaa     5207
taaaaac                                                               5214
```

<210> SEQ ID NO 3
<211> LENGTH: 5688
<212> TYPE: DNA
<213> ORGANISM: H. sapiens
<220> FEATURE:
<221> NAME/KEY: CDS
<222> LOCATION: (1195)...(5061)

<400> SEQUENCE: 3

```
gccccggcgg cgttctagaa ctagtggatc ccccgggctg caggaattcg gcacgagcca     60
aaatcgaatt tgtcttgatg ggaaacattg caagtggtgc cgaaccttat attaagaacc    120
cagactccaa caagtatgca caaaagatac taaaatccaa cagacaattc tgcagcaaat    180
tgggaaaata ccgtatgcct tttgcttggg cagtaagatc agtatttaag gacaaccagg    240
gaaatgtgga cagagactca agattttcac cattgtttag acaagaaagt agcaagattt    300
caactgagga cctagttaaa ctagtatcag attatagaag ggccgacaga ataagcaaaa    360
tgcagaccat tcctggaagc ctggatattg ctgttgacac cgttcccttg gagcatccaa    420
cctttcaaca tgatggctca aacagaaccc acagtggagg tggaagaatt tgtttacgat    480
tcaacaaagt attgtcggcc ttacagagta tataaaaatc aaatttatat ttaccccaaa    540
cacctcaagt atgatagcca gaaatgcttc aacaaggcac ggaatataac tgtgtgcatt    600
gaattcaaaa attcagatga agaaagtgcc aagcccctga agtgtattta tggaaaacct    660
gaagggcccc tcttcacctc agccgcctac acagcagttc tgcaccactc tcagaatccg    720
gatttctcag atgaggtgaa aattgagcta ccaacacaac tccatgagaa acaccatatt    780
ttgttttctt tttatcacgt cacctgtgac atcaatgcaa agctaatgc caaaaagaag     840 gaggctctgg aaacgtcagt tggatatgct tggcttcctc tgatgaaaca cgatcagata    900
gcttctcaag agtacaacat cccaatagca acaagtctgc ctcctaatta tttaagcttt    960
caagattctg caagtggaaa gcatggtggg agtgacatta aatgggttga tggtggcaaa   1020
ccacttttca agtgtcgac atttgttgta tcaacagtaa atactcagga tccacatgtg    1080
aatgcatttt tccaagagtg ccaaaaaaga gagaaagata tgtctcagtc acctacctca    1140
aatttcatcc gctcttgtaa gaacttattg aatgtggaaa agattcatgc aatc atg     1197
                                                                     Met
                                                                      1 agt ttt ctg cct ata att ttg aat cag ctc ttc aaa gtt ctg gta cag    1245
Ser Phe Leu Pro Ile Ile Leu Asn Gln Leu Phe Lys Val Leu Val Gln
        5                   10                  15 aat gag gaa gat gaa ata act aca act gtc acc agg gtt ctg ccc gac    1293
Asn Glu Glu Asp Glu Ile Thr Thr Thr Val Thr Arg Val Leu Pro Asp
    20                  25                  30 att gtg gcc aag tgc cat gag gag cag ctg gat cat tct gtc cag tca    1341
Ile Val Ala Lys Cys His Glu Glu Gln Leu Asp His Ser Val Gln Ser
35                  40                  45
```

-continued

```
tat att aag ttc gtg ttc aag acc agg gca tgc aag gag agg cct gta      1389
Tyr Ile Lys Phe Val Phe Lys Thr Arg Ala Cys Lys Glu Arg Pro Val
 50                  55                  60                  65 cat gag gac ctg gct aaa aat gtg act ggt ctt ttg aaa tca aat gac      1437
His Glu Asp Leu Ala Lys Asn Val Thr Gly Leu Leu Lys Ser Asn Asp
                 70                  75                  80 tca cca aca gta aag cat gtc cta aag cat tcc tgg ttc ttc ttt gca      1485
Ser Pro Thr Val Lys His Val Leu Lys His Ser Trp Phe Phe Phe Ala
             85                  90                  95 att atc cta aaa tcg atg gca cag cac ttg att gac aca aat aaa atc      1533
Ile Ile Leu Lys Ser Met Ala Gln His Leu Ile Asp Thr Asn Lys Ile
        100                 105                 110 cag ctt ccc cgg cct cag aga ttt cct gaa tct tac caa aat gaa ttg      1581
Gln Leu Pro Arg Pro Gln Arg Phe Pro Glu Ser Tyr Gln Asn Glu Leu
    115                 120                 125 gac aat ctt gtc atg gtc cta tcc gac cat gtg att tgg aaa tac aag      1629
Asp Asn Leu Val Met Val Leu Ser Asp His Val Ile Trp Lys Tyr Lys
130                 135                 140                 145 gat gcc ctt gaa gaa aca aga agg gca acc cac agc gtt gcc aga ttt      1677
Asp Ala Leu Glu Glu Thr Arg Arg Ala Thr His Ser Val Ala Arg Phe
                150                 155                 160 ctc aag cgc tgc ttt aca ttt atg gac cgg ggg tgt gtg ttt aag atg      1725
Leu Lys Arg Cys Phe Thr Phe Met Asp Arg Gly Cys Val Phe Lys Met
            165                 170                 175 gtc aac aat tac atc agc atg ttc tcc tcc ggt gac ctt aag acc ttg      1773
Val Asn Asn Tyr Ile Ser Met Phe Ser Ser Gly Asp Leu Lys Thr Leu
        180                 185                 190 tgc cag tat aaa ttt gat ttt ctt caa gaa gta tgt caa cat gaa cac      1821
Cys Gln Tyr Lys Phe Asp Phe Leu Gln Glu Val Cys Gln His Glu His
    195                 200                 205 ttt atc cct ttg tgt ctg ccc ata aga tca gca aac att cca gat cct      1869
Phe Ile Pro Leu Cys Leu Pro Ile Arg Ser Ala Asn Ile Pro Asp Pro
210                 215                 220                 225 ttg aca cct tca gaa tcg act caa gag tta cat gca tca gat atg cct      1917
Leu Thr Pro Ser Glu Ser Thr Gln Glu Leu His Ala Ser Asp Met Pro
                230                 235                 240 gaa tat tca gtc aca aat gaa ttt tgt cgg aag cat ttc tta atc gga      1965
Glu Tyr Ser Val Thr Asn Glu Phe Cys Arg Lys His Phe Leu Ile Gly
            245                 250                 255 att ctg ctc cga gaa gtt ggc ttt gcc ctg cag gaa gac caa gat gtc      2013
Ile Leu Leu Arg Glu Val Gly Phe Ala Leu Gln Glu Asp Gln Asp Val
        260                 265                 270 aga cac tta gct tta gct gtc cta aaa aat cta atg gct aag cat tca      2061
Arg His Leu Ala Leu Ala Val Leu Lys Asn Leu Met Ala Lys His Ser
    275                 280                 285 ttt gat gat cga tac aga gag cca aga aag cag gcc cag ata gca agt      2109
Phe Asp Asp Arg Tyr Arg Glu Pro Arg Lys Gln Ala Gln Ile Ala Ser
290                 295                 300                 305 tta tac atg ccc ctg tac ggc atg ctc ctg gac aat atg cca agg att      2157
Leu Tyr Met Pro Leu Tyr Gly Met Leu Leu Asp Asn Met Pro Arg Ile
                310                 315                 320 tat ctg aag gac ctg tat cct ttt act gtc aat aca tct aat cag ggg      2205
Tyr Leu Lys Asp Leu Tyr Pro Phe Thr Val Asn Thr Ser Asn Gln Gly
            325                 330                 335 tct aga gat gat cta agc acc aat gga gga ttt caa agc cag aca gct      2253
Ser Arg Asp Asp Leu Ser Thr Asn Gly Gly Phe Gln Ser Gln Thr Ala
        340                 345                 350 atc aaa cat gca aac tct gtg gat aca tca ttt tct aaa gat gtt tta      2301
Ile Lys His Ala Asn Ser Val Asp Thr Ser Phe Ser Lys Asp Val Leu
```

```
              355                 360                 365
aat tcc ata gca gca ttt tca tca ata gct att tct aca gta aac cat    2349
Asn Ser Ile Ala Ala Phe Ser Ser Ile Ala Ile Ser Thr Val Asn His
370                 375                 380                 385 gct gac tcc aga gca tct tta gca agt ctt gac tcc aat cca agt acc    2397
Ala Asp Ser Arg Ala Ser Leu Ala Ser Leu Asp Ser Asn Pro Ser Thr
                390                 395                 400 aat gag aag agc agt gag aag acg gac aac tgt gaa aag atc cca aga    2445
Asn Glu Lys Ser Ser Glu Lys Thr Asp Asn Cys Glu Lys Ile Pro Arg
        405                 410                 415 ccc ttg gct ttg att ggc tca act ctt cga ttt gac agg tta gat caa    2493
Pro Leu Ala Leu Ile Gly Ser Thr Leu Arg Phe Asp Arg Leu Asp Gln
            420                 425                 430 gca gaa acc agg agt ctc ctg atg tgt ttt ctt cac att atg aaa acg    2541
Ala Glu Thr Arg Ser Leu Leu Met Cys Phe Leu His Ile Met Lys Thr
435                 440                 445 att tcg tac gag act ctg att gcc tac tgg cag aga gct ccc agc cca    2589
Ile Ser Tyr Glu Thr Leu Ile Ala Tyr Trp Gln Arg Ala Pro Ser Pro
450                 455                 460                 465 gag gtg tcc gac ttc ttc agc atc ttg gac gtt tgt ctt caa aat ttc    2637
Glu Val Ser Asp Phe Phe Ser Ile Leu Asp Val Cys Leu Gln Asn Phe
                470                 475                 480 aga tac cta gga aaa cgc aac ata ata aga aaa att gct gct gca ttt    2685
Arg Tyr Leu Gly Lys Arg Asn Ile Ile Arg Lys Ile Ala Ala Ala Phe
            485                 490                 495 aaa ttt gtg cag tcc acc cag aac aat gga act ctc aaa gga tcc aat    2733
Lys Phe Val Gln Ser Thr Gln Asn Asn Gly Thr Leu Lys Gly Ser Asn
        500                 505                 510 cct tcc tgc cag aca tca ggg ctc ttg gca caa tgg atg cac tcc act    2781
Pro Ser Cys Gln Thr Ser Gly Leu Leu Ala Gln Trp Met His Ser Thr
515                 520                 525 tcc agg cat gaa ggc cat aag cag cac aga tca caa act tta cct ata    2829
Ser Arg His Glu Gly His Lys Gln His Arg Ser Gln Thr Leu Pro Ile
530                 535                 540                 545 att cga ggc aaa aat gca ctt tct aac ccc aaa ctc tta cag atg tta    2877
Ile Arg Gly Lys Asn Ala Leu Ser Asn Pro Lys Leu Leu Gln Met Leu
                550                 555                 560 gac aat acc atg acc agc aac tcc aat gaa ata gac atc gtg cat cat    2925
Asp Asn Thr Met Thr Ser Asn Ser Asn Glu Ile Asp Ile Val His His
            565                 570                 575 gta gac act gag gcc aat ata gct acg gag ggt tgc ctc act att ctg    2973
Val Asp Thr Glu Ala Asn Ile Ala Thr Glu Gly Cys Leu Thr Ile Leu
        580                 585                 590 gac ctg gta tcc ctc ttc aca cag act cat cag aga caa ctc caa caa    3021
Asp Leu Val Ser Leu Phe Thr Gln Thr His Gln Arg Gln Leu Gln Gln
595                 600                 605 tgt gac tgt caa aat tca ttg atg aaa agg ggc ttt gat acc tac atg    3069
Cys Asp Cys Gln Asn Ser Leu Met Lys Arg Gly Phe Asp Thr Tyr Met
610                 615                 620                 625 ctc ttt ttc caa gtc aat cag tca gcc aca gcg ctg aag cat gtg ttt    3117
Leu Phe Phe Gln Val Asn Gln Ser Ala Thr Ala Leu Lys His Val Phe
                630                 635                 640 gcc tcc ttg aga ctg ttt gta tgc aag ttt cct tca gcg ttc ttt caa    3165
Ala Ser Leu Arg Leu Phe Val Cys Lys Phe Pro Ser Ala Phe Phe Gln
            645                 650                 655 ggg cct gct gac ctc tgt gga tca ttc tgt tac gaa gtc cta aaa tgc    3213
Gly Pro Ala Asp Leu Cys Gly Ser Phe Cys Tyr Glu Val Leu Lys Cys
        660                 665                 670 tgt aac cac agg tca cgg tca act cag aca gaa gcc tca gcc ctt ctg    3261
```

```
Cys Asn His Arg Ser Arg Ser Thr Gln Thr Glu Ala Ser Ala Leu Leu
            675                 680                 685 tac ttg ttc atg agg aag aat ttt gaa ttt aac aag cag aag tca att           3309
Tyr Leu Phe Met Arg Lys Asn Phe Glu Phe Asn Lys Gln Lys Ser Ile
690                 695                 700                 705 gtc cgg tcc cac tta caa ctc atc aaa gct gtg agc cag tta ata gcc           3357
Val Arg Ser His Leu Gln Leu Ile Lys Ala Val Ser Gln Leu Ile Ala
                710                 715                 720 gat gct ggg att gga ggc tct cgg ttt caa cat tcg ctt gca att acc           3405
Asp Ala Gly Ile Gly Gly Ser Arg Phe Gln His Ser Leu Ala Ile Thr
            725                 730                 735 aat aat ttc gcc aat gga gat aag caa atg aaa aac agc aat ttc cca           3453
Asn Asn Phe Ala Asn Gly Asp Lys Gln Met Lys Asn Ser Asn Phe Pro
        740                 745                 750 gca gag gtg aag gac ctg act aag cgt ata agg act gtt ttg atg gcc           3501
Ala Glu Val Lys Asp Leu Thr Lys Arg Ile Arg Thr Val Leu Met Ala
755                 760                 765 aca gct cag atg aag gag cac gag aag gac ccc gag atg ctg gtg gat           3549
Thr Ala Gln Met Lys Glu His Glu Lys Asp Pro Glu Met Leu Val Asp
770                 775                 780                 785 ctc cag tac agc ctg gca aac tcc tac gca agc act cct gaa cta cgc           3597
Leu Gln Tyr Ser Leu Ala Asn Ser Tyr Ala Ser Thr Pro Glu Leu Arg
                790                 795                 800 agg acc tgg ctg gaa agt atg gcc aag att cat gcc aga aac gga gat           3645
Arg Thr Trp Leu Glu Ser Met Ala Lys Ile His Ala Arg Asn Gly Asp
            805                 810                 815 tta tct gag gct gcc atg tgt tac atc cat att gct gct ctc att gca           3693
Leu Ser Glu Ala Ala Met Cys Tyr Ile His Ile Ala Ala Leu Ile Ala
        820                 825                 830 gag tat ctg aaa aga aag ggt tac tgg aaa gtg gaa aag att tgc aca           3741
Glu Tyr Leu Lys Arg Lys Gly Tyr Trp Lys Val Glu Lys Ile Cys Thr
835                 840                 845 gca tcc ctg ctc tcg gag gat acc cac ccc tgt gat agc aac tca tta           3789
Ala Ser Leu Leu Ser Glu Asp Thr His Pro Cys Asp Ser Asn Ser Leu
850                 855                 860                 865 cta aca act ccc agt gga gga agc atg ttc tct atg gga tgg cca gct           3837
Leu Thr Thr Pro Ser Gly Gly Ser Met Phe Ser Met Gly Trp Pro Ala
                870                 875                 880 ttt ttg agc att aca ccc aac att aag gaa gaa gga gcc gcg aaa gag           3885
Phe Leu Ser Ile Thr Pro Asn Ile Lys Glu Glu Gly Ala Ala Lys Glu
            885                 890                 895 gat tct gga atg cac gat aca ccc tac aat gag aat atc ctg gtg gag           3933
Asp Ser Gly Met His Asp Thr Pro Tyr Asn Glu Asn Ile Leu Val Glu
        900                 905                 910 cag cta tac atg tgt ggg gag ttt ctc tgg aag tct gag cga tat gaa           3981
Gln Leu Tyr Met Cys Gly Glu Phe Leu Trp Lys Ser Glu Arg Tyr Glu
915                 920                 925 ctc att gct gat gtc aac aag ccc atc att gct gtc ttt gag aaa caa           4029
Leu Ile Ala Asp Val Asn Lys Pro Ile Ile Ala Val Phe Glu Lys Gln
930                 935                 940                 945 cga gac ttc aaa aaa ttg tca gat ctc tac tac gac att cat cgg tca           4077
Arg Asp Phe Lys Lys Leu Ser Asp Leu Tyr Tyr Asp Ile His Arg Ser
                950                 955                 960 tat ctg aaa gtg gca gag gtg gtg aat tcg gag aag cgg ctg ttt ggt           4125
Tyr Leu Lys Val Ala Glu Val Val Asn Ser Glu Lys Arg Leu Phe Gly
            965                 970                 975 cgc tac tat cgt gtg gca ttt tat ggg cag ggc ttt ttt gaa gaa gaa           4173
Arg Tyr Tyr Arg Val Ala Phe Tyr Gly Gln Gly Phe Phe Glu Glu Glu
        980                 985                 990
```

-continued

| | |
|---|---|
| gaa ggt aaa gag tat att tat aaa gag cct aag ctg aca ggt ctg tcc<br>Glu Gly Lys Glu Tyr Ile Tyr Lys Glu Pro Lys Leu Thr Gly Leu Ser<br>    995                         1000                   1005 | 4221 |
| gag att tcc caa aga tta ctc aag ctc tat gca gat aaa ttt gga gca<br>Glu Ile Ser Gln Arg Leu Leu Lys Leu Tyr Ala Asp Lys Phe Gly Ala<br>1010                 1015                 1020                 1025 | 4269 |
| gac aat gtg aag ata atc cag gat tcc aac aag gta aac ccc aag gat<br>Asp Asn Val Lys Ile Ile Gln Asp Ser Asn Lys Val Asn Pro Lys Asp<br>                 1030                 1035                 1040 | 4317 |
| ttg gac ccc aaa tat gcc tac atc cag gtg acc tat gtg acg ccg ttc<br>Leu Asp Pro Lys Tyr Ala Tyr Ile Gln Val Thr Tyr Val Thr Pro Phe<br>             1045                 1050                 1055 | 4365 |
| ttt gag gaa aag gaa atc gaa gac cgg aag aca gat ttc gaa atg cac<br>Phe Glu Glu Lys Glu Ile Glu Asp Arg Lys Thr Asp Phe Glu Met His<br>         1060                 1065                 1070 | 4413 |
| cac aac atc aac cgc ttt gtc ttc gag aca ccc ttc acg ctg tcg ggc<br>His Asn Ile Asn Arg Phe Val Phe Glu Thr Pro Phe Thr Leu Ser Gly<br>        1075                 1080                 1085 | 4461 |
| aag aag cac ggt ggg gtg gcg gag cag tgc aag cgg cgg acg atc ctg<br>Lys Lys His Gly Gly Val Ala Glu Gln Cys Lys Arg Arg Thr Ile Leu<br>1090               1095               1100                1105 | 4509 |
| aca acg agt cac ctg ttc ccc tac gtg aag aag agg atc cag gtc atc<br>Thr Thr Ser His Leu Phe Pro Tyr Val Lys Lys Arg Ile Gln Val Ile<br>             1110                 1115                1120 | 4557 |
| agc caa tca agc aca gag ctg aat cct att gaa gtg gca att gac gag<br>Ser Gln Ser Ser Thr Glu Leu Asn Pro Ile Glu Val Ala Ile Asp Glu<br>         1125                 1130                 1135 | 4605 |
| atg tcc agg aag gtc tct gag ctt aat cag ctt tgc aca atg gaa gaa<br>Met Ser Arg Lys Val Ser Glu Leu Asn Gln Leu Cys Thr Met Glu Glu<br>             1140                 1145                1150 | 4653 |
| gtg gac atg atc agc cta cag ctc aaa ctg caa gga agt gtc agc gtg<br>Val Asp Met Ile Ser Leu Gln Leu Lys Leu Gln Gly Ser Val Ser Val<br>1155               1160               1165 | 4701 |
| aag gtt aat gct ggg cca atg gcc tat gca cga gct ttt ctt gaa gaa<br>Lys Val Asn Ala Gly Pro Met Ala Tyr Ala Arg Ala Phe Leu Glu Glu<br>1170               1175               1180                1185 | 4749 |
| acc aat gca aag aag tac cct gac aac caa gta aag ctt ttg aag gag<br>Thr Asn Ala Lys Lys Tyr Pro Asp Asn Gln Val Lys Leu Leu Lys Glu<br>                 1190                 1195                1200 | 4797 |
| atc ttc agg caa ttt gca gat gca tgt ggg cag gcc ctt gac gtg aat<br>Ile Phe Arg Gln Phe Ala Asp Ala Cys Gly Gln Ala Leu Asp Val Asn<br>             1205                 1210                 1215 | 4845 |
| gag cgc ctc atc aaa gag gac cag ctg gag tac cag gaa gaa ctg agg<br>Glu Arg Leu Ile Lys Glu Asp Gln Leu Glu Tyr Gln Glu Glu Leu Arg<br>         1220                 1225                 1230 | 4893 |
| tcc cac tac aag gac atg ctc agc gaa ctc tcc aca gtc atg aat gag<br>Ser His Tyr Lys Asp Met Leu Ser Glu Leu Ser Thr Val Met Asn Glu<br>        1235                 1240                 1245 | 4941 |
| cag att acg ggc agg gac gac ctg tca aag cgc gga gtg gac caa acc<br>Gln Ile Thr Gly Arg Asp Asp Leu Ser Lys Arg Gly Val Asp Gln Thr<br>1250               1255               1260                1265 | 4989 |
| tgc act cga gta att agc aaa gca act ccg gcc cta ccc acg gtc tcc<br>Cys Thr Arg Val Ile Ser Lys Ala Thr Pro Ala Leu Pro Thr Val Ser<br>             1270                 1275                1280 | 5037 |
| atc tca tct agt gct gaa gtc tga gaggaaccct ggagcatccg atgcacctct<br>Ile Ser Ser Ser Ala Glu Val *<br>         1285 | 5091 |
| cagagaactc tctaaatgtt ttgcagctaa tctcgggaa gaaaaagata gatttaattt | 5151 |
| atttgaagtt tttacagtgt taatcttgtt taccttgcta gcttgggaat tttgccagcc | 5211 |

```
tctgaatttg cacattttct atgattcctt tgtttccttg aagtagtatt gatcaagcca   5271
cgctaaacat tgttctgaa attccaatga acgtgcagct taaaagcaaa ctgagtttgc   5331
tcttgggtgt aatttgttca attccaggtc cttgtacacg cattttagag gtcaaagtga   5391
atgtttttat aacatttaag catatttcca atgtaaatag aagattgtaa aatatatggt   5451
ttttatcaca tttcaaagaa tgttttttagt tgatacttat gaaagtacca aaattatatg   5511
ggtaacgttt cagatcttat attaaaatat ttgtgtatgt gtaaaaactg ttcgataaat   5571
actaatctct aaagtttgtg gactacctt atttgtaata tatgtgcttt taagagcaat   5631
gggatgtgaa attacaaaaa gtattttgct gttgataata tgaatatgaa taaaaac      5688
```

<210> SEQ ID NO 4
<211> LENGTH: 1288
<212> TYPE: PRT
<213> ORGANISM: H. sapiens

<400> SEQUENCE: 4

```
Met Ser Phe Leu Pro Ile Ile Leu Asn Gln Leu Phe Lys Val Leu Val
  1               5                  10                  15

Gln Asn Glu Glu Asp Glu Ile Thr Thr Thr Val Thr Arg Val Leu Pro
             20                  25                  30

Asp Ile Val Ala Lys Cys His Glu Glu Gln Leu Asp His Ser Val Gln
         35                  40                  45

Ser Tyr Ile Lys Phe Val Phe Lys Thr Arg Ala Cys Lys Glu Arg Pro
     50                  55                  60

Val His Glu Asp Leu Ala Lys Asn Val Thr Gly Leu Leu Lys Ser Asn
 65                  70                  75                  80

Asp Ser Pro Thr Val Lys His Val Leu Lys His Ser Trp Phe Phe Phe
                 85                  90                  95

Ala Ile Ile Leu Lys Ser Met Ala Gln His Leu Ile Asp Thr Asn Lys
            100                 105                 110

Ile Gln Leu Pro Arg Pro Gln Arg Phe Pro Glu Ser Tyr Gln Asn Glu
        115                 120                 125

Leu Asp Asn Leu Val Met Val Leu Ser Asp His Val Ile Trp Lys Tyr
    130                 135                 140

Lys Asp Ala Leu Glu Glu Thr Arg Arg Ala Thr His Ser Val Ala Arg
145                 150                 155                 160

Phe Leu Lys Arg Cys Phe Thr Phe Met Asp Arg Gly Cys Val Phe Lys
                165                 170                 175

Met Val Asn Asn Tyr Ile Ser Met Phe Ser Ser Gly Asp Leu Lys Thr
            180                 185                 190

Leu Cys Gln Tyr Lys Phe Asp Phe Leu Gln Glu Val Cys Gln His Glu
        195                 200                 205

His Phe Ile Pro Leu Cys Leu Pro Ile Arg Ser Ala Asn Ile Pro Asp
    210                 215                 220

Pro Leu Thr Pro Ser Glu Ser Thr Gln Glu Leu His Ala Ser Asp Met
225                 230                 235                 240

Pro Glu Tyr Ser Val Thr Asn Glu Phe Cys Arg Lys His Phe Leu Ile
                245                 250                 255

Gly Ile Leu Leu Arg Glu Val Gly Phe Ala Leu Gln Glu Asp Gln Asp
            260                 265                 270

Val Arg His Leu Ala Leu Ala Val Leu Lys Asn Leu Met Ala Lys His
        275                 280                 285
```

```
Ser Phe Asp Asp Arg Tyr Arg Glu Pro Arg Lys Gln Ala Gln Ile Ala
    290                 295                 300

Ser Leu Tyr Met Pro Leu Tyr Gly Met Leu Leu Asp Asn Met Pro Arg
305                 310                 315                 320

Ile Tyr Leu Lys Asp Leu Tyr Pro Phe Thr Val Asn Thr Ser Asn Gln
                325                 330                 335

Gly Ser Arg Asp Asp Leu Ser Thr Asn Gly Gly Phe Gln Ser Gln Thr
            340                 345                 350

Ala Ile Lys His Ala Asn Ser Val Asp Thr Ser Phe Ser Lys Asp Val
        355                 360                 365

Leu Asn Ser Ile Ala Ala Phe Ser Ser Ile Ala Ile Ser Thr Val Asn
    370                 375                 380

His Ala Asp Ser Arg Ala Ser Leu Ala Ser Leu Asp Ser Asn Pro Ser
385                 390                 395                 400

Thr Asn Glu Lys Ser Ser Glu Lys Thr Asp Asn Cys Glu Lys Ile Pro
                405                 410                 415

Arg Pro Leu Ala Leu Ile Gly Ser Thr Leu Arg Phe Asp Arg Leu Asp
            420                 425                 430

Gln Ala Glu Thr Arg Ser Leu Leu Met Cys Phe Leu His Ile Met Lys
        435                 440                 445

Thr Ile Ser Tyr Glu Thr Leu Ile Ala Tyr Trp Gln Arg Ala Pro Ser
    450                 455                 460

Pro Glu Val Ser Asp Phe Phe Ser Ile Leu Asp Val Cys Leu Gln Asn
465                 470                 475                 480

Phe Arg Tyr Leu Gly Lys Arg Asn Ile Ile Arg Lys Ile Ala Ala Ala
                485                 490                 495

Phe Lys Phe Val Gln Ser Thr Gln Asn Asn Gly Thr Leu Lys Gly Ser
            500                 505                 510

Asn Pro Ser Cys Gln Thr Ser Gly Leu Leu Ala Gln Trp Met His Ser
        515                 520                 525

Thr Ser Arg His Glu Gly His Lys Gln His Arg Ser Gln Thr Leu Pro
    530                 535                 540

Ile Ile Arg Gly Lys Asn Ala Leu Ser Asn Pro Lys Leu Leu Gln Met
545                 550                 555                 560

Leu Asp Asn Thr Met Thr Ser Asn Ser Asn Glu Ile Asp Ile Val His
                565                 570                 575

His Val Asp Thr Glu Ala Asn Ile Ala Thr Glu Gly Cys Leu Thr Ile
            580                 585                 590

Leu Asp Leu Val Ser Leu Phe Thr Gln Thr His Gln Arg Gln Leu Gln
        595                 600                 605

Gln Cys Asp Cys Gln Asn Ser Leu Met Lys Arg Gly Phe Asp Thr Tyr
    610                 615                 620

Met Leu Phe Phe Gln Val Asn Gln Ser Ala Thr Ala Leu Lys His Val
625                 630                 635                 640

Phe Ala Ser Leu Arg Leu Phe Val Cys Lys Phe Pro Ser Ala Phe Phe
                645                 650                 655

Gln Gly Pro Ala Asp Leu Cys Gly Ser Phe Cys Tyr Glu Val Leu Lys
            660                 665                 670

Cys Cys Asn His Arg Ser Arg Ser Thr Gln Thr Glu Ala Ser Ala Leu
        675                 680                 685

Leu Tyr Leu Phe Met Arg Lys Asn Phe Glu Phe Asn Lys Gln Lys Ser
    690                 695                 700

Ile Val Arg Ser His Leu Gln Leu Ile Lys Ala Val Ser Gln Leu Ile
```

-continued

```
705                 710                 715                 720
Ala Asp Ala Gly Ile Gly Gly Ser Arg Phe Gln His Ser Leu Ala Ile
                725                 730                 735
Thr Asn Asn Phe Ala Asn Gly Asp Lys Gln Met Lys Asn Ser Asn Phe
                740                 745                 750
Pro Ala Glu Val Lys Asp Leu Thr Lys Arg Ile Arg Thr Val Leu Met
                755                 760                 765
Ala Thr Ala Gln Met Lys Glu His Glu Lys Asp Pro Glu Met Leu Val
                770                 775                 780
Asp Leu Gln Tyr Ser Leu Ala Asn Ser Tyr Ala Ser Thr Pro Glu Leu
785                 790                 795                 800
Arg Arg Thr Trp Leu Glu Ser Met Ala Lys Ile His Ala Arg Asn Gly
                805                 810                 815
Asp Leu Ser Glu Ala Ala Met Cys Tyr Ile His Ile Ala Ala Leu Ile
                820                 825                 830
Ala Glu Tyr Leu Lys Arg Lys Gly Tyr Trp Lys Val Glu Lys Ile Cys
                835                 840                 845
Thr Ala Ser Leu Leu Ser Glu Asp Thr His Pro Cys Asp Ser Asn Ser
                850                 855                 860
Leu Leu Thr Thr Pro Ser Gly Gly Ser Met Phe Ser Met Gly Trp Pro
865                 870                 875                 880
Ala Phe Leu Ser Ile Thr Pro Asn Ile Lys Glu Gly Ala Ala Lys
                885                 890                 895
Glu Asp Ser Gly Met His Asp Thr Pro Tyr Asn Glu Asn Ile Leu Val
                900                 905                 910
Glu Gln Leu Tyr Met Cys Gly Glu Phe Leu Trp Lys Ser Glu Arg Tyr
                915                 920                 925
Glu Leu Ile Ala Asp Val Asn Lys Pro Ile Ile Ala Val Phe Glu Lys
                930                 935                 940
Gln Arg Asp Phe Lys Lys Leu Ser Asp Leu Tyr Tyr Asp Ile His Arg
945                 950                 955                 960
Ser Tyr Leu Lys Val Ala Glu Val Val Asn Ser Glu Lys Arg Leu Phe
                965                 970                 975
Gly Arg Tyr Tyr Arg Val Ala Phe Tyr Gly Gln Gly Phe Phe Glu Glu
                980                 985                 990
Glu Glu Gly Lys Glu Tyr Ile Tyr Lys Glu Pro Lys Leu Thr Gly Leu
                995                 1000                1005
Ser Glu Ile Ser Gln Arg Leu Leu Lys Leu Tyr Ala Asp Lys Phe Gly
      1010                1015                1020
Ala Asp Asn Val Lys Ile Ile Gln Asp Ser Asn Lys Val Asn Pro Lys
1025                1030                1035                1040
Asp Leu Asp Pro Lys Tyr Ala Tyr Ile Gln Val Thr Tyr Val Thr Pro
                1045                1050                1055
Phe Phe Glu Glu Lys Glu Ile Glu Asp Arg Lys Thr Asp Phe Glu Met
                1060                1065                1070
His His Asn Ile Asn Arg Phe Val Phe Glu Thr Pro Phe Thr Leu Ser
      1075                1080                1085
Gly Lys Lys His Gly Gly Val Ala Glu Gln Cys Lys Arg Arg Thr Ile
      1090                1095                1100
Leu Thr Thr Ser His Leu Phe Pro Tyr Val Lys Lys Arg Ile Gln Val
1105                1110                1115                1120
Ile Ser Gln Ser Ser Thr Glu Leu Asn Pro Ile Glu Val Ala Ile Asp
                1125                1130                1135
```

-continued

Glu Met Ser Arg Lys Val Ser Glu Leu Asn Gln Leu Cys Thr Met Glu
            1140                1145                1150

Glu Val Asp Met Ile Ser Leu Gln Leu Lys Leu Gln Gly Ser Val Ser
        1155                1160                1165

Val Lys Val Asn Ala Gly Pro Met Ala Tyr Ala Arg Ala Phe Leu Glu
    1170                1175                1180

Glu Thr Asn Ala Lys Lys Tyr Pro Asp Asn Gln Val Lys Leu Leu Lys
1185                1190                1195                1200

Glu Ile Phe Arg Gln Phe Ala Asp Ala Cys Gly Gln Ala Leu Asp Val
            1205                1210                1215

Asn Glu Arg Leu Ile Lys Glu Asp Gln Leu Gly Tyr Gln Glu Glu Leu
        1220                1225                1230

Arg Ser His Tyr Lys Asp Met Leu Ser Glu Leu Ser Thr Val Met Asn
        1235                1240                1245

Glu Gln Ile Thr Gly Arg Asp Asp Leu Ser Lys Arg Gly Val Asp Gln
        1250                1255                1260

Thr Cys Thr Arg Val Ile Ser Lys Ala Thr Pro Ala Leu Pro Thr Val
1265                1270                1275                1280

Ser Ile Ser Ser Ser Ala Glu Val
            1285

<210> SEQ ID NO 5
<211> LENGTH: 26
<212> TYPE: DNA
<213> ORGANISM: Artificial Sequence
<220> FEATURE:
<223> OTHER INFORMATION: degenerate primer
<221> NAME/KEY: misc_feature
<222> LOCATION: (1)...(26)
<223> OTHER INFORMATION: n = A,T,C or G

<400> SEQUENCE: 5
ggaattccac ngcnccnccn tactga                                        26

<210> SEQ ID NO 6
<211> LENGTH: 29
<212> TYPE: DNA
<213> ORGANISM: Artificial Sequence
<220> FEATURE:
<223> OTHER INFORMATION: degenerate primer
<221> NAME/KEY: misc_feature
<222> LOCATION: (1)...(29)
<223> OTHER INFORMATION: n = A,T,C or G

<400> SEQUENCE: 6
gctctagatc ngcnaagctt tctttagaa                                     29

<210> SEQ ID NO 7
<211> LENGTH: 24
<212> TYPE: PRT
<213> ORGANISM: H. sapiens

<400> SEQUENCE: 7

Leu Leu Ile Asp Pro Glu Asp Asp Gly Gly Gly Asp Pro Thr Ala Pro
1               5                   10                  15

Pro Tyr Phe Lys Lys Leu Ala Asp
            20

<210> SEQ ID NO 8
<211> LENGTH: 24
<212> TYPE: PRT

```
<213> ORGANISM: H. sapiens

<400> SEQUENCE: 8

Pro Leu Leu Pro Glu Asp Asp Gly Gly Gly Asp Pro Thr Ala Pro
 1               5                  10                  15

Pro Tyr Phe Lys Lys Leu Ala Asp
              20

<210> SEQ ID NO 9
<211> LENGTH: 25
<212> TYPE: PRT
<213> ORGANISM: H. sapiens

<400> SEQUENCE: 9

Glu Pro Leu Leu Pro Pro Asp Asp Gly Gly Gly Asp Pro Thr Ala Pro
 1               5                  10                  15

Pro Tyr Phe Lys Lys Lys Leu Ala Asp
              20                  25

<210> SEQ ID NO 10
<211> LENGTH: 21
<212> TYPE: PRT
<213> ORGANISM: M. musculus

<400> SEQUENCE: 10

Pro Pro Leu Leu Pro Glu Asp Thr Gly Gly Gly Asp Thr Pro Tyr Phe
 1               5                  10                  15

Lys Lys Leu Ser Asp
              20

<210> SEQ ID NO 11
<211> LENGTH: 19
<212> TYPE: DNA
<213> ORGANISM: Artificial Sequence
<220> FEATURE:
<223> OTHER INFORMATION: primer

<400> SEQUENCE: 11
ggaagcttca gcacttcta                                              19

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
ggggtacctt ccattttcca gta                                         23

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
ggggtacccc taagctgaca ggg                                         23

<210> SEQ ID NO 14
<211> LENGTH: 23
<212> TYPE: DNA
<213> ORGANISM: Artificial Sequence
```

-continued

```
<220> FEATURE:
<223> OTHER INFORMATION: primer

<400> SEQUENCE: 14
ccactagtca gcttaggctc ttt                                              23

<210> SEQ ID NO 15
<211> LENGTH: 23
<212> TYPE: DNA
<213> ORGANISM: Artificial Sequence
<220> FEATURE:
<223> OTHER INFORMATION: primer

<400> SEQUENCE: 15
ccactagtaa cctccgcact gga                                              23

<210> SEQ ID NO 16
<211> LENGTH: 44
<212> TYPE: DNA
<213> ORGANISM: H. sapiens
<220> FEATURE:
<221> NAME/KEY: misc_feature
<222> LOCATION: (1)...(44)
<223> OTHER INFORMATION: n = A,T,C or G

<400> SEQUENCE: 16
atctnttgtg catactaaag aaaaaataaa tacaaatatt gttt                       44

<210> SEQ ID NO 17
<211> LENGTH: 51
<212> TYPE: DNA
<213> ORGANISM: H. sapiens

<400> SEQUENCE: 17
tagtatcaga ttatagaagg tatgtttttt ttatactctc gaaattaaca t               51

<210> SEQ ID NO 18
<211> LENGTH: 44
<212> TYPE: DNA
<213> ORGANISM: H. sapiens

<400> SEQUENCE: 18
aaagtgccaa gcccctgaag gtgagccaag tcagcaaagg gacc                       44

<210> SEQ ID NO 19
<211> LENGTH: 47
<212> TYPE: DNA
<213> ORGANISM: H. sapiens

<400> SEQUENCE: 19
atttcatccg ctcttgtaag gtaacatgac atgcaagcag tttcagt                    47

<210> SEQ ID NO 20
<211> LENGTH: 50
<212> TYPE: DNA
<213> ORGANISM: H. sapiens

<400> SEQUENCE: 20
cagtaaagca tgtcctaaag gtaagaattt aaagatggtc ctttaactgt                 50

<210> SEQ ID NO 21
<211> LENGTH: 50
<212> TYPE: DNA
<213> ORGANISM: H. sapiens
```

```
<400> SEQUENCE: 21
gcgttgccag atttctcaag gtacagttat atgagatcgc agttctattc                50

<210> SEQ ID NO 22
<211> LENGTH: 45
<212> TYPE: DNA
<213> ORGANISM: H. sapiens
<220> FEATURE:
<221> NAME/KEY: misc_feature
<222> LOCATION: (1)...(45)
<223> OTHER INFORMATION: n = A,T,C or G

<400> SEQUENCE: 22
ganagganga tcacttactg gctctctgta tcgatcatca aatga                     45

<210> SEQ ID NO 23
<211> LENGTH: 43
<212> TYPE: DNA
<213> ORGANISM: H. sapiens
<220> FEATURE:
<221> NAME/KEY: misc_feature
<222> LOCATION: (1)...(43)
<223> OTHER INFORMATION: n = A,T,C or G

<400> SEQUENCE: 23
acttctcgga gcagaattcc nttagaaggt ttgcgcaaat cat                       43

<210> SEQ ID NO 24
<211> LENGTH: 53
<212> TYPE: DNA
<213> ORGANISM: H. sapiens
<220> FEATURE:
<221> NAME/KEY: misc_feature
<222> LOCATION: (1)...(53)
<223> OTHER INFORMATION: n = A,T,C or G

<400> SEQUENCE: 24
ctgncaatac atctaatcag gtacgtttgc acaatatgtc acatttctat gtt            53

<210> SEQ ID NO 25
<211> LENGTH: 50
<212> TYPE: DNA
<213> ORGANISM: H. sapiens
<220> FEATURE:
<221> NAME/KEY: misc_feature
<222> LOCATION: (1)...(50)
<223> OTHER INFORMATION: n = A,T,C or G

<400> SEQUENCE: 25
aagatgtttt aaattcntag caggtacttg agatcttctg agaacactta                50

<210> SEQ ID NO 26
<211> LENGTH: 55
<212> TYPE: DNA
<213> ORGANISM: H. sapiens

<400> SEQUENCE: 26
gacttcttca gcatcttgga gtaagtttta gagttgatga cttaacactt ttttc          55

<210> SEQ ID NO 27
<211> LENGTH: 50
<212> TYPE: DNA
<213> ORGANISM: H. sapiens

<400> SEQUENCE: 27
ttagacaata ccatgaccag taagtaaact gaaataatag gaacaagatg                50
```

<210> SEQ ID NO 28
<211> LENGTH: 52
<212> TYPE: DNA
<213> ORGANISM: H. sapiens

<400> SEQUENCE: 28
ttgagactgt tgtatgcaa ggtaaggatc tccaggtttc aatgaagttt ag          52

<210> SEQ ID NO 29
<211> LENGTH: 54
<212> TYPE: DNA
<213> ORGANISM: H. sapiens

<400> SEQUENCE: 29
gtcccactta caagtaagtg ctgccaattt taattaatgc tgttgttaaa acca        54

<210> SEQ ID NO 30
<211> LENGTH: 51
<212> TYPE: DNA
<213> ORGANISM: H. sapiens
<220> FEATURE:
<221> NAME/KEY: misc_feature
<222> LOCATION: (1)...(51)
<223> OTHER INFORMATION: n = A,T,C or G

<400> SEQUENCE: 30
ttcacctctg ctgggaaarr cgctgttctn tggaaangag agagcctggg t           51

<210> SEQ ID NO 31
<211> LENGTH: 49
<212> TYPE: DNA
<213> ORGANISM: H. sapiens

<400> SEQUENCE: 31
gaaacggaga tttatctgag gtgattagca aggcttggtc atttaccat              49

<210> SEQ ID NO 32
<211> LENGTH: 45
<212> TYPE: DNA
<213> ORGANISM: H. sapiens
<220> FEATURE:
<221> NAME/KEY: misc_feature
<222> LOCATION: (1)...(45)
<223> OTHER INFORMATION: n = A,T,C or G

<400> SEQUENCE: 32
cttcngaaga aggagcgatg aaagaggatt ctggaatgca agata                  45

<210> SEQ ID NO 33
<211> LENGTH: 51
<212> TYPE: DNA
<213> ORGANISM: H. sapiens

<400> SEQUENCE: 33
agatacacca tacaatgagg ttagaccaaa attatctcat gtacagtaac c           51

<210> SEQ ID NO 34
<211> LENGTH: 47
<212> TYPE: DNA
<213> ORGANISM: H. sapiens
<220> FEATURE:
<221> NAME/KEY: misc_feature
<222> LOCATION: (1)...(47)
<223> OTHER INFORMATION: n = A,T,C or G -continued

```
<400> SEQUENCE: 34
aagcggcgga cgatnctgnc aagtnggtgc aggtagccgg gccacac                47
```